United States Patent
Yan et al.

(10) Patent No.: US 6,858,420 B2
(45) Date of Patent: Feb. 22, 2005

(54) ISOLATED HUMAN KINASE PROTEINS, NUCLEIC ACID MOLECULES ENCODING HUMAN KINASE PROTEINS, AND USES THEREOF

(75) Inventors: Chunhua Yan, Boyds, MD (US); Jane Abu-Threideh, Germantown, MD (US); Wei Shao, Frederick, MD (US); Gennady Merkulov, Baltimore, MD (US); Valentina Di Francesco, Rockville, MD (US); Ellen M. Beasley, Darnestown, MD (US)

(73) Assignee: Applera Corporation, Norwalk, CT (US)

(*) Notice: Subject to any disclaimer, the term of this patent is extended or adjusted under 35 U.S.C. 154(b) by 196 days.

(21) Appl. No.: 10/153,919

(22) Filed: May 24, 2002

(65) Prior Publication Data

US 2003/0166219 A1 Sep. 4, 2003

Related U.S. Application Data

(62) Division of application No. 09/739,455, filed on Dec. 19, 2000, now Pat. No. 6,413,756.
(60) Provisional application No. 60/209,585, filed on Jun. 6, 2000.

(51) Int. Cl.$^7$ ................................................. C12N 9/12
(52) U.S. Cl. ...................................................... 435/194
(58) Field of Search ........................................ 435/194

(56) References Cited

FOREIGN PATENT DOCUMENTS

WO      WO 00 73469 A      12/2000

OTHER PUBLICATIONS

Lee, L–S., et al. (1977) J. Biol. Chem. 252(16), 5685–5691.*
Chern, C.J., et al. (1972) J. Biol. Chem 247(23), 7173–7180.*
Yoshida, A., et al. (1972) J. Biol. Chem. 247(2), 446–449.*
Yoshida, A., et al. (1972) J. Biol. Chem. 247(2), 440–445.*
Ellims, P.H., et al. (1980) J. Biol. Chem. 255(23), 11290–11295.*
Simkowski, K.W., et al. (1980) J. Biol. Chem 255(13), 6456–6461.*
Rubin, C.S. (1979) J. Biol, Chem. 254(24), 12439–12449.*
Andres, C.M., et al. (1979) J. Biol. Chem. 254(22), 11388–11393.*
Abe et al. "Extracellular Signal–Regulated Kinase 7 (ERK7), a Novel ERK with a C–Terminal Domain that Regulates its Activity, its Cellular Localization, and Cell Growth." Molecular and Cellular Biology. Washington, DC vol. 19, No. 2, Feb. 1999 pp. 1301–1312, XP002172155.
Barton G.J. "Protein Sequence Alignment and Database Scanning." Protein Structure Prediction. A Practical Approach. 1996. PP. 31–63. XP000829540.
George et al. "Current Methods in Sequence Comparison and Analysis." Macromolecular Sequencing and Synthesis Selected Methods and Applications 1988. Pages 127–149.
International Search report dated Mar. 27, 2003, PCT/US01/48347.
Results of BLAST search SEQ ID NO:2 against Derwent (FastAlert and GeneSeqP) and NCBI (pataa) protein patent databases on Jun. 10, 2003.

* cited by examiner

Primary Examiner—Charles L. Patterson, Jr.
(74) Attorney, Agent, or Firm—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

8 Claims, 29 Drawing Sheets

```
   1 GGCGTCCTGG CCGCCATGTG CACCGTAGTG GACCCTCGCA TTGTCCGGAG
  51 ATACCTACTC AGGCGGCAGC TCGGGCAGGG GGCCTATGGC ATTGTGTGGA
 101 AGGCAGTGGA CCGGAGGACT GGTGAGGTCG TGGCCATCAA GAAAATCTTT
 151 GATGCTTTTA GGGATAAGAC AGATGCCCAG AGAACATTCC GGGAAATCAC
 201 GCTCCTCCAG GAGTTTGGGG ACCATCCCAA CATCATCAGC CTCCTTGACG
 251 TGATCCGGGC AGAGAACGAC AGGGACATTT ACCTGGTGTT TGAGTTTATG
 301 GACACTGACC TGAACGCAGT CATCCGGAAG GGCGGCCTGC TGCAGGACGT
 351 CCACGTGCGC TCCATCTTCT ACCAGCTCCT GCGGGCCACC CGGTTCCTCC
 401 ACTCGGGGCA CGTTGTGCAC CGGGACCAGA AGCCGTCCAA TGTGCTCCTG
 451 GATGCCAACT GCACAGTGAA GCTGTGTGAC TTTGGCCTGG CCCGCTCCCT
 501 GGGCGACCTC CCCGAGGGGC CTGAGGACCA GGCCGTGACA GAGTACGTGG
 551 CCACACGCTG GTACCGAGCA CCGGAGGTGC TGCTCTCTTC GCACCGATAC
 601 ACCCTTGGGG TGGACATGTG GAGTCTGGGC TGTATCCTGG GGAGATGCT
 651 GCGGGGGAGA CCCCTGTTCC CCGGCAAGTC CACCCTCCAC CAGCTGGAGC
 701 TGATCCTGGA GACCATCCCA CCGCCATCTG AGGAGGCCCA CAGGCCACGA
 751 CAGACGCTGG ATGCCCTCCT ACCGCCAGAC ACCTCCCCAG AGGCCTTGGA
 801 CCTCCTTAGG CGACTCCTGG TGTTCGCCCC GGACAAGCGG TTAAGCGCGA
 851 CCCAGGCACT GCAGCACCCC TACGTGCAGA GGTTCCACTG CCCCAGCGAC
 901 GAGTGGGCAC GAGAGGCAGA TGTGCGGCCC CGGGCACACG AAGGGGTCCA
 951 GCTCTCTGTG CCTGAGTACC GCAGCCGCGT CTATCAGATG ATCCTGGAGT
1001 GTGGAGGCAG CAGCGGCACC TCGAGAGAGA AGGGCCCGGA GGGTGTCTCC
1051 CCAAGCCAGG CACACCTGCA CAAACCCAGA GCCGACCCTC AGCTGCCTTC
1101 TAGGACACCT GTGCAGGGTC CCAGACCCAG GCCCCAGAGC AGCCCAGGCC
1151 ATGACCCTGC CGAGCACGAG TCCCCCCGTG CAGCCAAGAA CGTTCCCAGG
1201 CAGAACTCCG CTCCCCTGCT CCAAACTGCT CTCCTAGAGA ATGGGGAAAG
1251 GCCCCCTGGG GCGAAGGAAG CGCCCCCCTT GACACTCTCG CTGGTGAAGC
1301 CAAGCGGGAG GGGAGCTGCG CCCTCCCTGA CCTCCCAGGC TGCGGCTCAG
1351 GTGGCCAACC AGGCCCTGAT CCGGGGTGAC TGGAACCGGG GCGGTGGGGT
1401 GAGGGTGGCC AGCGTACAAC AGGTCCCTCC CCGGCTTCCT CCGGAGGCCC
1451 GGCCCGGCCG GAGGATGTTC AGCACCTCTG CCTTGCAGGG TGCCCAGGGG
1501 GGTGCCAGGG CTTTGCTTGG AGGCTACTCC CAAGCCTACG GGACTGTCTG
1551 CCACTCGGCA CTGGGCCACC TGCCCCTGCT GGAGGGGCAC CATGTGTGAG
1601 CCGCCCTACT CCCTTCACCT GGCCCTCTGT TCCTGCCCCA GCCCCTTCCC
1651 CAGACCCCTC TCCAGTCTCC TGCACCCCTT AGCCCTCCCT GCTTTGCCTG
1701 GCCCGTTGAA GTTCCAGGGA GCTTGCCCGG GTCTCCTCGG GGGAGCAGAT
1751 GAGGGCCCTG CCCCCGCCCC ACTGACTTCC TCCAATAAAG TCATGTCTGC
1801 CCCCAAAAAA AAAAAAAAAA AAAAAAAAAA AAAAAAAAAA AAAAAAAAAA
1851 AAAAAAAAAA AAAAAAA (SEQ ID NO:1)
```

FIGURE 1A

FEATURES:
5'UTR:        1-15
Start Codon:  16
Stop Codon:   1597
3'UTR:        1600

Homologous proteins:
Top 10 BLAST Hits

|  | Score | E |
|---|---|---|
| gi\|4220888\|gb\|AAD12719.1\| (AF078798) extracellular signal-regul... | 690 | 0.0 |
| gi\|1730893\|sp\|Q11179\|YPC2_CAEEL PUTATIVE SERINE/THREONINE-PROTE... | 379 | e-104 |
| gi\|1362216\|pir\|\|A56492 protein kinase ERK2 (EC 2.7.1.-) - slime... | 335 | 7e-91 |
| gi\|10046831\|emb\|CAC07956.1\| (AJ293280) putative mitogen-activat... | 331 | 1e-89 |
| gi\|7291043\|gb\|AAF46481.1\| (AE003446) CG2309 gene product [Droso... | 326 | 4e-88 |
| gi\|2146861\|pir\|\|JC5153 mitogen-activated protein kinase (EC 2.7... | 301 | 2e-80 |
| gi\|1360110\|emb\|CAA57972.1\| (X82646) mitogen-activated protein k... | 301 | 2e-80 |
| gi\|1262446\|gb\|AAC47170.1\| (U36377) mitogen-activated protein ki... | 301 | 2e-80 |
| gi\|2131000\|emb\|CAB09307.1\| (Z95887) MAP-kinase homologue [Leish... | 290 | 3e-77 |
| gi\|1169550\|sp\|P42525\|ERK1_DICDI EXTRACELLULAR SIGNAL-REGULATED ... | 266 | 4e-70 |

BLAST to dbEST:

|  | Score | E |
|---|---|---|
| gi\|9903390 /dataset=dbest /taxon=960... | 710 | 0.0 |
| gi\|9510335 /dataset=dbest /taxon=9606... | 607 | e-171 |
| gi\|5657230 /dataset=dbest /taxon=9606 ... | 323 | 7e-86 |

EXPRESSION INFORMATION FOR MODULATORY USE:
library source:
Expression information from BLAST dbEST hits:
gi\|9903390 Larynx epithelium
gi\|9510335 Kidney, Wilms' tumor
gi\|5657230 Pancreas, adenocarcinoma Expression information from PCR-based tissue screening panels:
Fetal whole brain
Hippocampus

FIGURE 1B

```
  1 MCTVVDPRIV RRYLLRRQLG QGAYGIVWKA VDRRTGEVVA IKKIFDAFRD
 51 KTDAQRTFRE ITLLQEFGDH PNIISLLDVI RAENDRDIYL VFEFMDTDLN
101 AVIRKGGLLQ DVHVRSIFYQ LLRATRFLHS GHVVHRDQKP SNVLLDANCT
151 VKLCDFGLAR SLGDLPEGPE DQAVTEYVAT RWYRAPEVLL SSHRYTLGVD
201 MWSLGCILGE MLRGRPLFPG KSTLHQLELI LETIPPPSEE AHRPRQTLDA
251 LLPPDTSPEA LDLLRRLLVF APDKRLSATQ ALQHPYVQRF HCPSDEWARE
301 ADVRPRAHEG VQLSVPEYRS RVYQMILECG GSSGTSREKG PEGVSPSQAH
351 LHKPRADPQL PSRTPVQGPR PRPQSSPGHD PAEHESPRAA KNVPRQNSAP
401 LLQTALLENG ERPPGAKEAP PLTLSLVKPS GRGAAPSLTS QAAAQVANQA
451 LIRGDWNRGG GVRVASVQQV PPRLPPEARP GRRMFSTSAL QGAQGGARAL
501 LGGYSQAYGT VCHSALGHLP LLEGHHV (SEQ ID NO:2)
```

FEATURES:
Functional domains and key regions:
[1] PDOC00001 PS00001 ASN_GLYCOSYLATION
N-glycosylation site 148-151 NCTV

[2] PDOC00004 PS00004 CAMP_PHOSPHO_SITE
cAMP- and cGMP-dependent protein kinase phosphorylation site 274-277 KRLS

[3] PDOC00005 PS00005 PKC_PHOSPHO_SITE
Protein kinase C phosphorylation site

Number of matches: 6
   1     57-59 TFR
   2    150-152 TVK
   3    192-194 SHR
   4    335-337 TSR
   5    386-388 SPR
   6    430-432 SGR

[4] PDOC00006 PS00006 CK2_PHOSPHO_SITE
Casein kinase II phosphorylation site

Number of matches: 7
   1      3-6 TVVD
   2     57-60 TFRE
   3     75-78 SLLD
   4    161-164 SLGD
   5    256-259 TSPE

FIGURE 2A

```
    6    314-317  SVPE
    7    335-338  TSRE
```

[5] PDOC00007 PS00007 TYR_PHOSPHO_SITE
Tyrosine kinase phosphorylation site

```
        81-89  RAENDRDIY
```

[6] PDOC00008 PS00008 MYRISTYL
N-myristoylation site

Number of matches: 10
```
    1    157-162  GLARSL
    2    205-210  GCILGE
    3    310-315  GVQLSV
    4    330-335  GGSSGT
    5    331-336  GSSGTS
    6    343-348  GVSPSQ
    7    433-438  GAAPSL
    8    461-466  GVRVAS
    9    492-497  GAQGGA
   10    495-500  GGARAL
```

[7] PDOC00009 PS00009 AMIDATION
Amidation site

```
        480-483  PGRR
```

[8] PDOC00016 PS00016 RGD
Cell attachment sequence

```
        453-455  RGD
```

[9] PDOC00100 PS00107 PROTEIN_KINASE_ATP
Protein kinases ATP-binding region signature

```
        19-43  LGQGAYGIVWKAVDRRTGEVVAIKK
```

[10] PDOC01049 PS01351 MAPK
MAP kinase signature

```
        48-149
FRDKTDAQRTFREITLLQEFGDHPNIISLLDVIRAENDRDIYLVFEFMDTDLNAVIRKGGLLQDVHVRSIFYQLLRATR
FLHSGHVVHRDQKPSNVLLDANC
```

FIGURE 2B

Membrane spanning structure and domains:
```
 Helix Begin  End  Score Certainty
   1    505   525  0.610 Putative
```

BLAST Alignment to Top Hit:
>gi|4220888|gb|AAD12719.1| (AF078798) extracellular signal-regulated
        kinase 7; ERK7 [Rattus norvegicus]
        Length = 546

Score = 690 bits (1762), Expect = 0.0
Identities = 372/552 (67%), Positives = 408/552 (73%), Gaps = 28/552 (5%)
Frame = +1

```
Query:   16  MCTV-VDPRIVRRYLLRRQLGQGAYGIVWKAVDRRTGEVVAIKKIFDAFRDKTDAQRTFR  192
             MC   VD + +RYL++R+LG+GAYGIVWKA+DRRTGEVVAIKKIFDAFRD+TDAQRTFR
Sbjct:    1  MCAAEVDRHVSQRYLIKRRLGKGAYGIVWKAMDRRTGEVVAIKKIFDAFRDQTDAQRTFR   60

Query:  193  EITLLQEFGDHPNIISLLDVIRAENDRDIYLVFEFMDTDLNAVIRKGGLLQDVHVRSIFY  372
             EI LL+EFG HPNII LLDVI A+NDRDIYLVFE MDTDLNAVI+KG LL+D+H R IFY
Sbjct:   61  EIMLLREFGGHPNIIRLLDVIPAKNDRDIYLVFESMDTDLNAVIQKGRLLEDIHKRCIFY  120

Query:  373  QLLRATRFLHSGHVVHRDQKPSNVLLDANCTVKLCDFGLARSLGDLPEGPEDQAVTEYVA  552
             QLLRAT+F+HSG V+HRDQKP+NVLLDA C VKLCDFGLARSL D PEG   QA+TEYVA
Sbjct:  121  QLLRATKFIHSGRVIHRDQKPANVLLDAACRVKLCDFGLARSLSDFPEG-LGQALTEYVA  179

Query:  553  TRWYRAPEVLLSSHRYTLGVDMWSLGCILGEMLRGRPLFPGKSTLHQLELILETIPPPSE  732
             TRWYRAPEVLLSS  YT GVDMWSLGCILGEMLRG+PLFPG ST HQLELILETIP PS
Sbjct:  180  TRWYRAPEVLLSSRWYTPGVDMWSLGCILGEMLRGQPLFPGTSTFHQLELILETIPLPSM  239

Query:  733  E----------------AHRPRQTLDALLPPDTSPEALDLLRRLLVFAPDKRLSATQAL  861
             E               RPRQTLDALLPPDT PEALDLL+RLL FAPDKRLSA QAL
Sbjct:  240  EELQGLGSDYSALILQNLGSRPRQTLDALLPPDTPPEALDLLKRLLAFAPDKRLSAEQAL  299

Query:  862  QHPYVQRFHCPSDEWAREADVRPRAHEGVQLSVPEYRSRVYQMILECGGSSGTSREKGPE 1041
             QHPYVQRFHCP  EW R +DVR   HEG QLS PEYR+R+YQMILE  +S + RE+
Sbjct:  300  QHPYVQRFHCPDREWTRGSDVRLPVHEGDQLSAPEYRNRLYQMILERRRNSRSPREE-DL  358

Query: 1042  GVSPSQAHLH-------KPRADPQLPSRTPVQGPRPRPQSSPGHDPAEHESPRAAKNVPR 1200
             GV  S+A L        KP  PQ+ + TP +   P+PQ+ GHDP E       V R
Sbjct:  359  GVVASRAELRASQRQSLKPGVLPQVLAETPARKRGPKPQNGHGHDPEHVE-------VRR  411

Query: 1201  QNSAPLLQTALLENGERPPGAKEAPPLTLSLVKPSGRGAAPSLTSQAAAQVANQALIRGD 1380
             Q+S PL Q   +GERPPGA  PP   S VK R APSLTSQAAAQ ANQ LIR D
Sbjct:  412  QSSDPLYQLPPPGSGERPPGATGEPPSAPSGVKTHVRAVAPSLTSQAAAQAANQPLIRSD  471
```

FIGURE 2C

```
Query: 1381 WNRGGGVRVASVQQVPPRLP---PEARPGRRMFSTSALQGAQGGARALLGGYSQAYGTVC 1551
             RGGG R    ++VP RLP   PE RPGRRMF S QGAQG ARA LGGYSQAYGTVC
Sbjct:  472 PARGGGPRAVGARRVPSRLPREAPEPRPGRRMFGISVSQGAQGAARAALGGYSQAYGTVC 531

Query: 1552 HSALGHLPLLEG 1587
             SALG LPLL G
Sbjct:  532 RSALGRLPLLPG 543 (SEQ ID NO:4)

>gi|1730893|sp|Q11179|YPC2_CAEEL PUTATIVE SERINE/THREONINE-PROTEIN
           KINASE C05D10.2 IN CHROMOSOME III
  gb|AAA20987.1| (U13645) similar to protein kinases [Caenorhabditis elegans]
           Length = 474

Score =  379 bits (963), Expect = e-104
Identities = 195/348 (56%), Positives = 249/348 (71%), Gaps = 24/348 (6%)
Frame = +1

Query:   28 VDPRIVRRYLLRRQLGQGAYGIVWKAVDRRTGEVVAIKKIFDAFRDKTDAQRTFREITLL 207
            VD  I  ++ L+++LG+GAYGIVWKA D+R+ E VA+KKIFDAFR+ TD+QRTFRE+  L
Sbjct:    5 VDTHIHEKFDLQKRLGKGAYGIVWKAYDKRSRETVALKKIFDAFRNPTDSQRTFREVMFL 64

Query:  208 QEFGDHPNIISLLDVIRAENDR----DIYLVFEFMDTDLNAVIRKGGLLQDVHVRSIFYQ 375
            QEFG HPN+I L ++ RA+NDR    DIYL FEFM+ DL+ VI+KG +L+DVH + I Q
Sbjct:   65 QEFGKHPNVIKLYNIFRADNDRVIRRDIYLAFEFMEADLHNVIKKGSILKDVHKQYIMCQ 124

Query:  376 LLRATRFLHSGHVVHRDQKPSNVLLDANCTVKLCDFGLARSLG---DLPEGPEDQAVTEY 546
            L RA RFLHSG+V+HRD KPSNVLLDA+C VKL DFGLARSL    D PEG +  +TEY
Sbjct:  125 LFRAIRFLHSGNVLHRDLKPSNVLLDADCRVKLADFGLARSLSSLEDYPEGQKMPDLTEY 184

Query:  547 VATRWYRAPEVLLSSHRYTLGVDMWSLGCILGEMLRGRPLFPGKSTLHQLELILETIPPP 726
            VATRWYR+PE+LL++  RYT GVDMWSLGCIL EML GR LFPG ST++Q+E I+ TI P
Sbjct:  185 VATRWYRSPEILLAAKRYTKGVDMWSLGCILAEMLIGRALFPGSSTINQIERIMNTIAKP 244

Query:  727 S----------------EEAHRPRQTLDALLPPDTSPEALDLLRRLLVFAPDKRLSATQ 855
            S                   RPR+ LD L+    A+D+++RLL+FAP KRL+ Q
Sbjct:  245 SRADIASIGSHYAASVLEKMPQRPRKPLD-LIITQSQTAAIDMVQRLLIFAPQKRLTVEQ 303

Query:  856 ALQHPYVQRFHCPSDEWAREADVRPRAHEGVQLSVPEYRSRVYQMILE 999
            L HPYV +FH PS+E    +V P  + +QLS+ +YR R+Y+MI E
Sbjct:  304 CLVHPYVVQFHNPSEEPVLNYEVYPPLPDHIQLSIDDYRDRLYEMIDE 351 (SEQ ID NO:5)
```

FIGURE 2D

>gi|1362216|pir||A56492 protein kinase ERK2 (EC 2.7.1.-) - slime mold
    (Dictyostelium discoideum)
      Length = 369

Score =  335 bits (851), Expect = 7e-91
 Identities = 170/343 (49%), Positives = 239/343 (69%), Gaps = 19/343 (5%)
 Frame = +1

Query: 28    VDPRIVRRYLLRRQLGQGAYGIVWKAVDRRTGEVVAIKKIFDAFRDKTDAQRTFREITLL  207
             +D  ++R+Y +  ++G+GAYGIVW+A+D++     VA+KKIFDAF++ TDAQRTFREI L
Sbjct: 6     IDKHVLRKYEVFHKIGKGAYGIVWEAIDKKPHHTVALKKIFDAFQNATDAQRTFREIMFL  65

Query: 208   QEFGDHPNIISLLDVIRAENDRDIYLVFEFMDTDLNAVIRKGGLLQDVHVRSIFYQLLRA  387
             QE   H NII LL+VI+A+NDRDIYLVFE M+TDL+AVIR   +L+++H +    YQLL+A
Sbjct: 66    QELHGHENIIKLLNVIKADNDRDIYLVFEHMETDLHAVIR-AKILEEIHKQYTIYQLLKA  124

Query: 388   TRFLHSGHVVHRDQKPSNVLLDANCTVKLCDFGLARSLGDLPEGPE-DQAVTEYVATRWY  564
             ++ +HS +V+HRD KPSN+LL++ C VK+ DFGLARS+  L   E +  +TEYVATRWY
Sbjct: 125   LKYMHSANVLHRDIKPSNLLLNSECLVKVADFGLARSITSLESIAEANPVLTEYVATRWY  184

Query: 565   RAPEVLLSSHRYTLGVDMWSLGCILGEMLRGRPLFPGKSTLHQLELILETIPPPSEE---  735
             RAPE+LL S +YT GVDMWS+GCILGE+L  + +FPG ST++QL+LI+E    PS E
Sbjct: 185   RAPEILLGSTKYTKGVDMWSIGCILGELLGEKAMFPGNSTMNQLDLIIEVTGRPSAEDIE  244

Query: 736   ---------------AHRPRQTLDALLPPDTSPEALDLLRRLLVFAPDKRLSATQALQHP  870
                            PR  D + P S +ALDLL++L  F PDKR++A +AL HP
Sbjct: 245   AIKSPFAGTMLESLPPSNPRSLSD--MYPSASVDALDLLKKLSQFNPDKRITAEEALAHP  302

Query: 871   YVQRFHCPSDEWAREADVRPRAHEGVQLSVPEYRSRVYQMILE                  999
             +V +FH P++E   +   +G +  + EYR+R+Y I++
Sbjct: 303   FVTQFHNPAEEPHFDRIIKISIDDGQKFPIAEYRNRLYNDIIK  345 (SEQ ID NO:6)

>gi|10046831|emb|CAC07956.1| (AJ293280) putative mitogen-activated
    protein kinase 2 [Leishmania mexicana]
      Length = 458

Score =  331 bits (840), Expect = 1e-89
 Identities = 168/343 (48%), Positives = 230/343 (66%), Gaps = 17/343 (4%)
 Frame = +1

Query: 16    MCTVVDPRIVRRYLLRRQLGQGAYGIVWKAVDRRTGEVVAIKKIFDAFRDKTDAQRTFRE  195
             M   ++  I+++Y ++ QLGQGAYGIVW+A++R+     VVA+KKI+DAF++ TDAQRTFRE
Sbjct: 1     MSAEIESHILKKYEIQTQLGQGAYGIVWRALERKHNRVVALKKIYDAFQNSTDAQRTFRE  60

FIGURE 2E

```
Query: 196  ITLLQEFGDHPNIISLLDVIRAENDRDIYLVFEFMDTDLNAVIRKGGLLQDVHVRSIFYQ 375
            I L   HPNII LL V RA NDRDIYLVFE+M+TDL+ VIR   +L+ +H + I YQ
Sbjct: 61   IMFLHRL-HHPNIIRLLHVHRAFNDRDIYLVFEYMETDLHVVIR-ANILEGIHKQFIIYQ 118

Query: 376  LLRATRFLHSGHVVHRDQKPSNVLLDANCTVKLCDFGLARSLGDLP-EGPEDQAVTEYVA 552
            LL+  +FLHS ++HRD KPSN+L+++CT+K+ DFGLARS+   L  E     +T+Y+A
Sbjct: 119  LLKTMKFLHSAEILHRDMKPSNLLVNSDCTMKVADFGLARSILSLEGEQASRPVLTDYIA 178

Query: 553  TRWYRAPEVLLSSHRYTLGVDMWSLGCILGEMLRGRPLFPGKSTLHQLELILETIPPPS- 729
            TRWYR PE+LL S RYT GVDMWS+GCILGE++ G+P+FPG+ST +QLELI      PS
Sbjct: 179  TRWYRPPEILLGSTRYTKGVDMWSVGCILGELMLGKPMFPGRSTTNQLELICSVTGMPSA 238

Query: 730  ---------------EEAHRPRQTLDALLPPDTSPEALDLLRRLLVFAPDKRLSATQALQ 864
                           + H +   A L P S +AL+L+ RL+ F P++RLSA +AL+
Sbjct: 239  ADVAATNSQFANAMLRDIHCAHRRTFAELLPSASADALNLIERLMCFNPNRRLSAAEALE 298

Query: 865  HPYVQRFHCPSDEWAREADVRPRAHEGVQLSVPEYRSRVYQMI 993
            HPYV  FH P DE        +    +L + +YR +Y+ I
Sbjct: 299  HPYVAAFHRPDDEPVAPEPITVSLPDSQRLPLAKYRDAIYEQI 341 (SEQ ID NO:7)

>gi|7291043|gb|AAF46481.1| (AE003446) CG2309 gene product [Drosophila
         melanogaster]
         Length = 392

Score =  326 bits (828), Expect = 4e-88
 Identities = 160/343 (46%), Positives = 234/343 (67%), Gaps = 21/343 (6%)
 Frame = +1

Query: 28   VDPRIVRRYLLRRQLGQGAYGIVWKAVDRRTGEVVAIKKIFDAFRDKTDAQRTFREITLL 207
            +D +   + +R+++G+GAYGIVWKA DRRT   VA+KK+FDAFRD+TDAQRT+RE+  L
Sbjct: 17   LDQTVESIFDVRKRMGKGAYGIVWKATDRRTKNTVALKKVFDAFRDETDAQRTYREVIFL 76

Query: 208  QEFGDHPNIISLLDVIRAENDRDIYLVFEFMDTDLNAVIRKGGLLQDVHVRSIFYQLLRA 387
            + F  HPNI+ L+D+ +A N+ D YLVFEFM++DL+ VI++G +L+DVH R + YQL+ A
Sbjct: 77   RAFRCHPNIVRLVDIFKASNNLDFYLVFEFMESDLHNVIKRGNVLKDVHKRFVMYQLINA 136

Query: 388  TRFLHSGHVVHRDQKPSNVLLDANCTVKLCDFGLARSLGD---LPEGPEDQAVTEYVATR 558
            +F+HSG+V+HRD KPSN+L+D+ C +K+ DFGLAR+L       +D +T+YVATR
Sbjct: 137  IKFIHSGNVIHRDLKPSNILIDSKCRLKVADFGLARTLSSRRIYDDLEQDGMLTDYVATR 196

Query: 559  WYRAPEVLLSSHRYTLGVDMWSLGCILGEMLRGRPLFPGKSTLHQLELILETIPPP---- 726
            WYRAPE+L++S  YT G+DMW LGCILGEM+R +PLF G ST++Q+E I+ ++P
Sbjct: 197  WYRAPEILVASRNYTKGIDMWGLGCILGEMIRQKPLFQGTSTVNQIEKIVTSLPNVTKLD 256
```

FIGURE 2F

```
Query: 727   --------------SEEAHRPRQ-TLDALLPPDTSPEALDLLRRLLVFAPDKRLSATQALQ 864
                           S   R R+ +LD ++   +   + + L++ LLV  P  RL+A +A++
Sbjct: 257   IASIGPSFGSVLLSRNIQRDRRYSLDEMM-KNCCDDGISLVKALLVLNPHNRLTAKEAIR 315

Query: 865   HPYVQRFHCPSDEWAREADVRPRAHEGVQLSVPEYRSRVYQMI 993
             HPYV RF   S E     DV P    + V+  V +YR+ +Y++I
Sbjct: 316   HPYVSRFQYASAEMDLHMDVVPPLKDHVRYDVDQYRNSLYELI 358 (SEQ ID NO:8)
```

>gi|2146861|pir||JC5153 mitogen-activated protein kinase (EC 2.7.1.-)
    - Plasmodium falciparum
    Length = 826

Score = 301 bits (762), Expect = 2e-80
Identities = 157/340 (46%), Positives = 226/340 (66%), Gaps = 17/340 (5%)
Frame = +1

```
Query: 28    VDPRIVRRYLLRRQLGQGAYGIVWKAVDRRTGEVVAIKKIFDAFRDKTDAQRTFREITLL 207
             +D    ++++Y +  +++G+GAYG+V+K   ++   +VA+KKIF AF++  TDAQRTFREI  L
Sbjct: 15    IDENVLKKYDILKKVGKGAYGVVFKGRCKKNKNIVAVKKIFGAFQNCTDAQRTFREIIFL 74

Query: 208   QEFGDHPNIISLLDVIRAENDRDIYLVFEFMDTDLNAVIRKGGLLQDVHVRSIFYQLLRA 387
               E   H NII L+DVI+A+ND DIYL+F+FM+TDL+  VI K   LL+++H + I YQLLRA
Sbjct: 75    YELNGHDNIIKLMDVIKAKNDNDIYLIFDFMETDLHEVI-KADLLEEIHKKYIIYQLLRA 133

Query: 388   TRFLHSGHVVHRDQKPSNVLLDANCTVKLCDFGLARSLGDLPEGPEDQAVTEYVATRWYR 567
             +++HSG +++HRD KPSN+L+++ C +K+  DFGLARS+        +  +T+YVATRWYR
Sbjct: 134   LKYIHSGGLLHRDIKPSNILVNSECHIKVADFGLARSISTHVNENKVPILTDYVATRWYR 193

Query: 568   APEVLLSSHRYTLGVDMWSLGCILGEMLRGRPLFPGKSTLHQLELILETIPPPS----EE 735
             APE+LL S  YT  VDMWSLGCI+GE+L G+PLF G ST++QLE I++  I  P+     E+
Sbjct: 194   APEILLGSTHYTEDVDMWSLGCIMGELLCGKPLFTGNSTMNQLEKIIQVIGKPNKKDIED 253

Query: 736   AHRP------------RQTLDALLPPDTSPEALDLLRRLLVFAPDKRLSATQALQHPYV 876
               P                  ++ L  +    S E+LDLL  +LL  F P KR+SA  AL+H YV
Sbjct: 254   IRSPFAEKIISSFVDLKKKNLKDICYK-ASNESLDLLEKLLQFNPSKRISAENALKHKYV 312

Query: 877   QRFHCPSDEWAREADVRPRAHEGVQLSVPEYRSRVYQMIL 996
             + FH   DE     +    ++ + V  YR+ VY  +I+
Sbjct: 313   EEFHSIIDEPTCRHIITIPINDNTKYRVNFYRNVVYFVIM 352 (SEQ ID NO:9)
```

FIGURE 2G

>gi|1360110|emb|CAA57972.1| (X82646) mitogen-activated protein kinase
    1, serine/threonine protein kinase [Plasmodium
    falciparum]
    Length = 826

Score = 301 bits (762), Expect = 2e-80
Identities = 157/340 (46%), Positives = 226/340 (66%), Gaps = 17/340 (5%)
Frame = +1

Query: 28   VDPRIVRRYLLRRQLGQGAYGIVWKAVDRRTGEVVAIKKIFDAFRDKTDAQRTFREITLL 207
            +D  ++++Y + +++G+GAYG+V+K  ++  +VA+KKIF AF++ TDAQRTFREI  L
Sbjct: 15   IDENVLKKYDILKKVGKGAYGVVFKGRCKKNKNIVAVKKIFGAFQNCTDAQRTFREIIFL 74

Query: 208  QEFGDHPNIISLLDVIRAENDRDIYLVFEFMDTDLNAVIRKGGLLQDVHVRSIFYQLLRA 387
            +E  H NII L+DVI+A+ND DIYL+F+FM+TDL+ VI K  LL+++H + I YQLLRA
Sbjct: 75   YELNGHDNIIKLMDVIKAKNDNDIYLIFDFMETDLHEVI-KADLLEEIHKKYIIYQLLRA 133

Query: 388  TRFLHSGHVVHRDQKPSNVLLDANCTVKLCDFGLARSLGDLPEGPEDQAVTEYVATRWYR 567
            ++++HSG ++HRD KPSN+L+++ C +K+ DFGLARS+       + +T+YVATRWYR
Sbjct: 134  LKYIHSGGLLHRDIKPSNILVNSECHIKVADFGLARSISTHVNENKVPILTDYVATRWYR 193

Query: 568  APEVLLSSHRYTLGVDMWSLGCILGEMLRGRPLFPGKSTLHQLELILETIPPPS----EE 735
            APE+LL S  YT VDMWSLGCI+GE+L G+PLF G ST++QLE I++ I P+    E+
Sbjct: 194  APEILLGSTHYTEDVDMWSLGCIMGELLCGKPLFTGNSTMNQLEKIIQVIGKPNKKDIED 253

Query: 736  AHRP-------------RQTLDALLPPDTSPEALDLLRRLLVFAPDKRLSATQALQHPYV 876
             P           ++ L +    S E+LDLL +LL F P KR+SA  AL+H YV
Sbjct: 254  IRSPFAEKIISSFVDLKKKNLKDICYK-ASNESLDLLEKLLQFNPSKRISAENALKHKYV 312

Query: 877  QRFHCPSDEWAREADVRPRAHEGVQLSVPEYRSRVYQMIL 996
            + FH  DE   +  ++ + V YR+ VY +I+
Sbjct: 313  EEFHSIIDEPTCRHIITIPINDNTKYRVNFYRNVVYFVIM 352 (SEQ ID NO:10)

>gi|1262446|gb|AAC47170.1| (U36377) mitogen-activated protein
    kinase-related protein [Plasmodium falciparum]
    Length = 765

Score = 301 bits (762), Expect = 2e-80
Identities = 157/340 (46%), Positives = 226/340 (66%), Gaps = 17/340 (5%)
Frame = +1

Query: 28   VDPRIVRRYLLRRQLGQGAYGIVWKAVDRRTGEVVAIKKIFDAFRDKTDAQRTFREITLL 207
            +D  ++++Y + +++G+GAYG+V+K  ++  +VA+KKIF AF++ TDAQRTFREI  L
Sbjct: 15   IDENVLKKYDILKKVGKGAYGVVFKGRCKKNKNIVAVKKIFGAFQNCTDAQRTFREIIFL 74

FIGURE 2H

```
Query: 208  QEFGDHPNIISLLDVIRAENDRDIYLVFEFMDTDLNAVIRKGGLLQDVHVRSIFYQLLRA 387
            E  H NII L+DVI+A+ND DIYL+F+FM+TDL+ VI K  LL+++H + I YQLLRA
Sbjct: 75   YELNGHDNIIKLMDVIKAKNDNDIYLIFDFMETDLHEVI-KADLLEEIHKKYIIYQLLRA 133

Query: 388  TRFLHSGHVVHRDQKPSNVLLDANCTVKLCDFGLARSLGDLPEGPEDQAVTEYVATRWYR 567
            +++HSG ++HRD KPSN+L+++ C +K+ DFGLARS+         +  +T+YVATRWYR
Sbjct: 134  LKYIHSGGLLHRDIKPSNILVNSECHIKVADFGLARSISTHVNENKVPILTDYVATRWYR 193

Query: 568  APEVLLSSHRYTLGVDMWSLGCILGEMLRGRPLFPGKSTLHQLELILETIPPPS----EE 735
            APE+LL S  YT VDMWSLGCI+GE+L G+PLF G ST++QLE I++ I  P+     E+
Sbjct: 194  APEILLGSTHYTEDVDMWSLGCIMGELLCGKPLFTGNSTMNQLEKIIQVIGKPNKKDIED 253

Query: 736  AHRP-------------RQTLDALLPPDTSPEALDLLRRLLVFAPDKRLSATQALQHPYV 876
            P            ++ L +    S E+LDLL +LL F P KR+SA  AL+H YV
Sbjct: 254  IRSPFAEKIISSFVDLKKKNLKDICYK-ASNESLDLLEKLLQFNPSKRISAENALKHKYV 312

Query: 877  QRFHCPSDEWAREADVRPRAHEGVQLSVPEYRSRVYQMIL 996
            + FH  DE      ++  +  V  YR+ VY +I+
Sbjct: 313  EEFHSIIDEPTCRHIITIPINDNTKYRVNFYRNVVYFVIM 352 (SEQ ID NO:11)

>gi|2131000|emb|CAB09307.1| (Z95887) MAP-kinase homologue
            [Leishmania mexicana]
            Length = 358

Score = 290 bits (735), Expect = 3e-77
Identities = 149/306 (48%), Positives = 206/306 (66%), Gaps = 20/306 (6%)
Frame = +1

Query: 28   VDPRIVRRYLLRRQLGQGAYGIVWKAVDRRTGEVVAIKKIFDAFRDKTDAQRTFREITLL 207
            +D + +RY + R +G GAYG+VW A+DRRTG+ VA+KK++DAF + DAQRT+RE+ LL
Sbjct: 6    IDGEVEQRYRILRHIGSGAYGVVWCALDRRTGKCVALKKVYDAFGNVQDAQRTYREVMLL 65

Query: 208  QEFGDHPNIISLLDVIRAENDRDIYLVFEFMDTDLNAVIRKGGLLQDVHVRSIFYQLLRA 387
            Q   +P I+  +LDVIRA ND D+YLVFE ++TDL A+IRK  LLQ  H R + YQLLR
Sbjct: 66   QRLRHNPFIVGILDVIRAANDIDLYLVFELIETDLTAIIRK-NLLQRDHKRFLTYQLLRT 124

Query: 388  TRFLHSGHVVHRDQKPSNVLLDANCTVKLCDFGLARSL-GDLPEGPEDQAVTEYVATRWY 564
            LH+ +++HRD KP+NV + ++C++KL DFGLAR+          E   +T+Y+ATRWY
Sbjct: 125  VAQLHAQNIIHRDLKPANVFVSSDCSIKLGDFGLARTFRSGYDNEQEFLDLTDYIATRWY 184

Query: 565  RAPEVLLSSHRYTLGVDMWSLGCILGEMLRGRPLFPGKSTLHQLELILETIPPPSE---- 732
            R+PE+L+ S  Y+  +DMW++GC++GEML GRPLF G++TL QL LI+E I  PS+
Sbjct: 185  RSPEILVKSRAYSTAMDMWAIGCVIGEMLLGRPLFEGRNTLDQLRLIIEAIGVPSDADVR 244
```

FIGURE 2I

```
Query: 733 EAHRPRQTLDALLPPDTSP---------------EALDLLRRLLVFAPDKRLSATQALQH 867
            H P   L+ L+     +P                EA DL+ +L+VF P +RLSA +ALQH
Sbjct: 245 SLHSPE--LEKLINSLPTPLIFSPLVGNKNLKDSEATDLMMKLIVFNPKRRLSAVEALQH 302

Query: 868 PYVQRF 885
           PYV  F
Sbjct: 303 PYVAPF 308(SEQ ID NO:12)

>gi|1169550|sp|P42525|ERK1_DICDI EXTRACELLULAR SIGNAL-REGULATED
          KINASE 1 (ERK1) (MAP KINASE 1)
 gb|AAA59387.1| (U11077) extracellular signal-regulated protein kinase
          [Dictyostelium discoideum]
          Length = 415

Score = 266 bits (674), Expect = 4e-70
Identities = 142/309 (45%), Positives = 195/309 (62%), Gaps = 21/309 (6%)
Frame = +1

Query: 40  IVRRYLLRRQLGQGAYGIVWKAVDRRTGEVVAIKKIFDAFRDKTDAQRTFREITLLQEFG 219
           + RRY + +  +G GAYG+V   A D  TGE VAIKKI  AF +  D +RT REI LL+ F
Sbjct: 27  VPRRYSIVKCIGHGAYGVVCSAKDNLTGEKVAIKKISKAFDNLKDTKRTLREIHLLRHF- 85

Query: 220 DHPNIISLLDVIRA---ENDRDIYLVFEFMDTDLNAVIRKGGLLQDVHVRSIFYQLLRAT 390
           H N+IS+ D+++     E    D+Y+V E MDTDL+ +I     L D H +   YQ+LR
Sbjct: 86  KHENLISIKDILKPNSKEQFEDVYIVSELMDTDLHQIITSPQPLSDDHCQYFVYQMLRGL 145

Query: 391 RFLHSGHVVHRDQKPSNVLLDANCTVKLCDFGLARSLGDLPEGPEDQAVTEYVATRWYRA 570
           + +HS +V+HRD KPSN+L++  +C +K+CD GLAR    + +     +TEYVATRWYRA
Sbjct: 146 KHIHSANVLHRDLKPSNLLINEDCLLKICDLGLAR----VEDATHQGFMTEYVATRWYRA 201

Query: 571 PEVLLSSHRYTLGVDMWSLGCILGEMLRGRPLFPGKSTLHQLELILETIPPPSEE----- 735
           PEV+LS ++YT +D+WS+GCI  E+L  +PLF GK  +HQ+ LI+ETI   PSEE
Sbjct: 202 PEVILSWNKYTKAIDIWSVGCIFAELLGRKPLFQGKDYIHQITLIIETIGSPSEEDICNI 261

Query: 736 -AHRPRQTLDAL------------LPPDTSPEALDLLRRLLVFAPDKRLSATQALQHPYV 876
            + RQ + +L              + P  +P+A+DLL R+L F P KRL+ +AL HPY
Sbjct: 262 ANEQARQFIRSLNMGNQPKVNFANMFPKANPDAIDLLERMLYFDPSKRLTVEEALAHPYF 321

Query: 877 QRFHCPSDE 903
           Q H PSDE
Sbjct: 322 QSLHDPSDE 330 (SEQ ID NO:13)
```

FIGURE 2J

>gi|4220888|gb|AAD12719.1| (AF078798) extracellular signal-regulated
          kinase 7; ERK7 [Rattus norvegicus]
          Length = 546

Score =  690 bits (1762), Expect = 0.0
Identities = 372/552 (67%), Positives = 408/552 (73%), Gaps = 28/552 (5%)
Frame = +1

```
Query: 16    MCTV-VDPRIVRRYLLRRQLGQGAYGIVWKAVDRRTGEVVAIKKIFDAFRDKTDAQRTFR 192
             MC   VD  + +RYL++R+LG+GAYGIVWKA+DRRTGEVVAIKKIFDAFRD+TDAQRTFR
Sbjct: 1     MCAAEVDRHVSQRYLIKRRLGKGAYGIVWKAMDRRTGEVVAIKKIFDAFRDQTDAQRTFR 60

Query: 193   EITLLQEFGDHPNIISLLDVIRAENDRDIYLVFEFMDTDLNAVIRKGGLLQDVHVRSIFY 372
             EI LL+EFG HPNII LLDVI A+NDRDIYLVFE MDTDLNAVI+KG LL+D+H R IFY
Sbjct: 61    EIMLLREFGGHPNIIRLLDVIPAKNDRDIYLVFESMDTDLNAVIQKGRLLEDIHKRCIFY 120

Query: 373   QLLRATRFLHSGHVVHRDQKPSNVLLDANCTVKLCDFGLARSLGDLPEGPEDQAVTEYVA 552
             QLLRAT+F+HSG V+HRDQKP+NVLLDA C VKLCDFGLARSL D PEG   QA+TEYVA
Sbjct: 121   QLLRATKFIHSGRVIHRDQKPANVLLDAACRVKLCDFGLARSLSDFPEG-LGQALTEYVA 179

Query: 553   TRWYRAPEVLLSSHRYTLGVDMWSLGCILGEMLRGRPLFPGKSTLHQLELILETIPPPSE 732
             TRWYRAPEVLLSS  YT GVDMWSLGCILGEMLRG+PLFPG ST HQLELILETIP PS
Sbjct: 180   TRWYRAPEVLLSSRWYTPGVDMWSLGCILGEMLRGQPLFPGTSTFHQLELILETIPLPSM 239

Query: 733   E----------------AHRPRQTLDALLPPDTSPEALDLLRRLLVFAPDKRLSATQAL 861
             E                 RPRQTLDALLPPDT PEALDLL+RLL FAPDKRLSA QAL
Sbjct: 240   EELQGLGSDYSALILQNLGSRPRQTLDALLPPDTPPEALDLLKRLLAFAPDKRLSAEQAL 299

Query: 862   QHPYVQRFHCPSDEWAREADVRPRAHEGVQLSVPEYRSRVYQMILECGGSSGTSREKGPE 1041
             QHPYVQRFHCP  EW R  +DVR   HEG QLS PEYR+R+YQMILE   +S + RE+
Sbjct: 300   QHPYVQRFHCPDREWTRGSDVRLPVHEGDQLSAPEYRNRLYQMILERRRNSRSPREE-DL 358

Query: 1042  GVSPSQAHLH-------KPRADPQLPSRTPVQGPRPRPQSSPGHDPAEHESPRAAKNVPR 1200
             GV  S+A L        KP   PQ+ + TP +   P+PQ+  GHDP E      V R
Sbjct: 359   GVVASRAELRASQRQSLKPGVLPQVLAETPARKRGPKPQNGHGHDPEHVE-------VRR 411

Query: 1201  QNSAPLLQTALLENGERPPGAKEAPPLTLSLVKPSGRGAAPSLTSQAAAQVANQALIRGD 1380
             Q+S PL Q   +GERPPGA   PP  S VK    R APSLTSQAAAQ ANQ LIR D
Sbjct: 412   QSSDPLYQLPPPGSGERPPGATGEPPSAPSGVKTHVRAVAPSLTSQAAAQAANQPLIRSD 471

Query: 1381  WNRGGGVRVASVQQVPPRLP----PEARPGRRMFSTSALQGAQGGARALLGGYSQAYGTVC 1551
               RGGG R    ++VP RLP    PE RPGRRMF  S QGA+G ARA LGGYSQAYGTVC
Sbjct: 472   PARGGGPRAVGARRVPSRLPREAPEPRPGRRMFGISVSQGAQGAARAALGGYSQAYGTVC 531
```

FIGURE 2K

```
Query: 1552 HSALGHLPLLEG 1587
             SALG LPLL G
Sbjct: 532  RSALGRLPLLPG 543 (SEQ ID NO:14)

>gi|1730893|sp|Q11179|YPC2_CAEEL PUTATIVE SERINE/THREONINE-PROTEIN
        KINASE C05D10.2 IN CHROMOSOME III
  gb|AAA20987.1| (U13645) similar to protein kinases [Caenorhabditis elegans]
        Length = 474

Score =  379 bits (963), Expect = e-104
 Identities = 195/348 (56%), Positives = 249/348 (71%), Gaps = 24/348 (6%)
 Frame = +1

Query: 28   VDPRIVRRYLLRRQLGQGAYGIVWKAVDRRTGEVVAIKKIFDAFRDKTDAQRTFREITLL 207
            VD   I  ++ L+++LG+GAYGIVWKA D+R+ E VA+KKIFDAFR+ TD+QRTFRE+  L
Sbjct: 5    VDTHIHEKFDLQKRLGKGAYGIVWKAYDKRSRETVALKKIFDAFRNPTDSQRTFREVMFL 64

Query: 208  QEFGDHPNIISLLDVIRAENDR-----DIYLVFEFMDTDLNAVIRKGGLLQDVHVRSIFYQ 375
            QEFG HPN+I L ++ RA+NDR     DIYL FEFM+ DL+ VI+KG +L+DVH + I  Q
Sbjct: 65   QEFGKHPNVIKLYNIFRADNDRVIRRDIYLAFEFMEADLHNVIKKGSILKDVHKQYIMCQ 124

Query: 376  LLRATRFLHSGHVVHRDQKPSNVLLDANCTVKLCDFGLARSLG---DLPEGPEDQAVTEY 546
            L RA RFLHSG+V+HRD KPSNVLLDA+C VKL DFGLARSL    D PEG +   +TEY
Sbjct: 125  LFRAIRFLHSGNVLHRDLKPSNVLLDADCRVKLADFGLARSLSSLEDYPEGQKMPDLTEY 184

Query: 547  VATRWYRAPEVLLSSHRYTLGVDMWSLGCILGEMLRGRPLFPGKSTLHQLELILETIPPP 726
            VATRWYR+PE+LL++ RYT GVDMWSLGCIL EML GR LFPG ST++Q+E I+ TI  P
Sbjct: 185  VATRWYRSPEILLAAKRYTKGVDMWSLGCILAEMLIGRALFPGSSTINQIERIMNTIAKP 244

Query: 727  S---------------EEAHRPRQTLDALLPPDTSPEALDLLRRLLVFAPDKRLSATQ 855
            S               +  RPR+ LD L+    +  A+D+++RLL+FAP KRL+ Q
Sbjct: 245  SRADIASIGSHYAASVLEKMPQRPRKPLD-LIITQSQTAAIDMVQRLLIFAPQKRLTVEQ 303

Query: 856  ALQHPYVQRFHCPSDEWAREADVRPRAHEGVQLSVPEYRSRVYQMILE 999
             L HPYV +FH PS+E    +V P  + +QLS+ +YR R+Y+MI E
Sbjct: 304  CLVHPYVWQFHNPSEEPVLNYEVYPPLPDHIQLSIDDYRDRLYEMIDE 351 (SEQ ID NO:15)
```

FIGURE 2L

>gi|1362216|pir||A56492 protein kinase ERK2 (EC 2.7.1.-) - slime mold
        (Dictyostelium discoideum)
        Length = 369

Score =  335 bits (851), Expect = 7e-91
 Identities = 170/343 (49%), Positives = 239/343 (69%), Gaps = 19/343 (5%)
 Frame = +1

Query: 28   VDPRIVRRYLLRRQLGQGAYGIVWKAVDRRTGEVVAIKKIFDAFRDKTDAQRTFREITLL 207
            +D  ++R+Y +  ++G+GAYGIVW+A+D++      VA+KKIFDAF++ TDAQRTFREI L
Sbjct: 6    IDKHVLRKYEVFHKIGKGAYGIVWEAIDKKPHHTVALKKIFDAFQNATDAQRTFREIMFL 65

Query: 208  QEFGDHPNIISLLDVIRAENDRDIYLVFEFMDTDLNAVIRKGGLLQDVHVRSIFYQLLRA 387
            QE  H NII LL+VI+A+NDRDIYLVFE M+TDL+AVIR   +L+++H +   YQLL+A
Sbjct: 66   QELHGHENIIKLLNVIKADNDRDIYLVFEHMETDLHAVIR-AKILEEIHKQYTIYQLLKA 124

Query: 388  TRFLHSGHVVHRDQKPSNVLLDANCTVKLCDFGLARSLGDLPEGPE-DQAVTEYVATRWY 564
            +++HS +V+HRD KPSN+LL++ C VK+ DFGLARS+  L    E +  +TEYVATRWY
Sbjct: 125  LKYMHSANVLHRDIKPSNLLLNSECLVKVADFGLARSITSLESIAEANPVLTEYVATRWY 184

Query: 565  RAPEVLLSSHRYTLGVDMWSLGCILGEMLRGRPLFPGKSTLHQLELILETIPPPSEE--- 735
            RAPE+LL S +YT GVDMWS+GCILGE+L + +FPG ST++QL+LI+E    PS E
Sbjct: 185  RAPEILLGSTKYTKGVDMWSIGCILGELLGEKAMFPGNSTMNQLDLIIEVTGRPSAEDIE 244

Query: 736  ---------------AHRPRQTLDALLPPDTSPEALDLLRRLLVFAPDKRLSATQALQHP 870
                           PR  D + P   S +ALDLL++L  F PDKR++A +AL HP
Sbjct: 245  AIKSPFAGTMLESLPPSNPRSLSD--MYPSASVDALDLLKKLSQFNPDKRITAEEALAHP 302

Query: 871  YVQRFHCPSDEWAREADVRPRAHEGVQLSVPEYRSRVYQMILE 999
            +V +FH P++E  + ++    +G +  + EYR+R+Y I++
Sbjct: 303  FVTQFHNPAEEPHFDRIIKISIDDGQKFPIAEYRNRLYNDIIK 345 (SEQ ID NO:16)

>gi|10046831|emb|CAC07956.1| (AJ293280) putative mitogen-activated
        protein kinase 2 [Leishmania mexicana]
        Length = 458

Score =  331 bits (840), Expect = 1e-89
 Identities = 168/343 (48%), Positives = 230/343 (66%), Gaps = 17/343 (4%)
 Frame = +1

Query: 16   MCTVVDPRIVRRYLLRRQLGQGAYGIVWKAVDRRTGEVVAIKKIFDAFRDKTDAQRTFRE 195
            M  ++  I+++Y ++ QLGQGAYGIVW+A++R+    VVA+KKI+DAF++ TDAQRTFRE
Sbjct: 1    MSAEIESHILKKYEIQTQLGQGAYGIVWRALERKHNRVVALKKIYDAFQNSTDAQRTFRE 60

FIGURE 2M

```
Query: 196  ITLLQEFGDHPNIISLLDVIRAENDRDIYLVFEFMDTDLNAVIRKGGLLQDVHVRSIFYQ 375
            I L    HPNII LL V RA NDRDIYLVFE+M+TDL+ VIR   +L+ +H + I YQ
Sbjct: 61   IMFLHRL-HHPNIIRLLHVHRAFNDRDIYLVFEYMETDLHVVIR-ANILEGIHKQFIIYQ 118

Query: 376  LLRATRFLHSGHVVHRDQKPSNVLLDANCTVKLCDFGLARSLGDLP-EGPEDQAVTEYVA 552
            LL+  +FLHS ++HRD KPSN+L++++CT+K+ DFGLARS+  L E       +T+Y+A
Sbjct: 119  LLKTMKFLHSAEILHRDMKPSNLLVNSDCTMKVADFGLARSILSLEGEQASRPVLTDYIA 178

Query: 553  TRWYRAPEVLLSSHRYTLGVDMWSLGCILGEMLRGRPLFPGKSTLHQLELILETIPPPS- 729
            TRWYR PE+LL S RYT GVDMWS+GCILGE++ G+P+FPG+ST +QLELI     PS
Sbjct: 179  TRWYRPPEILLGSTRYTKGVDMWSVGCILGELMLGKPMFPGRSTTNQLELICSVTGMPSA 238

Query: 730  ---------------EEAHRPRQTLDALLPPDTSPEALDLLRRLLVFAPDKRLSATQALQ 864
                           + H +   A L P  S +AL+L+ RL+ F P++RLSA +AL+
Sbjct: 239  ADVAATNSQFANAMLRDIHCAHRRTFAELLPSASADALNLIERLMCFNPNRRLSAAEALE 298

Query: 865  HPYVQRFHCPSDEWAREADVRPRAHEGVQLSVPEYRSRVYQMI 993
            HPYV  FH P DE              +L + +YR +Y+ I
Sbjct: 299  HPYVAAFHRPDDEPVAPEPITVSLPDSQRLPLAKYRDAIYEQI 341 (SEQ ID NO:17)

>gi|7291043|gb|AAF46481.1| (AE003446) CG2309 gene product [Drosophila
            melanogaster]
          Length = 392

Score =  326 bits (828), Expect = 4e-88
 Identities = 160/343 (46%), Positives = 234/343 (67%), Gaps = 21/343 (6%)
 Frame = +1

Query: 28   VDPRIVRRYLLRRQLGQGAYGIVWKAVDRRTGEVVAIKKIFDAFRDKTDAQRTFREITLL 207
            +D +  + +R+++G+GAYGIVWKA DRRT  VA+KK+FDAFRD+TDAQRT+RE+  L
Sbjct: 17   LDQTVESIFDVRKRMGKGAYGIVWKATDRRTKNTVALKKVFDAFRDETDAQRTYREVIFL 76

Query: 208  QEFGDHPNIISLLDVIRAENDRDIYLVFEFMDTDLNAVIRKGGLLQDVHVRSIFYQLLRA 387
            + F  HPNI+ L+D+ +A N+ D YLVFEFM++DL+ VI++G +L+DVH R + YQL+ A
Sbjct: 77   RAFRCHPNIVRLVDIFKASNNLDFYLVFEFMESDLHNVIKRGNVLKDVHKRFVMYQLINA 136

Query: 388  TRFLHSGHVVHRDQKPSNVLLDANCTVKLCDFGLARSLGD---LPEGPEDQAVTEYVATR 558
            +F+HSG+V+HRD KPSN+L+D+ C +K+ DFGLAR+L        +D  +T+YVATR
Sbjct: 137  IKFIHSGNVIHRDLKPSNILIDSKCRLKVADFGLARTLSSRRIYDDLEQDGMLTDYVATR 196

Query: 559  WYRAPEVLLSSHRYTLGVDMWSLGCILGEMLRGRPLFPGKSTLHQLELILETIPPP---- 726
            WYRAPE+L++S  YT G+DMW LGCILGEM+R +PLF G ST++Q+E I+  ++P
Sbjct: 197  WYRAPEILVASRNYTKGIDMWGLGCILGEMIRQKPLFQGTSTVNQIEKIVTSLPNVTKLD 256
```

FIGURE 2N

```
Query:  727 ------------SEEAHRPRQ-TLDALLPPDTSPEALDLLRRLLVFAPDKRLSATQALQ 864
                         S   R R+ +LD ++   +   + + L++ LLV  P  RL+A +A++
Sbjct:  257 IASIGPSFGSVLLSRNIQRDRRYSLDEMM-KNCCDDGISLVKALLVLNPHNRLTAKEAIR 315

Query:  865 HPYVQRFHCPSDEWAREADVRPRAHEGVQLSVPEYRSRVYQMI 993
            HPYV RF   S E    DV P    + V+  V +YR+ +Y++I
Sbjct:  316 HPYVSRFQYASAEMDLHMDVVPPLKDHVRYDVDQYRNSLYELI 358 (SEQ ID NO:18)

>gi|2146861|pir||JC5153 mitogen-activated protein kinase (EC 2.7.1.-)
            - Plasmodium falciparum
          Length = 826

Score =  301 bits (762), Expect = 2e-80
 Identities = 157/340 (46%), Positives = 226/340 (66%), Gaps = 17/340 (5%)
 Frame = +1

Query:   28 VDPRIVRRYLLRRQLGQGAYGIVWKAVDRRTGEVVAIKKIFDAFRDKTDAQRTFREITLL 207
            +D  ++++Y + +++G+GAYG+V+K     ++    +VA+KKIF AF++  TDAQRTFREI  L
Sbjct:   15 IDENVLKKYDILKKVGKGAYGVVFKGRCKKNKNIVAVKKIFGAFQNCTDAQRTFREIIFL 74

Query:  208 QEFGDHPNIISLLDVIRAENDRDIYLVFEFMDTDLNAVIRKGGLLQDMHVRSIFYQLLRA 387
            E   H NII L+DVI+A+ND DIYL+F+FM+TDL+  VI K   LL+++H + I YQLLRA
Sbjct:   75 YELNGHDNIIKLMDVIKAKNDNDIYLIFDFMETDLHEVI-KADLLEEIHKKYIIYQLLRA 133

Query:  388 TRFLHSGHVVHRDQKPSNVLLDANCTVKLCDFGLARSLGDLPEGPEDQAVTEYVATRWYR 567
            +++HSG ++HRD KPSN+L+++  C +K+ DFGLARS+        +  +T+YVATRWYR
Sbjct:  134 LKYIHSGGLLHRDIKPSNILVNSECHIKVADFGLARSISTHVNENKVPILTDYVATRWYR 193

Query:  568 APEVLLSSHRYTLGVDMWSLGCILGEMLRGRPLFPGKSTLHQLELILETIPPPS----EE 735
            APE+LL S  YT VDMWSLGCI+GE+L G+PLF G ST++QLE I++  I   P+     E+
Sbjct:  194 APEILLGSTHYTEDVDMWSLGCIMGELLCGKPLFTGNSTMNQLEKIIQVIGKPNKKDIED 253

Query:  736 AHRP------------RQTLDALLPPDTSPEALDLLRRLLVFAPDKRLSATQALQHPYV 876
             P            ++ L  +       S E+LDLL +LL  F P KR+SA  AL+H YV
Sbjct:  254 IRSPFAEKIISSFVDLKKKNLKDICYK-ASNESLDLLEKLLQFNPSKRISAENALKHKYV 312

Query:  877 QRFHCPSDEWAREADVRPRAHEGVQLSVPEYRSRVYQMIL 996
            + FH   DE    +    ++   + V  YR+ VY +I+
Sbjct:  313 EEFHSIIDEPTCRHIITIPINDNTKYRVNFYRNVVYFVIM 352 (SEQ ID NO:19)
```

FIGURE 20

```
>gi|1360110|emb|CAA57972.1| (X82646) mitogen-activated protein kinase
    1, serine/threonine protein kinase [Plasmodium
    falciparum]
    Length = 826

Score =  301 bits (762), Expect = 2e-80
 Identities = 157/340 (46%), Positives = 226/340 (66%), Gaps = 17/340 (5%)
 Frame = +1

Query: 28   VDPRIVRRYLLRRQLGQGAYGIVWKAVDRRTGEVVAIKKIFDAFRDKTDAQRTFREITLL 207
            +D   ++++Y +  +++G+GAYG+V+K   ++    +VA+KKIF AF++ TDAQRTFREI  L
Sbjct: 15   IDENVLKKYDILKKVGKGAYGVVFKGRCKKNKNIVAVKKIFGAFQNCTDAQRTFREIIFL 74

Query: 208  QEFGDHPNIISLLDVIRAENDRDIYLVFEFMDTDLNAVIRKGGLLQDVHVRSIFYQLLRA 387
             E   H NII L+DVI+A+ND DIYL+F+FM+TDL+  VI K    LL+++H + I YQLLRA
Sbjct: 75   YELNGHDNIIKLMDVIKAKNDNDIYLIFDFMETDLHEVI-KADLLEEIHKKYIIYQLLRA 133

Query: 388  TRFLHSGHVVHRDQKPSNVLLDANCTVKLCDFGLARSLGDLPEGPEDQAVTEYVATRWYR 567
            +++HSG ++HRD KPSN+L+++  C +K+ DFGLARS+     +    +T+YVATRWYR
Sbjct: 134  LKYIHSGGLLHRDIKPSNILVNSECHIKVADFGLARSISTHVNENKVPILTDYVATRWYR 193

Query: 568  APEVLLSSHRYTLGVDMWSLGCILGEMLRGRPLFPGKSTLHQLELILETIPPPS----EE 735
            APE+LL S  YT VDMWSLGCI+GE+L G+PLF G ST++QLE I++  I  P+     E+
Sbjct: 194  APEILLGSTHYTEDVDMWSLGCIMGELLCGKPLFTGNSTMNQLEKIIQVIGKPNKKDIED 253

Query: 736  AHRP------------RQTLDALLPPDTSPEALDLLRRLLVFAPDKRLSATQALQHPYV 876
              P          ++  L +      S E+LDLL +LL F P KR+SA  AL+H YV
Sbjct: 254  IRSPFAEKIISSFVDLKKKNLKDICYK-ASNESLDLLEKLLQFNPSKRISAENALKHKYV 312

Query: 877  QRFHCPSDEWAREADVRPRAHEGVQLSVPEYRSRVYQMIL 996
            + FH   DE   +   ++ +   V  YR+ VY +I+
Sbjct: 313  EEFHSIIDEPTCRHIITIPINDNTKYRVNFYRNVVYFVIM 352 (SEQ ID NO:20)

>gi|1262446|gb|AAC47170.1| (U36377) mitogen-activated protein
    kinase-related protein [Plasmodium falciparum]
    Length = 765

Score =  301 bits (762), Expect = 2e-80
 Identities = 157/340 (46%), Positives = 226/340 (66%), Gaps = 17/340 (5%)
 Frame = +1

Query: 28   VDPRIVRRYLLRRQLGQGAYGIVWKAVDRRTGEVVAIKKIFDAFRDKTDAQRTFREITLL 207
            +D   ++++Y +  +++G+GAYG+V+K   ++    +VA+KKIF AF++ TDAQRTFREI  L
Sbjct: 15   IDENVLKKYDILKKVGKGAYGVVFKGRCKKNKNIVAVKKIFGAFQNCTDAQRTFREIIFL 74
```

FIGURE 2P

```
Query: 208  QEFGDHPNIISLLDVIRAENDRDIYLVFEFMDTDLNAVIRKGGLLQDVHVRSIFYQLLRA 387
            E   H NII L+DVI+A+ND DIYL+F+FM+TDL+ VI K  LL+++H + I YQLLRA
Sbjct: 75   YELNGHDNIIKLMDVIKAKNDNDIYLIFDFMETDLHEVI-KADLLEEIHKKYIIYQLLRA 133

Query: 388  TRFLHSGHVVHRDQKPSNVLLDANCTVKLCDFGLARSLGDLPEGPEDQAVTEYVATRWYR 567
            +++HSG ++HRD KPSN+L+++ C +K+ DFGLARS+        +   +T+YVATRWYR
Sbjct: 134  LKYIHSGGLLHRDIKPSNILVNSECHIKVADFGLARSISTHVNENKVPILTDYVATRWYR 193

Query: 568  APEVLLSSHRYTLGVDMWSLGCILGEMLRGRPLFPGKSTLHQLELILETIPPPS----EE 735
            APE+LL S  YT VDMWSLGCI+GE+L G+PLF G ST++QLE I++ I  P+    E+
Sbjct: 194  APEILLGSTHYTEDVDMWSLGCIMGELLCGKPLFTGNSTMNQLEKIIQVIGKPNKKDIED 253

Query: 736  AHRP-------------RQTLDALLPPDTSPEALDLLRRLLVFAPDKRLSATQALQHPYV 876
             P            ++ L +       S E+LDLL +LL F P KR+SA  AL+H YV
Sbjct: 254  IRSPFAEKIISSFVDLKKKNLKDICYK-ASNESLDLLEKLLQFNPSKRISAENALKHKYV 312

Query: 877  QRFHCPSDEWAREADVRPRAHEGVQLSVPEYRSRVYQMIL 996
            + FH  DE        +   ++ +  V  YR+ VY +I+
Sbjct: 313  EEFHSIIDEPTCRHIITIPINDNTKYRVNFYRNVVYFVIM 352(SEQ ID NO:21)

>gi|2131000|emb|CAB09307.1| (Z95887) MAP-kinase homologue
    [Leishmania mexicana]
    Length = 358

Score = 290 bits (735), Expect = 3e-77
Identities = 149/306 (48%), Positives = 206/306 (66%), Gaps = 20/306 (6%)
Frame = +1

Query: 28   VDPRIVRRYLLRRQLGQGAYGIVWKAVDRRTGEVVAIKKIFDAFRDKTDAQRTFREITLL 207
            +D + +RY + R +G GAYG+VW A+DRRTG+ VA+KK++DAF +  DAQRT+RE+ LL
Sbjct: 6    IDGEVEQRYRILRHIGSGAYGVVWCALDRRTGKCVALKKVYDAFGNVQDAQRTYREVMLL 65

Query: 208  QEFGDHPNIISLLDVIRAENDRDIYLVFEFMDTDLNAVIRKGGLLQDVHVRSIFYQLLRA 387
            Q   +P I+ +LDVIRA ND D+YLVFE ++TDL A+IRK  LLQ  H R + YQLLR
Sbjct: 66   QRLRHNPFIVGILDVIRAANDIDLYLVFELIETDLTAIIRK-NLLQRDHKRFLTYQLLRT 124

Query: 388  TRFLHSGHVVHRDQKPSNVLLDANCTVKLCDFGLARSL-GDLPEGPEDQAVTEYVATRWY 564
             LH+ +++HRD KP+NV + ++C++KL DFGLAR+    E  +T+Y+ATRWY
Sbjct: 125  VAQLHAQNIIHRDLKPANVFVSSDCSIKLGDFGLARTFRSGYDNEQEFLDLTDYIATRWY 184

Query: 565  RAPEVLLSSHRYTLGVDMWSLGCILGEMLRGRPLFPGKSTLHQLELILETIPPPSE---- 732
            R+PE+L+ S Y+  +DMW++GC++GEML GRPLF G++TL QL LI+E I  PS+
Sbjct: 185  RSPEILVKSRAYSTAMDMWAIGCVIGEMLLGRPLFEGRNTLDQLRLIIEAIGVPSDADVR 244
```

FIGURE 2Q

```
Query: 733 EAHRPRQTLDALLPPDTSP---------------EALDLLRRLLVFAPDKRLSATQALQH 867
            H P    L+ L+      +P                EA DL+  +L+VF P +RLSA +ALQH
Sbjct: 245 SLHSPE--LEKLINSLPTPLIFSPLVGNKNLKDSEATDLMMKLIVFNPKRRLSAVEALQH 302

Query: 868 PYVQRF 885
            PYV  F
Sbjct: 303 PYVAPF 308 (SEQ ID NO:22)

>gi|1169550|sp|P42525|ERK1_DICDI EXTRACELLULAR SIGNAL-REGULATED
           KINASE 1 (ERK1) (MAP KINASE 1)
  gb|AAA59387.1| (U11077) extracellular signal-regulated protein kinase
           [Dictyostelium discoideum]
           Length = 415

Score =  266 bits (674), Expect = 4e-70
 Identities = 142/309 (45%), Positives = 195/309 (62%), Gaps = 21/309 (6%)
 Frame = +1

Query: 40  IVRRYLLRRQLGQGAYGIVWKAVDRRTGEVVAIKKIFDAFRDKTDAQRTFREITLLQEFG 219
           + RRY + +  +G GAYG+V  A D  TGE VAIKKI  AF + D +RT REI LL+ F
Sbjct: 27  VPRRYSIVKCIGHGAYGVVCSAKDNLTGEKVAIKKISKAFDNLKDTKRTLREIHLLRHF- 85

Query: 220 DHPNIISLLDVIRA---ENDRDIYLVFEFMDTDLNAVIRKGGLLQDMHVRSIFYQLLRAT 390
           H N+IS+ D+++     E    D+Y+V E MDTDL+ +I     L D H +   YQ+LR
Sbjct: 86  KHENLISIKDILKPNSKEQFEDVYIVSELMDTDLHQIITSPQPLSDDHCQYFVYQMLRGL 145

Query: 391 RFLHSGHVVHRDQKPSNVLLDANCTVKLCDFGLARSLGDLPEGPEDQAVTEYVATRWYRA 570
           + +HS +V+HRD KPSN+L++  +C +K+CD GLAR     + +     +TEYVATRWYRA
Sbjct: 146 KHIHSANVLHRDLKPSNLLINEDCLLKICDLGLAR----VEDATHQGFMTEYVATRWYRA 201

Query: 571 PEVLLSSHRYTLGVDMWSLGCILGEMLRGRPLFPGKSTLHQLELILETIPPPSEE----- 735
           PEV+LS ++YT +D+WS+GCI E+L +PLF GK +HQ+ LI+ETI   PSEE
Sbjct: 202 PEVILSWNKYTKAIDIWSVGCIFAELLGRKPLFQGKDYIHQITLIIETIGSPSEEDIQNI 261

Query: 736 -AHRPRQTLDAL------------LPPDTSPEALDLLRRLLVFAPDKRLSATQALQHPYV 876
            + RQ + +L            + P +P+A+DLL R+L F P KRL+  +AL HPY
Sbjct: 262 ANEQARQFIRSLNMGNQPKVNFANMFPKANPDAIDLLERMLYFDPSKRLTVEEALAHPYF 321

Query: 877 QRFHCPSDE 903
           Q H PSDE
Sbjct: 322 QSLHDPSDE 330 (SEQ ID NO:23)
```

FIGURE 2R

Hmmer search results (Pfam):

| Model | Description | Score | E-value | N |
|---|---|---|---|---|
| PF00069 | Eukaryotic protein kinase domain | 311.5 | 9.8e-90 | 1 |
| CE00022 | CE00022 MAGUK_subfamily_d | 22.1 | 2e-06 | 1 |
| CE00031 | CE00031 VEGFR | 21.3 | 1.7e-06 | 1 |
| CE00359 | E00359 bone_morphogenetic_protein_receptor | 18.5 | 0.00015 | 2 |
| CE00334 | E00334 urotrophin_receptor | 6.4 | 0.054 | 1 |
| CE00203 | CE00203 ERBB_RECEPTOR | 0.4 | 9.2 | 1 |
| CE00287 | CE00287 PTK_Eph_orphan_receptor | -30.2 | 2.7e-06 | 1 |
| CE00292 | CE00292 PTK_membrane_span | -55.5 | 8.5e-06 | 1 |
| CE00016 | CE00016 GSK_glycogen_synthase_kinase | -65.5 | 5.8e-13 | 1 |
| CE00291 | CE00291 PTK_fgf_receptor | -69.2 | 9.5e-05 | 1 |
| CE00290 | CE00290 PTK_Trk_family | -106.4 | 4.1e-08 | 1 |
| CE00286 | E00286 PTK_EGF_receptor | -117.5 | 0.00071 | 1 |
| CE00288 | CE00288 PTK_Insulin_receptor | -211.9 | 0.018 | 1 |

Parsed for domains:

| Model | Domain | seq-f | seq-t | hmm-f | hmm-t | score | E-value |
|---|---|---|---|---|---|---|---|
| CE00359 | 1/2 | 17 | 47 .. | 145 | 178 .. | 1.1 | 12 |
| CE00203 | 1/1 | 134 | 160 .. | 862 | 888 .. | 0.4 | 9.2 |
| CE00031 | 1/1 | 119 | 160 .. | 1053 | 1094 .. | 21.3 | 1.7e-06 |
| CE00334 | 1/1 | 132 | 160 .. | 676 | 704 .. | 6.4 | 0.054 |
| CE00359 | 2/2 | 133 | 222 .. | 272 | 367 .. | 16.8 | 0.00045 |
| CE00288 | 1/1 | 13 | 230 .. | 1 | 269 [] | -211.9 | 0.018 |
| CE00287 | 1/1 | 13 | 252 .. | 1 | 260 [] | -30.2 | 2.7e-06 |
| CE00292 | 1/1 | 13 | 267 .. | 1 | 288 [] | -55.5 | 8.5e-06 |
| CE00286 | 1/1 | 15 | 267 .. | 1 | 263 [] | -117.5 | 0.00071 |
| CE00290 | 1/1 | 15 | 282 .. | 1 | 282 [] | -106.4 | 4.1e-08 |
| CE00291 | 1/1 | 13 | 285 .. | 1 | 285 [] | -69.2 | 9.5e-05 |
| CE00022 | 1/1 | 120 | 285 .. | 129 | 281 .. | 22.1 | 2e-06 |
| PF00069 | 1/1 | 13 | 287 .. | 1 | 278 [] | 311.5 | 9.8e-90 |
| CE00016 | 1/1 | 1 | 349 [. | 1 | 433 [] | -65.5 | 5.8e-13 |

FIGURE 2S

```
   1 NNNNNNNNNN NNNNNNNNNN NNNNNNNNNN NNNNNNNNNN NNNNNNNNNN
  51 NNNNNNNNNN NNNNNNNNNN NNNNNNNNNN NNNNNNNNNN NNNNNNNNNN
 101 NNNNNNNNNN NNNNNNNNNN NNNNNNNNNN NNNNNNNNNN NNNNNNNNNN
 151 NNNNNNNNNN NNNNNNNNNN NNNNNNNNNN NNNNNNNNNN NNNNNNNNNN
 201 NNNNNNNNNN NNNNNNNNNN NNNNNNNNNN NNNNNNNNNN NNNNNNNNNN
 251 NNNNNNNNNN NNNNNNNNNN NNNNNNNNNN NNNNNNNNNN NNNNNNNNNN
 301 NNNNNNNNNN NNNNNNNNNN NNNNNNNNNN NNNNNNNNNN NNNNNNNNNN
 351 NNNNNNNNNN NNNNNNNNNN NNNNNNNNNN NNNNNNNNNN NNNNNNNNNN
 401 NNNNNNNNNN NNNNNNNNNN NNNNNNNNNN NNNNNNNNNN NNNNNNNNNN
 451 NNNNNNNNNN NNNNNNNNNN NNNNNNNNNN NNNNNNNNNN NNNNNNNNNN
 501 NNNNNNNNNN NNNNNNNNNN NNNNNNNNNN NNNNNNNNNN NNNNNNNNNN
 551 NNNNNNNNNN NNNNNNNNNN NNNNNNNNNN NNNNNNNNNN NNNNNNNNNN
 601 NNNNNNNNNN NNNNNNNNNN NNNNNNNNNN NNNNNNNNNN NNNNNNNNNN
 651 NNNNNNNNNN NNNNNNNNNN NNNNNNNNNN NNNNNNNNNN NNNNNNNNNN
 701 NNNNNNNNNN NNNNNNNNNN NNNNNNNNNN NNNNNNNNNN NNNNNNNNNN
 751 NNNNNNNNNN NNNNNNNNNN NNNNNNNNNN NNNNNNNNNN NNNNNNNNNN
 801 NNNNNNNNNN NNNNNNNNNN NNNNNNNNNN NNNNNNNNNN NNNNNNNNNN
 851 NNNNNNNNNN NNNNNNNNNN NNNNNNNNNN NNNNNNNNNN NNNNNNNNNN
 901 NNNNNNNNNN NNNNNNNNNN NNNNNNNNNN NNNNNNNNNN NNNNNNNNNN
 951 NNNNNNNNNN NNNNNNNNNN NNNNNNNNNN NNNNNNNNNN NNNNNNNNNN
1001 NNNNNNNNNN NNNNNNNNNN NNNNNNNNNN NNNNNNNNNN NNNNNNNNNN
1051 NNNNNNNNNN NNNNNNNNNN NNNNNNNNNN NNNNNNNNNN NNNNNNNNNN
1101 NNNNNNNNNN NNNNNNNNNN NNNNNNNNNN NNNNNNNNNN NNNNNNNNNN
1151 NNNNNNNNNN NNNNNNNNNN NNNNNNNNNN NNNNNNNNNN NNNNNNNNNN
1201 NNNNNNNNNN NNNNNNNNNN NNNNNNNNNN NNNNNNNNNN NNNNNNNNNN
1251 NNNNNNNNNN NNNNNNNNNN NNNNNNNNNN NNNNNNNNNN NNNNNNNNNN
1301 NNNNNNNNNN NNNNNNNNNN NNNNNNNNNN NNNNNNNNNN NNNNNNNNNN
1351 NNNNNNNNNN NNNNNNNNNN NNNNNNNNNN NNNNNNNNNN NNNNNNNNNN
1401 NNNNNNNNNN NNNNNNNNNN NNNNNNNNNN NNNNNNNNNN NNNNNNNNNN
1451 NNNNNNNNNN NNNNNNNNNN NNNNNNNNNN NNNNNNNNNN NNNNNNNNNN
1501 NNNNNNNNNN NNNNNNNNNN NNNNNNNNNN NNNNNNNNNN NNNNNNNNNN
1551 NNNNNNNNNN NNNNNNNNNN NNNNNNNNNN NNNNNNNNNN NNNNNNNNNN
1601 NNNNNNNNNN NNNNNNNNNN NNNNNNNNNN NNNNNNNNNN NNNNNNNNNN
1651 NNNNNNNNNN NNNNNNNNNN NNNNNNNNNN NNNNNNNNNN NNNNNNNNNN
1701 NNNNNNNNNN NNNNNNNNNN NNNNNNNNNN NNNNNNNNNN NNNNNNNNNN
1751 NNNNNNNNNN NNNNNNNNNN NNNNNNNNNN NNNNNNNNNN NNNNNNNNNN
1801 NNNNNNNNNN NNNNNNNNNN NNNNNNNNNN NNNNNNNNNN NNNNNNNNNN
1851 NNNNNNNNNN NNNNNNNNNN NNNNNNNNNN NNNNNNNNNN NNNNNNNNNN
1901 NNNNNNNNNN NNNNNNNNNN NNNNNNNNNN NNNNNNNNNN NNNNNNNNNN
1951 NNNNNNNNNN NNNNNNNNNN NNNNNNNNNN NNNNNNNNNN NNNNNNNNNN
2001 NNNNNNNNNN NNNNNNNNNN NNNNNNNNNN NNNNNNNNNN NNNNNNNNNN
2051 NNNNNNNNNN NNNNNNNNNN NNNNNNNNNN NNNNNNNNNN NNNNNNNNNN
2101 NNNNNNNNNN NNNNNNNNNN NNTTGTTCCT TTTCCTTCTT TTTTTGAATT
2151 CTTTTTGAGC AAGTAGTTTG TGTTGTGGTT GTTGTTTGAG ACAGGGTCTG
2201 GCTCTGTCAC CCAGGCTGGA GTGCAGTGGC GCAATCCAGG CTCACTGCAA
2251 CCTCTGCCTC CCGGCTCAAG CGATCCTCCT ACCTCAGCCT CCCAAGTAGC
2301 TGGGACAACA GGCTCATGTC ACCACACCCA GCTAATTTTC CTATTTTTTT
```

FIGURE 3A

```
2351 TTTTTAATAG AAATGAGGTT TTATGTTGCC GAAGCTGGTC TCCAATTCCT
2401 GAGTCATTAG CCACGCCCGG CTAATTTTTG TATTTTTAGT GGAGACGGGG
2451 TTTCACCACG TTGGCCAGGC TGGTCTTGAA CCCTTGACCT CGGGTGATCC
2501 ACCCGCCTCG GCCTCCCAGA GTGTTGGGAT TACAGGCGTG AACCACCGTG
2551 TCCCGCCCAA ATAATAATAT ACTATTAATA CTTCACATGT AACTTAAGAA
2601 CCTTACAATA CATATTCTCA TGTTATTTTG TAATAGTATA AATGTGTATT
2651 TCCATTATCC CCCTTCACTT TTTGCTATTG GTGTCATGCA TTTTACTTCT
2701 ACAAGTTATA GAGTCCACAA CAGATAGTTC TTGTTTCTAC TTTAGTCAGC
2751 TGGGCTGGGC GTGGTCCTGC GAGGAGGTGG GCGGGGCGCA CTGTGGGGCG
2801 GGGCCGGTGG GGACGTGGGC GGGGCGCCAT TGAGGGGAGG GGCCTGCGGG
2851 GAGGTTGGGT GGGCCCACTG TGGGGCGGAG CCGGGGCCTG CCGGGGGCGG
2901 GGGGTGTTGG GAGGGGCGCC CCGAGGGGCG GGGCCGGGCC GCCGTCGGTT
2951 CCCACGGCAA CCGACTCAAC AGTAAGGCCC CGCGGGCGTC CTGGCCGCCA
3001 TGTGCACCGT AGTGGACCCT CGCATTGTCC GGAGATACCT ACTCAGGCGG
3051 CAGCTCGGGC AGGGGGTGAG TGCCTGGGGG TGCGTCCGCG CGCCGAGGGG
3101 CGCGGCATAT CTGCGGATAG AGGACCTGNN NNNNNNNNNN NNNNNNNNNN
3151 NNNNNNNNNN NNNNNNNNNN NNNNNNNNNN NNNNNNNNNN NNNNNNNNNN
3201 NNNNNNNNNN NNNNNNNNNN NNNNNNNNNN NNNNNNNNNN NNNNNNNNNN
3251 NNNNNNNNNN NNNNNNNNNN NNNNNNNNNN NNNNNNNNNN NNNNNNNNNN
3301 NNNNNNNNNN NNNNNNNNNN NNNNNNNNNN NNNNNNNNNN NNNNNNNNNN
3351 NNNNNNNNNC CCGGGTCACT GAAAGAAGGG CGGACCCCAG GCTCAGGTAG
3401 CACAGGGGCG AGGCCCGAGA AGGGCCTGAG CGGTTATGGG GTGGGCGCAG
3451 AGTGAAGGGC AGAGCCTTGT GTATCTGTGT GTGTGTGTGA GCATGTAAGC
3501 CTGTGTGTGT GTGCGTGGGT GTGTGGGGGG GTGTTCGAGG GTGCCATGGG
3551 GGAGGGGAGG AAGAGCCTTC CAGGCAGTGC AGACGGTAAG TGCGTAGGCC
3601 CAGTGCAGGG TTGTGTATGT GCAACTGGAT AGGAGATGGA GAGAGACAGG
3651 TGAGTGGTGA GGGTCCGATC GTGTGGGAGC TTTGGGGAAC TTCCAAGACT
3701 TTGGTTTTTA CTGTTGCTGA GGCTGGGAGC TGTAGCAGCT GCTGGTGTCA
3751 CTTTACAAGG CCCACCCCTG TGCTGAGGAC CTACCGTGGG TGTGCACGGG
3801 AGCGGCAGAC GGAGATGAGT TAAGGGGTTA GCGTAGCCAC GCAGCGAGAG
3851 ATGCCAGAGG CTGGGACCAG GGTAGGGGCA GAAGAGACCG TGGCAGGGGC
3901 TAGATTCTGG AGGAATCTGA AGGTAGGGCC AATGGGATTG GGGGTGGATG
3951 GGGTGTGAGA GAAAGGGAGG GAGAGTGCCT GGGCAGCTGG AAGGATGATA
4001 GGGCATCCCC GAGCTTCATT TCCTGCCCAG ACGCTCCCCT CTGTGGCCTC
4051 CTTTCCTCCA GGGCCTCGCC AGCTCTCACC CTCCCTTCCC TCTACCTCCC
4101 CTCCTCTGGA AGATGTCGGA GTCTAGGGCA GCCTGCAGTT GCGGGAGCCC
4151 ACACTCCCAT CCCCTCTCGG GACCCAGGAT GGGAAGGAGG AGCCTCATGT
4201 CTGTAGGGAC AATCTGGGTG GGCAGGGGAT GGGGGAAGG GGCTGGCCCT
4251 GTGTGACGGC ACTCCTTCCC AGGCCTATGG CATTGTGTGG AAGGCAGTGG
4301 ACCGGAGGAC TGGTGAGGTC GTGGCCATCA AGAAAATCTT TGATGCTTTT
4351 AGGGATAAGA CAGATGCCCA GGTGAGTGTG TGGGGAGAAG CGTGGGAGAG
4401 GATGGGGGCA GGAAGGGGCA GCCCCTTGCC CTGGTGCCTG GAAGCTCAGG
4451 TGGGAGCTGG AGCCCAGTCA TAGCAGATGT TCTGGCCTGT CTCGGAACAC
4501 TGCCCCCTTG CCACGCCTGG TCTGGTGGGT ATTGGGTGAC AGACATCAGC
4551 TCCTTTGGGT CCTCTCAGGA CATGGGCTTC CTTCTTGCTC CACCCACCCA
4601 CACACCTGTG TTTCTGTCTC TTCAGAGAAC ATTCCGGGAA ATCACGCTCC
4651 TCCAGGTGAG TGGCCTGGGC CCTCCAGTCC AATCCCCTTG CCCAGGTACA
```

FIGURE 3B

```
4701 GATCTCTCCA GACAGGAGAG AAACTGGCCT TCTTGGGCCC CAGAGCACAG
4751 CCCCTCCTGG CCTTCCAGCC GCCTCCGACT CTCTCCCCAG GAGTTTGGGG
4801 ACCATCCCAA CATCATCAGC CTCCTTGACG TGATCCGGGC AGAGAACGAC
4851 AGGGACATTT ACCTGGTGTT TGAGTTTATG GGTGAGTGAG GCCCCGGCCA
4901 GCGCCCCAGC CCCACCTCTG TTCTGTCCTG ACGCCGTCTG CGGGTCCCTC
4951 TGCGTGTCCC TCTGCGTGTC CCTCTGCAGC TGGCCCACAG TGGCTTGCTC
5001 CCTCACCATG TACCCTGGAC TCAGGGACAG ACAGCTGACT AGTGTCAGCC
5051 TCCAGAGCCA GCAGCGACCC CTTTCGTCCC ACCTGCCCCA GGCTCCTGCT
5101 CTGACCACAG TTTGCAGTTG CGTTCTCCTT TTTCTTCTCA TTTTATGAAA
5151 CAAAGGCAAC ATGAAATAAA GTGTTAAAAC TCCTGCAGAC CTCACCGCTG
5201 TGCCCACAGG CAGTGCACAG GATGGAGGAG CGGGGCGGCC AGGCCGTGGG
5251 CTGGTTCAAA GTGGGACAGA CCTGCCAGGT GCCCCTCTCC CACTCCCCCC
5301 AGGTTGCCCC CCCAGCCCCC CACCCCCGAC TGCAGTGCGC ACCCTCTCTG
5351 CAGACACTGA CCTGAACGCA GTCATCCGGA AGGGCGGCCT GCTGCAGGAC
5401 GTCCACGTGC GCTCCATCTT CTACCAGCTC CTGCGGGCCA CCCGGTTCCT
5451 CCACTCGGGG CACGTTGTGC ACCGGGACCA GAAGGTGCGG TTCCCCCGCC
5501 CCCGCTATGC CACGTGGCCC GGCTCCCGGC CCCACCCAGC CCCGGGGCCT
5551 CAGCCTGCCT CCTCTCTGCA GCCGTCCAAT GTGCTCCTGG ATGCCAACTG
5601 CACAGTGAAG CTGTGTGACT TTGGCCTGGC CCGCTCCCTG GGCGACCTCC
5651 CTGAGGGGCC TGAGGACCAG GCCGTGACAG AGTACGTGGC CACACGCTGG
5701 TACCGAGCAC CGGAGGTGCT GCTCTCTTCG CACCGGTAAT AGCGAGACAT
5751 CCCCAACCCC CCTCCACCTC CCTGCTGCCC TCCTGCCCAG CCAGGGCTCC
5801 CAGGCCTCCC GTACTCCGAC CCTGCCTTGG TCCACAAGTG TTCCCCCATT
5851 CACCCCCCAG CAACCCCACC CCCACCTCTG CCTCTGGGTC TCTCCATGCC
5901 TACACCGCTT CCTGCCCCAG ATACACCCTT GGGGTGGACA TGTGGAGTCT
5951 GGGCTGTATC CTGGGGGAGA TGCTGCGGGG GAGACCCCTG TTCCCCGGCA
6001 CGTCCACCCT CCACCAGCTG GAGCTGATCC TGGAGACCAT CCCACCGCCA
6051 TCTGAGGAGG GTGAGCCAGG CTGCTGGGGC TGGGCACCAG GAATGCTGCA
6101 GGTCAGACAG CACAGCTGTG GGGAGACAGC AGCTGACAGG CTAGGACTGT
6151 GCTGAGAGGA GGGACGGGGA CAGGGAGGAT CCAGAGGATG GGGCAGGAGC
6201 CCCAGGAAGA CCGACTGGTG ATGGGGGCCC AGGAGGAGCT GCTGGGGGTG
6251 GGTGTGGGCA AGGCAGCACC TGGCACAGTC ACCATGAGAG CCAAGCAGTG
6301 ACCGTGAAGG GGCCAGCAGG CTGGACAAGG TCCCCAAGGG ATTCGGGTAG
6351 CAGGGGCAGG GACTGTCACT GTGCCGGGAG CTGGGGTGTG CAGAGACAGC
6401 TGGGCAGGAG AGATTCAGGT GCTGAGGGAA GAGGTGGAGG AAGGCAGTGG
6451 TAGAGGGGCC ATGGGGGTCA CTCTTGAGGG TGGGGCAAG AGGGAGCTGC
6501 ACCGCCAGGC ATAGCTGCTT GTCTGGGTGG AGCCTCCTGG GCCGTGGAGG
6551 TGGGCGCCAG CATCCACTTC TGTGAGCACA CCCCAGGGCC AGGTGCCCGA
6601 GTGTGGAGCA GGGGTCATGT GCGGGTGCTC CCGTGCACAG GCTGGGTGGC
6651 ACGCCCTGGT GATGGGGTGT TTGAGCCCCG CCAGACAGCA GAAACCCTGT
6701 AGAGAGGCTG TGCTCCCTGG GGCTGGAAGA GATGACTGGC CCCAGATGCC
6751 CTGAGCCGCC CCAGCCGACC AGGCCTGCCT GGGTCACACC ACCTTCTGCT
6801 GCCCCAGACC TCCTGGCTCT CGGCTCAGGC TGCCGTGCCT CTGTGCTGCA
6851 CCAGCTGGGG TCCCGGTGAG TGGGGGCACT TCGGTGAGGG TGACAGGGTG
6901 GCCTATCTCA AGGGAGCAGG GCCACCTTCC TGCAAGTTTA CTGGGGCCAG
6951 TTTGTACCAG TTCAGATTCT GCCTGTTTTC AAGATGGCAG TCCCAAACCC
7001 AACAACTGTT GGCCACACTG AAAGCAGGAG CCCCTCTGGT GCTCCTAGAG
```

FIGURE 3C

```
7051 GGTGGCCCAG AGGAGCTGTG CCAGGGCGTG GAGAGGAGGG CACCAGGGGG
7101 CCGCAGGGGT CTCTCCACCC TGCAGGGGCC CAGACTGCCT GCAGGTCAGG
7151 CACAGGGGCA TCTACCTAGA CAGGACAGCA GGGTGGACCC CAGTTTGGAA
7201 GCTGAGCCCC CAGCCACGAA CATGGATCTG AGGAGGGGCC CTTGGGTCGG
7251 GCCCTGGAGA CGACACACGG CAGCCCACAG GCCACGACAG ACGCTGGATG
7301 CCCTCCTACC GCCAGACACC TCCCAGAGG CCTTGGACCT CCTTAGGCGA
7351 CTCCTGGTGT TCGCCCCGGA CAAGCGGTTA AGCGCGACCC AGGCACTGCA
7401 GCACCCCTAC GTGCAGAGGT GGGGGTGGGA GAGAGTCCCC CAAGTGCGGG
7451 GGGACAGAGG TGGGGGCAGG AGAGAGCCAG CCCATGAGGG ACAGCCCCCA
7501 CAGCAGGGAC CCTGCTGTGA CGGCTTGAGG GGCTCCCTTG GCCGCAGCCC
7551 GGGCCCCACC TCCCTGGCTC CCTGCAGGTT CCACTGCCCC AGCGACGAGT
7601 GGGCACGAGA GGCAGATGTG CGGCCCCGGG CACACGAAGG GGTCCAGCTC
7651 TCTGTGCCTG AGTACCGCAG CCGCGTCTAT CAGGTGCTCC GGCTCTCGAC
7701 CCCTATCATC CCCTGTCTAC TGCACCCTGG AGGCTGCCTC CTATGTCAGA
7751 GACCCCCAAA CGCCCCATGC CCAGGCTGTG ACCTCTGAGC ACCCTTCCCC
7801 TCCCGCAGAT GATCCTGGAG TGTGGAGGCA GCAGCGGCAC CTCGAGAGAG
7851 AAGGGCCCGG AGGGTGTCTC CCCAAGCCAG GCACACCTGC ACAAACCCAG
7901 AGCCGACCCT CAGCTGCCTT CTAGGACACC TGTGCAGGGT CCCAGACCCA
7951 GGCCCCAGAG CAGCCCAGGC CATGACCCTG CCGAGCACGG TGTGTGATCT
8001 TTGCTGGCCG CCCACGCGGA GCATGGCCCG GCCCCTTCT GCCTGTGCTG
8051 CCAACTATGC GCAGCATTCG GTTCCTGACC CTGGGGTTGA CCCACTGACC
8101 CCGGGGTTGA CCCACTGACC CCACAGAGTC CCCCCGTGCA GCCAAGAACG
8151 TTCCCAGGCA GAACTCCGCT CCCCTGCTCC AAACTGCTCT CCTAGGGAAT
8201 GGGGAAAGGC CCCCTGGGGC GAAGGAAGCG CCCCCCTTGA CACTCTCGCT
8251 GGTAAGTCAT GGTGGGGCGG GCACAGGAGG GACCCCTCCT CTGCACCTTT
8301 CAGTGACCCT GTGACATGGC CCTTCCCAGG TGAAGCCAAG CGGGAGGGGA
8351 GCTGCGCCCT CCCTGACCTC CCAGGCTGCG GCTCAGGTGG CCAACCAGGC
8401 CCTGATCCGG GGTGACTGGA ACCGGGCGG TGGGGTGAGG GTGGCCAGCG
8451 TACAACAGGT AAGCCCGGCC CAGTCTGCCC CCGTCCCCTC ATCCTCCTTT
8501 CCCCTTTCCC CTTCCCCCCT GCTTTTCCCT CCCTTCCCCA TGCTTCCCAT
8551 TGCCCCTCCA ATGTCCAGTT CAAATCTCTC GAGGACCTCA AGGCCTCCCC
8601 TCCACTGCAC CCCCTCTGAT GGCCCCTTTA TGTGACCCTC AACTGTACAC
8651 AGGTCCCTCC CCGGCTTCCT CCGGAGGCCC GGCCCGGCCG GAGGATGTTC
8701 AGCACCTCTG CCTTGCAGGG TGCCCAGGGG GGTGCCAGGG CTTTGCTTGG
8751 AGGCTACTCC CAAGCCTACG GGACTGTCTG CCACTCGGCA CTGGGCCACC
8801 TGCCCCTGCT GGAGGGGCAC CATGTGTGAG CCGCCCTACT CCCTTCACCT
8851 GGCCCTCTGT TCCTGCCCCA GCCCCTTCCC CAGACCCCTC TCCAGTCTCC
8901 TGCACCCCTT AGCCCTCCCT GCTTTGCCTG GCCCGTTGAA GTTCCAGGGA
8951 GCTTGCCCGG GTCTCCTCGG GGGAGCAGAT GAGGGCCCTG CCCCCGCCCC
9001 ACTGACTTCC TCCAATAAAG TCATGTCTGC CCCCAACCTA AGCAGCCATC
9051 GTTCCTCCCC TCCCCTCTGA GGTCACAGCA TCCACTAGCT GGGGGCCCCG
9101 GCCCCTTTCC TGAAGCCTCC ACTCCTCTGA GGACCCCACC CCACCCCCGT
9151 CCTGAAACCT CCACCCCAGA GCCCAGTGCC GCCCCCTAGA GGCCCTGCCC
9201 ACTGCACATC CAGCACTGGG CTTTTCCCTC CAGGTTTGCC TGGGGCAGCT
9251 TCTTGTTCTT TGTCCATCAT TTCCTTACCT GCTGTGGCTT CAGGGTCCAG
9301 GCTGCCCCCC AGGGTGGTCC TGTGGGGTAG GGACGTAGGG TCACCCCCTG
9351 GCCATGTTTG TGACTCTGAG CCAGAGGAGA GAAGGGGAGA GAGAAGGGGG
```

FIGURE 3D

```
 9401 ACACCCCTCC CCCTGCTGTC AGGGACTGCA GCCTGCGCCC CCTAGTATGG
 9451 CCACTGCACC TGATCTGTCT TCAGGTCTCC GTAGGTGAGG GTGGGAGACA
 9501 GACATCTCGC GAGGTCAGGG TTACCTCCTC TTGTCACCCC CAGGCAAGGT
 9551 CCCTGGTGTG AGTTCAGGCC AGGGCTGTGC AGGGCTGCAA AGATCAAAGG
 9601 GGCCCTGTGG GCACAGACCT GTGTCCTAGG GTGCCAGGTG TCCTCAGCTG
 9651 CACCTGCCCA TGGGTTGGGG TTGGAACACA AGGAGGCAGC TGGAAAGCTC
 9701 ACAGGCTGGA GGAGCTCACA GTCTAAAGGG CGCGGCCTGT GCTGTCGGTG
 9751 GCGGAGTTGG GCTGCCAGGC TCACAGTCTG GGAAGCTCAT AGGCCGGAGG
 9801 AGCTCACAGT TTGAAGGGTG CGGCCTGTGC TGTGGTCGGT GTTGGGCTGC
 9851 CAGGAGAGGG GCGCTGCTGG GTTGTGGAAG CCATTGCCAC CATGGGGGAG
 9901 GGCGGGGAAG GACAAGATGT GGGTGGGGGA GCTGAGCAGA AGGTGAGAGC
 9951 TGGCGCTGCC CTGGTGCTGG ACCAGGCACC TGCAAGAGAC TCAGAAAGGG
10001 AGGCTGGGTT TGGGAGAAGG TTGGAGGAGG CGGAGGAGGG ATCGGGAGGG
10051 CCCGAGGAAG CGGTGAGCCA GTCAGAGACC CAGCCCAGGG GCTGTTTCCT
10101 GAGGGGGCTG CCGAGGGAGG TGCTTGTTGA GCTTCAAAAG CCCAAGGCGC
10151 AGGCCCAGGG TGCTGAACAA GCAGGACAGA GAGGCTGTGG GAGAGGAAGC
10201 TGCAGAGAGG CCACGGGGCT GCAGGGTTGG AGGCTTGGCC TCAGGCTGGG
10251 CAGTGTGTGG TGGGGCTGCT GAGTGGGGAA TCGCAGGTGG GCACCCAGGA
10301 GTGTGCCTGC ACAGGGGCA TCGGGGACAG GGACAGGAGA GCAGCGTGAA
10351 GTTGGGGAGG CCAAGGTGGG CCTTGGAAGT GGAGCTGGGG GGTCTTTAGT
10401 GCCCCCCACA GGGGTGGGTG GTGGGTCCAC AGGGGAAATC TGGGAGGCCA
10451 CGTGGTTAAA GGCTGCAGGA TGTAACTGGG CGATTATACA CACTGGGGAA
10501 CATGCTAGAA TACTTTGTGT GTTGTGTTTT ATTAACACCA AAATGTGCCA
10551 CATCATGGTT TAGAAGAGGT GGAGGGTGCA GGCAGGAGGC TCCGAAGGCC
10601 CAGGCAGGGC CGCCAGCCTC TGGCCTCTCC ATGGACTCCA GCTGGAGAGC
10651 CTGTCCGCTC AGCAACACCC CAGGCAGCAC CAAGAATAAC ATGCCCACAA
10701 GAACATCATG GCCAAGAGAC GCACAGGCGC ATCCCGCTTC CAGGCACCTT
10751 TCCCACCTGG CCAGAAGTCC CTGCTGTCAT CCCGACTTGC ACGGTGGTTT
10801 TGGTAACCAG TGGGCTGTGC AGGAGTGAAA GTGGGGTCAC TTTCCTTCCT
10851 TTCCCAGCTG CTGGAGTCGG AACTGCTGCC TTTGTTTGGC GGCCTTGTTT
10901 CTTAAATCAG TTCCCTCTTA GGATTTATTA CACTAAAAAA AAAATTAGTT
10951 TTTGAAAAGA AATAGGAGAA TACAGAAACA TGAATTTCAC GAGGCTATCA
11001 TCTAACAGTG GGGCTTTCT ACACACGTGG TGCCAAAATG TGTCATTCTG
11051 AGTCAATTGC AATTCCTCTC TAGGAGTGAA AAGAGATAAA AGATAAGCCA
11101 AGAACCCTGG ACAGATTCTT GGTGTTGGTG ACAAAGAGGA AAGGACCTGA
11151 GAATGGGGCT GGTGGGGAGA GGGGGGTGTC TGCTGGATAC CAGGAGGACA
11201 AGGACCACTC CCACCTGCAG GGGTGCCCAG GACCTAGTTG GGCTCGGCCT
11251 CAGCTGCACC TTGTCCCCTG CCCTCACCTG GCCCCATACC TGTCAAGGAT
11301 AAGCACTCCA CAACCAGCCC TTCTAGCGCC TGGCTTGGGC TGGGCCTGTG
11351 CAGGGGGTGC TCATGAGGCC GGGGCCACAG GTTGTCTGGA CCATGTTTTA
11401 CTGTGCTGCA AAGGCCAGTG CCCCCTCCCC ACTCTCACCC AGTGCTGGCC
11451 AGAGCCTCGC TGGAGGAGAT GGCAGACCTG GCCAAGGCGC CCCTTCGGGC
11501 TTCCCTGTGT CCCGTCCCCA GAGGCCTGCC CTGTCCAGCT TCCTTGCCAC
11551 TCCAAGGGGC ATCTTCTGGT NNNNNNNNNN NNNNNNNNNN NNNNNNNNNN
11601 NNNNNNNNNN NNNNNNNNNN NNNNNNNNNN NNNNNNNNNN NNNNNNNNNN
11651 NNNNNNNNNN NNNNNNNNNN NNNNNNNNNN NNNNNNNNNN NNNNNNNNNN
11701 NNNNNNNNNN NNNNNNNNNN NNNNNNNNNN NNNNNNNNNN NNNNNNNNNN
```

FIGURE 3E

```
11751 NNNNNNNNNN NNNNNNNNNN NNNNNNNNNN NNNNNNNNNN NNNNNNNNNN
11801 NNNNNNNNNN NNNNNNNNNN NNNNNNN (SEQ ID NO:3)
```

FEATURES:
Start:    3000
Exon:     3000-3065
Intron:   3066-4272
Exon:     4273-4371
Intron:   4372-4625
Exon:     4626-4655
Intron:   4656-4790
Exon:     4791-4881
Intron:   4882-5353
Exon:     5354-5484
Intron:   5485-5571
Exon:     5572-5735
Intron:   5736-5920
Exon:     5921-6060
Intron:   6061-7273
Exon:     7274-7418
Intron:   7419-7577
Exon:     7578-7683
Intron:   7684-7808
Exon:     7809-7989
Intron:   7990-8126
Exon:     8127-8251
Intron:   8252-8329
Exon:     8330-8458
Intron:   8459-8652
Exon:     8653-8826
Stop:     8827

CHROMOSOME MAP POSITION:
Chromosome 8

ALLELIC VARIANTS (SNPs):
DNA

| Position | Major | Minor | Domain |
|---|---|---|---|
| 2855 | T | G | Beyond ORF(5') |
| 3673 | G | T | Intron |
| 3874 | A | G | Intron |
| 4413 | A | G | Intron |
| 8475 | C | A | Intron |

Context:

FIGURE 3F

DNA
Position

2855  GCCCAAATAATAATATACTATTAATACTTCACATGTAACTTAAGAACCTTACAATACATA
TTCTCATGTTATTTTGTAATAGTATAAATGTGTATTTCCATTATCCCCCTTCACTTTTTG
CTATTGGTGTCATGCATTTTACTTCTACAAGTTATAGAGTCCACAACAGATAGTTCTTGT
TTCTACTTTAGTCAGCTGGGCTGGGCGTGGTCCTGCGAGGAGGTGGGCGGGGCGCACTGT
GGGGCGGGGCCGGTGGGACGTGGGCGGGGCGCCATTGAGGGGAGGGGCCTGCGGGGAGG
[T,G]
TGGGTGGGCCCACTGTGGGGCGGAGCCGGGGCCTGCCGGGGGCGGGGGGTGTTGGGAGGG
GCGCCCCGAGGGGCGGGGCCGGGCCGCCGTCGGTTCCCACGGCAACCGACTCAACAGTAA
GGCCCCGCGGGCGTCCTGGCCGCCATGTGCACCGTAGTGGACCCTCGCATTGTCCGGAGA
TACCTACTCAGGCGGCAGCTCGGGCAGGGGGTGAGTGCCTGGGGGTGCGTCCGCGCGCCG
AGGGGCGCGGCATATCTGCGGATAGAGGACCTG

3673  AAGAAGGGCGGACCCCCAGGCTCAGGTAGCACAGGGGCGAGGCCCGAGAAGGGCCTGAGCG
GTTATGGGGTGGGCGCAGAGTGAAGGGCAGAGCCTTGTGTATCTGTGTGTGTGTGTGAGC
ATGTAAGCCTGTGTGTGTGTGCGTGGGTGTGTGGGGGGGTGTTCGAGGGTGCCATGGGGG
AGGGGAGGAAGAGCCTTCCAGGCAGTGCAGACGGTAAGTGCGTAGGCCCAGTGCAGGGTT
GTGTATGTGCAACTGGATAGGAGATGGAGAGAGACAGGTGAGTGGTGAGGGTCCGATCGT
[G,T]
TGGGAGCTTTGGGGAACTTCCAAGACTTTGGTTTTTACTGTTGCTGAGGCTGGGAGCTGT
AGCAGCTGCTGGTGTCACTTTACAAGGCCCACCCCTGTGCTGAGGACCTACCGTGGGTGT
GCACGGGAGCGGCAGACGGAGATGAGTTAAGGGGTTAGCGTAGCCACGCAGCGAGAGATG
CCAGAGGCTGGGACCAGGGTAGGGGCAGAAGAGACCGTGGCAGGGGCTAGATTCTGGAGG
AATCTGAAGGTAGGGCCAATGGGATTGGGGGTGGATGGGGTGTGAGAGAAAGGGAGGGAG

3874  GCAGTGCAGACGGTAAGTGCGTAGGCCCAGTGCAGGGTTGTGTATGTGCAACTGGATAGG
AGATGGAGAGAGACAGGTGAGTGGTGAGGGTCCGATCGTGTGGGAGCTTTGGGGAACTTC
CAAGACTTTGGTTTTTACTGTTGCTGAGGCTGGGAGCTGTAGCAGCTGCTGGTGTCACTT
TACAAGGCCCACCCCTGTGCTGAGGACCTACCGTGGGTGTGCACGGGAGCGGCAGACGGA
GATGAGTTAAGGGGTTAGCGTAGCCACGCAGCGAGAGATGCCAGAGGCTGGGACCAGGGT
[A,G]
GGGGCAGAAGAGACCGTGGCAGGGGCTAGATTCTGGAGGAATCTGAAGGTAGGGCCAATG
GGATTGGGGGTGGATGGGGTGTGAGAGAAAGGGAGGGAGAGTGCCTGGGCAGCTGGAAGG
ATGATAGGGCATCCCCGAGCTTCATTTCCTGCCCAGACGCTCCCCTCTGTGGCCTCCTTT
CCTCCAGGGCCTCGCCAGCTCTCACCCTCCCTTCCCTCTACCTCCCCTCCTCTGGAAGAT
GTCGGAGTCTAGGGCAGCCTGCAGTTGCGGGAGCCCACACTCCCATCCCCTCTCGGGACC

4413  ATGTCGGAGTCTAGGGCAGCCTGCAGTTGCGGGAGCCCACACTCCCATCCCCTCTCGGGA
CCCAGGATGGGAAGGAGGAGCCTCATGTCTGTAGGACAATCTGGGTGGGCAGGGGATGG
GGGGAAGGGGCTGGCCCTGTGTGACGGCACTCCTTCCCAGGCCTATGGCATTGTGTGGAA
GGCAGTGGACCGGAGGACTGGTGAGGTCGTGGCCATCAAGAAAATCTTTGATGCTTTTAG
GGATAAGACAGATGCCCAGGTGAGTGTGTGGGGAGAAGCGTGGGAGAGGATGGGGGCAGG
[A,G]
AGGGGCAGCCCCTTGCCCTGGTGCCTGGAAGCTCAGGTGGGAGCTGGAGCCCAGTCATAG
CAGATGTTCTGGCCTGTCTCGGAACACTGCCCCCTTGCCACGCCTGGTCTGGTGGGTATT
GGGTGACAGACATCAGCTCCTTTGGGTCCTCTCAGGACATGGGCTTCCTTCTTGCTCCAC

FIGURE 3G

```
        CCACCCACACACCTGTGTTTCTGTCTCTTCAGAGAACATTCCGGGAAATCACGCTCCTCC
        AGGTGAGTGGCCTGGGCCCTCCAGTCCAATCCCCTTGCCCAGGTACAGATCTCTCCAGAC

8475    TGCTCCAAACTGCTCTCCTAGGGAATGGGGAAAGGCCCCCTGGGGCGAAGGAAGCGCCCC
        CCTTGACACTCTCGCTGGTAAGTCATGGTGGGGCGGGCACAGGAGGGACCCCTCCTCTGC
        ACCTTTCAGTGACCCTGTGACATGGCCCTTCCCAGGTGAAGCCAAGCGGGAGGGGAGCTG
        CGCCCTCCCTGACCTCCCAGGCTGCGGCTCAGGTGGCCAACCAGGCCCTGATCCGGGGTG
        ACTGGAACCGGGGCGGTGGGGTGAGGGTGGCCAGCGTACAACAGGTAAGCCCGGCCCAGT
        [C,A]
        TGCCCCCGTCCCCTCATCCTCCTTTCCCCTTTCCCCTTCCCCCCTGCTTTTCCCTCCCTT
        CCCCATGCTTCCCATTGCCCCTCCAATGTCCAGTTCAAATCTCTCGAGGACCTCAAGGCC
        TCCCCTCCACTGCACCCCCTCTGATGGCCCCTTTATGTGACCCTCAACTGTACACAGGTC
        CCTCCCCGGCTTCCTCCGGAGGCCCGGCCCGGCCGGAGGATGTTCAGCACCTCTGCCTTG
        CAGGGTGCCCAGGGGGGTGCCAGGGCTTTGCTTGGAGGCTACTCCCAAGCCTACGGGACT
```

FIGURE 3H

SEQUENCE LISTING

<160> NUMBER OF SEQ ID NOS: 23

<210> SEQ ID NO 1
<211> LENGTH: 1868
<212> TYPE: DNA
<213> ORGANISM: Homo sapien

<400> SEQUENCE: 1

```
ggcgtcctgg ccgccatgtg caccgtagtg gaccctcgca ttgtccggag ataccactc      60 aggcggcagc tcgggcaggg ggcctatggc attgtgtgga aggcagtgga ccggaggact     120
ggtgaggtcg tggccatcaa gaaaatcttt gatgctttta gggataagac agatgcccag     180
agaacattcc gggaaatcac gctcctccag gagtttgggg accatcccaa catcatcagc     240
ctccttgacg tgatccgggc agagaacgac agggacattt acctggtgtt tgagtttatg     300
gacactgacc tgaacgcagt catccggaag ggcggcctgc tgcaggacgt ccacgtgcgc     360
tccatcttct accagctcct gcgggccacc cggttcctcc actcggggca cgttgtgcac     420
cgggaccaga agccgtccaa tgtgctcctg gatgccaact gcacagtgaa gctgtgtgac     480
tttggcctgg cccgctccct gggcgacctc cccgagggc ctgaggacca ggccgtgaca     540
gagtacgtgg ccacacgctg gtaccgagca ccggaggtgc tgctctcttc gcaccgatac     600
acccttgggg tggacatgtg gagtctgggc tgtatcctgg gggagatgct gcggggggaga     660 cccctgttcc ccggcaagtc caccctccac cagctggagc tgatcctgga gaccatccca     720
ccgccatctg aggaggccca caggccacga cagacgctgg atgccctcct accgccagac     780
acctccccag aggccttgga cctccttagg cgactcctgg tgttcgcccc ggacaagcgg     840
ttaagcgcga cccaggcact gcagcacccc tacgtgcaga ggttccactg cccagcgac     900 gagtgggcac gagaggcaga tgtgcggccc cgggcacacg aagggtcca gctctctgtg     960 cctgagtacc gcagccgcgt ctatcagatg atcctggagt gtggaggcag cagcggcacc    1020
tcgagagaga agggcccgga gggtgtctcc ccaagccagg cacacctgca caaacccaga    1080
gccgaccctc agctgccttc taggacacct gtgcagggtc ccagacccag gccccagagc    1140
agcccaggcc atgaccctgc cgagcacgag tcccccgtg cagccaagaa cgttcccagg    1200
cagaactccg ctcccctgct ccaaactgct ctcctagaga atggggaaag gccccctggg    1260
gcgaaggaag cgcccccctt gacactctcg ctggtgaagc caagcgggag gggagctgcg    1320
ccctccctga cctcccaggc tgcggctcag gtggccaacc aggccctgat ccggggtgac    1380
tggaaccggg gcggtggggt gagggtggcc agcgtacaac aggtccctcc ccggcttcct    1440
ccggaggccc ggcccggccg gaggatgttc agcacctctg ccttgcaggg tgcccagggg    1500
ggtgccaggg ctttgcttgg aggctactcc caagcctacg ggactgtctg ccactcggca    1560
```

-continued

```
ctgggccacc tgcccctgct ggaggggcac catgtgtgag ccgccctact cccttcacct    1620
ggccctctgt tcctgcccca gcccttccc cagacccctc tccagtctcc tgcaccccctt    1680 agccctccct gctttgcctg gcccgttgaa gttccaggga gcttgcccgg gtctcctcgg    1740
gggagcagat gagggccctg cccccgcccc actgacttcc tccaataaag tcatgtctgc    1800
ccccaaaaaa aaaaaaaaaa aaaaaaaaaa aaaaaaaaaa aaaaaaaaaa aaaaaaaaaa    1860
aaaaaaaa                                                             1868
```

<210> SEQ ID NO 2
<211> LENGTH: 527
<212> TYPE: PRT
<213> ORGANISM: Homo sapien

<400> SEQUENCE: 2

```
Met Cys Thr Val Val Asp Pro Arg Ile Val Arg Arg Tyr Leu Leu Arg
 1               5                  10                  15

Arg Gln Leu Gly Gln Gly Ala Tyr Gly Ile Val Trp Lys Ala Val Asp
             20                  25                  30

Arg Arg Thr Gly Glu Val Val Ala Ile Lys Lys Ile Phe Asp Ala Phe
         35                  40                  45

Arg Asp Lys Thr Asp Ala Gln Arg Thr Phe Arg Glu Ile Thr Leu Leu
     50                  55                  60

Gln Glu Phe Gly Asp His Pro Asn Ile Ile Ser Leu Leu Asp Val Ile
 65                  70                  75                  80

Arg Ala Glu Asn Asp Arg Asp Ile Tyr Leu Val Phe Glu Phe Met Asp
                 85                  90                  95

Thr Asp Leu Asn Ala Val Ile Arg Lys Gly Gly Leu Leu Gln Asp Val
            100                 105                 110

His Val Arg Ser Ile Phe Tyr Gln Leu Leu Arg Ala Thr Arg Phe Leu
        115                 120                 125

His Ser Gly His Val Val His Arg Asp Gln Lys Pro Ser Asn Val Leu
    130                 135                 140

Leu Asp Ala Asn Cys Thr Val Lys Leu Cys Asp Phe Gly Leu Ala Arg
145                 150                 155                 160

Ser Leu Gly Asp Leu Pro Glu Gly Pro Glu Asp Gln Ala Val Thr Glu
                165                 170                 175

Tyr Val Ala Thr Arg Trp Tyr Arg Ala Pro Glu Val Leu Leu Ser Ser
            180                 185                 190

His Arg Tyr Thr Leu Gly Val Asp Met Trp Ser Leu Gly Cys Ile Leu
        195                 200                 205

Gly Glu Met Leu Arg Gly Arg Pro Leu Phe Pro Gly Lys Ser Thr Leu
    210                 215                 220

His Gln Leu Glu Leu Ile Leu Glu Thr Ile Pro Pro Ser Glu Glu
225                 230                 235                 240

Ala His Arg Pro Arg Gln Thr Leu Asp Ala Leu Leu Pro Pro Asp Thr
                245                 250                 255

Ser Pro Glu Ala Leu Asp Leu Leu Arg Arg Leu Leu Val Phe Ala Pro
            260                 265                 270

Asp Lys Arg Leu Ser Ala Thr Gln Ala Leu Gln His Pro Tyr Val Gln
        275                 280                 285

Arg Phe His Cys Pro Ser Asp Glu Trp Ala Arg Glu Ala Asp Val Arg
    290                 295                 300

Pro Arg Ala His Glu Gly Val Gln Leu Ser Val Pro Glu Tyr Arg Ser
305                 310                 315                 320
```

-continued

```
Arg Val Tyr Gln Met Ile Leu Glu Cys Gly Gly Ser Ser Gly Thr Ser
                325                 330                 335
Arg Glu Lys Gly Pro Glu Gly Val Ser Pro Ser Gln Ala His Leu His
            340                 345                 350
Lys Pro Arg Ala Asp Pro Gln Leu Pro Ser Arg Thr Pro Val Gln Gly
        355                 360                 365
Pro Arg Pro Arg Pro Gln Ser Ser Pro Gly His Asp Pro Ala Glu His
    370                 375                 380
Glu Ser Pro Arg Ala Ala Lys Asn Val Pro Arg Gln Asn Ser Ala Pro
385                 390                 395                 400
Leu Leu Gln Thr Ala Leu Leu Glu Asn Gly Glu Arg Pro Pro Gly Ala
                405                 410                 415
Lys Glu Ala Pro Pro Leu Thr Leu Ser Leu Val Lys Pro Ser Gly Arg
            420                 425                 430
Gly Ala Ala Pro Ser Leu Thr Ser Gln Ala Ala Gln Val Ala Asn
        435                 440                 445
Gln Ala Leu Ile Arg Gly Asp Trp Asn Arg Gly Gly Val Arg Val
    450                 455                 460
Ala Ser Val Gln Gln Val Pro Pro Arg Leu Pro Pro Glu Ala Arg Pro
465                 470                 475                 480
Gly Arg Arg Met Phe Ser Thr Ser Ala Leu Gln Gly Ala Gln Gly Gly
                485                 490                 495
Ala Arg Ala Leu Leu Gly Gly Tyr Ser Gln Ala Tyr Gly Thr Val Cys
            500                 505                 510
His Ser Ala Leu Gly His Leu Pro Leu Leu Glu Gly His His Val
        515                 520                 525
```

```
<210> SEQ ID NO 3
<211> LENGTH: 11827
<212> TYPE: DNA
<213> ORGANISM: Homo sapien
<220> FEATURE:
<221> NAME/KEY: misc_feature
<222> LOCATION: (1)...(11827)
<223> OTHER INFORMATION: n = A,T,C or G

<400> SEQUENCE: 3
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
```

| | |
|---|---|
| nnnnnnnnnn nnnnnnnnnn nnnnnnnnnn nnnnnnnnnn nnnnnnnnnn nnnnnnnnnn | 900 |
| nnnnnnnnnn nnnnnnnnnn nnnnnnnnnn nnnnnnnnnn nnnnnnnnnn nnnnnnnnnn | 960 |
| nnnnnnnnnn nnnnnnnnnn nnnnnnnnnn nnnnnnnnnn nnnnnnnnnn nnnnnnnnnn | 1020 |
| nnnnnnnnnn nnnnnnnnnn nnnnnnnnnn nnnnnnnnnn nnnnnnnnnn nnnnnnnnnn | 1080 |
| nnnnnnnnnn nnnnnnnnnn nnnnnnnnnn nnnnnnnnnn nnnnnnnnnn nnnnnnnnnn | 1140 |
| nnnnnnnnnn nnnnnnnnnn nnnnnnnnnn nnnnnnnnnn nnnnnnnnnn nnnnnnnnnn | 1200 |
| nnnnnnnnnn nnnnnnnnnn nnnnnnnnnn nnnnnnnnnn nnnnnnnnnn nnnnnnnnnn | 1260 |
| nnnnnnnnnn nnnnnnnnnn nnnnnnnnnn nnnnnnnnnn nnnnnnnnnn nnnnnnnnnn | 1320 |
| nnnnnnnnnn nnnnnnnnnn nnnnnnnnnn nnnnnnnnnn nnnnnnnnnn nnnnnnnnnn | 1380 |
| nnnnnnnnnn nnnnnnnnnn nnnnnnnnnn nnnnnnnnnn nnnnnnnnnn nnnnnnnnnn | 1440 |
| nnnnnnnnnn nnnnnnnnnn nnnnnnnnnn nnnnnnnnnn nnnnnnnnnn nnnnnnnnnn | 1500 |
| nnnnnnnnnn nnnnnnnnnn nnnnnnnnnn nnnnnnnnnn nnnnnnnnnn nnnnnnnnnn | 1560 |
| nnnnnnnnnn nnnnnnnnnn nnnnnnnnnn nnnnnnnnnn nnnnnnnnnn nnnnnnnnnn | 1620 |
| nnnnnnnnnn nnnnnnnnnn nnnnnnnnnn nnnnnnnnnn nnnnnnnnnn nnnnnnnnnn | 1680 |
| nnnnnnnnnn nnnnnnnnnn nnnnnnnnnn nnnnnnnnnn nnnnnnnnnn nnnnnnnnnn | 1740 |
| nnnnnnnnnn nnnnnnnnnn nnnnnnnnnn nnnnnnnnnn nnnnnnnnnn nnnnnnnnnn | 1800 |
| nnnnnnnnnn nnnnnnnnnn nnnnnnnnnn nnnnnnnnnn nnnnnnnnnn nnnnnnnnnn | 1860 |
| nnnnnnnnnn nnnnnnnnnn nnnnnnnnnn nnnnnnnnnn nnnnnnnnnn nnnnnnnnnn | 1920 |
| nnnnnnnnnn nnnnnnnnnn nnnnnnnnnn nnnnnnnnnn nnnnnnnnnn nnnnnnnnnn | 1980 |
| nnnnnnnnnn nnnnnnnnnn nnnnnnnnnn nnnnnnnnnn nnnnnnnnnn nnnnnnnnnn | 2040 |
| nnnnnnnnnn nnnnnnnnnn nnnnnnnnnn nnnnnnnnnn nnnnnnnnnn nnnnnnnnnn | 2100 |
| nnnnnnnnnn nnnnnnnnnn nnttgttcct tttccttctt tttttgaatt cttttgagc | 2160 |
| aagtagtttg tgttgtggtt gttgtttgag acagggtctg gctctgtcac ccaggctgga | 2220 |
| gtgcagtggc gcaatccagg ctcactgcaa cctctgcctc ccggctcaag cgatcctcct | 2280 |
| acctcagcct cccaagtagc tgggacaaca ggctcatgtc accacaccca gctaattttc | 2340 |
| ctatttttt tttttaatag aaatgaggtt tatgttgcc gaagctggtc tccaattcct | 2400 |
| gagtcattag ccacgcccgg ctaattttg tatttttagt ggagacgggg tttcaccacg | 2460 |
| ttggccaggc tggtcttgaa cccttgacct cgggtgatcc acccgcctcg gcctcccaga | 2520 |
| gtgttgggat tacaggcgtg aaccaccgtg tcccgcccaa ataataatat actattaata | 2580 |
| cttcacatgt aacttaagaa ccttacaata catattctca tgttattttg taatagtata | 2640 |
| aatgtgtatt tccattatcc cccttcactt tttgctattg gtgtcatgca ttttacttct | 2700 |
| acaagttata gagtccacaa cagatagttc ttgtttctac tttagtcagc tgggctgggc | 2760 |
| gtggtcctgc gaggaggtgg gcggggcgca ctgtggggcg gggccggtgg ggacgtgggc | 2820 |
| ggggcgccat tgaggggagg ggcctgcggg gaggttgggt gggcccactg tggggcggag | 2880 |
| ccggggcctg ccggggggcgg gggtgttgg gagggcgcc ccgaggggcg gggccgggcc | 2940 |
| gccgtcggtt cccacggcaa ccgactcaac agtaaggccc cgcgggcgtc ctggccgcca | 3000 |
| tgtgcaccgt agtggaccct cgcattgtcc ggagatacct actcaggcgg cagctcgggc | 3060 |
| agggggtgag tgcctggggg tgcgtccgcg cgccgagggg cgcggcatat ctgcggatag | 3120 |
| aggacctgnn nnnnnnnnnn nnnnnnnnnn nnnnnnnnnn nnnnnnnnnn nnnnnnnnnn | 3180 |
| nnnnnnnnnn nnnnnnnnnn nnnnnnnnnn nnnnnnnnnn nnnnnnnnnn nnnnnnnnnn | 3240 |

-continued

```
nnnnnnnnnn nnnnnnnnnn nnnnnnnnnn nnnnnnnnnn nnnnnnnnnn nnnnnnnnnn     3300
nnnnnnnnnn nnnnnnnnnn nnnnnnnnnn nnnnnnnnnn nnnnnnnnnn nnnnnnnnnc     3360
ccgggtcact gaaagaaggg cggaccccag gctcagtag cacagggcg aggcccgaga        3420 agggcctgag cggttatggg gtgggcgcag agtgaagggc agagccttgt gtatctgtgt     3480
gtgtgtgtga gcatgtaagc ctgtgtgtgt gtgcgtgggt gtgtgggggg gtgttcgagg     3540
gtgccatggg ggagggagg aagagccttc caggcagtgc agacggtaag tgcgtaggcc      3600
cagtgcaggg ttgtgtatgt gcaactggat aggagatgga gagagacagg tgagtggtga    3660
gggtccgatc gtgtgggagc tttggggaac ttccaagact ttggttttta ctgttgctga    3720
ggctgggagc tgtagcagct gctggtgtca ctttacaagg cccacccctg tgctgaggac    3780
ctaccgtggg tgtgcacggg agcggcagac ggagatgagt taagggggtta gcgtagccac   3840 gcagcgagag atgccagagg ctgggaccag ggtaggggca aagagaccg tggcaggggc     3900 tagattctgg aggaatctga aggtagggcc aatgggattg gggtggatg gggtgtgaga    3960 gaagggagg gagagtgcct gggcagctgg aaggatgata gggcatcccc gagcttcatt    4020
tcctgcccag acgctcccct ctgtggcctc ctttcctcca gggcctcgcc agctctcacc    4080
ctcccttccc tctacctccc ctcctctgga agatgtcgga gtctagggca gcctgcagtt    4140 gcggagccc acactcccat cccctctcgg gacccaggat gggaaggagg agcctcatgt     4200
ctgtagggac aatctgggtg ggcaggggat gggggggaagg ggctggccct gtgtgacggc   4260
actccttccc aggcctatgg cattgtgtgg aaggcagtgg accggaggac tggtgaggtc    4320
gtggccatca agaaaatctt tgatgctttt agggataaga cagatgccca ggtgagtgtg    4380
tggggagaag cgtgggagag gatggggggca ggaaggggca gccccttgcc ctggtgcctg   4440
gaagctcagg tgggagctgg agcccagtca tagcagatgt tctggcctgt ctcggaacac    4500 tgccccccttg ccacgcctgg tctggtgggt attgggtgac agacatcagc tcctttgggt   4560
cctctcagga catgggcttc cttcttgctc cacccaccca cacacctgtg tttctgtctc    4620
ttcagagaac attccgggaa atcacgctcc tccaggtgag tggcctgggc cctccagtcc    4680
aatccccttg cccaggtaca gatctctcca gacaggagag aaactggcct tcttgggccc    4740
cagagcacag cccctcctgg ccttccagcc gcctccgact ctctccccag gagtttgggg    4800
accatcccaa catcatcagc ctccttgacg tgatccgggc agagaacgac agggacattt    4860
acctggtgtt tgagtttatg ggtgagtgag gccccggcca gcgccccagc cccacctctg    4920
ttctgtcctg acgccgtctg cgggtccctc tgcgtgtccc tctgcgtgtc cctctgcagc    4980 tgcccacag tggcttgctc cctcaccatg taccctggac tcaggacag acagctgact      5040 agtgtcagcc tccagagcca gcagcgaccc ctttcgtccc acctgcccca ggctcctgct    5100
ctgaccacag tttgcagttg cgttctcctt tttcttctca ttttatgaaa caaaggcaac    5160
atgaaataaa gtgttaaaac tcctgcagac ctcaccgctg tgcccacagg cagtgcacag    5220
gatggaggag cggggcggcc aggccgtggg ctggttcaaa gtgggacaga cctgccaggt    5280
gcccctctcc cactccccccc aggttgcccc cccagccccc caccccgac tgcagtgcgc    5340 accctctctg cagacactga cctgaacgca gtcatccgga agggcggcct gctgcaggac    5400
gtccacgtgc gctccatctt ctaccagctc ctgcgggcca ccggttcct ccactcgggg     5460 cacgttgtgc accgggacca gaaggtgcgg ttccccgcc ccgctatgc cacgtggccc      5520 ggctcccggc ccacccagc ccgggggcct cagcctgcct cctctctgca gccgtccaat     5580
gtgctcctgg atgccaactg cacagtgaag ctgtgtgact ttggcctggc ccgctccctg    5640
```

```
ggcgacctcc ctgaggggcc tgaggaccag gccgtgacag agtacgtggc cacacgctgg    5700
taccgagcac cggaggtgct gctctcttcg caccggtaat agcgagacat ccccaacccc    5760
cctccacctc cctgctgccc tcctgcccag ccagggctcc caggcctccc gtactccgac    5820
cctgccttgg tccacaagtg ttcccccatt cacccccag caacccccacc cccacctctg    5880 cctctgggtc tctccatgcc tacaccgctt cctgccccag atacacccctt ggggtggaca    5940 tgtggagtct gggctgtatc ctgggggaga tgctgcgggg gagacccctg ttccccggca    6000
cgtccaccct ccaccagctg gagctgatcc tggagaccat cccaccgcca tctgaggagg    6060
gtgagccagg ctgctgggc tgggcaccag gaatgctgca ggtcagacag cacagctgtg    6120
gggagacagc agctgacagg ctaggactgt gctgagagga gggacgggga cagggaggat    6180
ccagaggatg gggcaggagc cccaggaaga ccgactggtg atgggggccc aggaggagct    6240
gctgggggtg ggtgtgggca aggcagcacc tggcacagtc accatgagag ccaagcagtg    6300
accgtgaagg ggccagcagg ctggacaagg tccccaaggg attcgggtag caggggcagg    6360
gactgtcact gtgccgggag ctgggtgtg cagagacagc tgggcaggag agattcaggt    6420
gctgagggaa gaggtggagg aaggcagtgg tagaggggcc atgggggtca ctcttgaggg    6480
tgggggcaag agggagctgc accgccaggc atagctgctt gtctgggtgg agcctcctgg    6540
gccgtggagg tgggcgccag catccacttc tgtgagcaca cccagggcc aggtgcccga    6600 gtgtggagca ggggtcatgt gcgggtgctc ccgtgcacag gctgggtggc acgccctggt    6660 gatgggtgt ttgagccccg ccagacagca gaaaccctgt agagaggctg tgctccctgg    6720
ggctggaaga gatgactggc cccagatgcc ctgagccgcc ccagccgacc aggcctgcct    6780
gggtcacacc accttctgct gccccagacc tcctggctct cggctcaggc tgccgtgcct    6840
ctgtgctgca ccagctgggg tcccggtgag tgggggcact tcggtgaggg tgacagggtg    6900
gcctatctca agggagcagg gccaccttcc tgcaagttta ctggggccag tttgtaccag    6960
ttcagattct gcctgttttc aagatggcag tcccaaaccc aacaactgtt ggccacactg    7020
aaagcaggag cccctctggt gctcctagag ggtggcccag aggagctgtg ccagggcgtg    7080
gagaggaggg caccaggggg ccgcagggt ctctccaccc tgcaggggcc cagactgcct    7140
gcaggtcagg cacaggggca tctacctaga caggacagca gggtggaccc cagtttggaa    7200
gctgagcccc cagccacgaa catggatctg aggaggggcc cttgggtcgg gccctggaga    7260
cgacacacgg cagcccacag gccacgacag acgctggatg ccctcctacc gccagacacc    7320
tccccagagg ccttggacct ccttaggcga ctcctggtgt tcgcccccgga caagcggtta    7380 agcgcgaccc aggcactgca gcaccccctac gtgcagaggt gggggtggga gagagtcccc    7440
caagtgcggg gggacagagg tgggggcagg agagagccag cccatgaggg acagccccca    7500
cagcagggac cctgctgtga cggcttgagg ggctcccttg gccgcagccc gggccccacc    7560
tccctggctc cctgcaggtt ccactgcccc agcgacgagt gggcacgaga ggcagatgtg    7620
cggccccggg cacacgaagg ggtccagctc tctgtgcctg agtaccgcag ccgcgtctat    7680
caggtgctcc ggctctcgac ccctatcatc ccctgtctac tgcaccctgg aggctgcctc    7740
ctatgtcaga gacccccaaa cgccccatgc ccaggctgtg acctctgagc acccttcccc    7800
tcccgcagat gatcctggag tgtggaggca gcagcggcac ctcgagagag aagggcccgg    7860
agggtgtctc cccaagccag gcacacctgc acaaacccag agccgaccct cagctgcctt    7920
ctaggacacc tgtgcagggt cccagaccca ggccccagag cagcccaggc catgaccctg    7980
ccgagcacgg tgtgtgatct ttgctggccg cccacgcgga gcatggcccg ggccccttct    8040
```

```
gcctgtgctg ccaactatgc gcagcattcg gttcctgacc ctggggttga cccactgacc    8100
ccggggttga cccactgacc ccacagagtc cccccgtgca gccaagaacg ttcccaggca    8160
gaactccgct cccctgctcc aaactgctct cctagggaat ggggaaaggc ccctgggc     8220
gaaggaagcg ccccccttga cactctcgct ggtaagtcat ggtggggcgg gcacaggagg   8280
gaccctcct ctgcaccttt cagtgaccct gtgacatggc ccttcccagg tgaagccaag    8340
cgggagggga gctgcgccct ccctgacctc ccaggctgcg gctcaggtgg ccaaccaggc   8400
cctgatccgg ggtgactgga accggggcgg tggggtgagg gtggccagcg tacaacaggt   8460
aagcccggcc cagtctgccc ccgtcccctc atcctccttt ccccttccc cttcccccct    8520
gcttttcct cccttcccca tgcttcccat tgcccctcca atgtccagtt caaatctctc    8580
gaggacctca aggcctcccc tccactgcac cccctctgat ggcccctta tgtgaccctc    8640
aactgtacac aggtccctcc ccggcttcct ccggaggccc ggcccggccg gaggatgttc   8700
agcacctctg ccttgcaggg tgcccagggg ggtgccaggg cttttgcttgg aggctactcc  8760
caagcctacg ggactgtctg ccactcggca ctgggccacc tgcccctgct ggaggggcac   8820
catgtgtgag ccgccctact cccttcacct ggccctctgt tcctgcccca gcccttccc    8880
cagacccctc tccagtctcc tgcaccccctt agccctccct gctttgcctg gccgttgaa   8940
gttccaggga gcttgcccgg gtcctccttgg ggagcagat gagggccctg ccccgcccc    9000
actgacttcc tccaataaag tcatgtctgc ccccaaccta agcagccatc gttcctcccc   9060
tccccctctga ggtcacagca tccactagct gggggccccg gccccttttcc tgaagcctcc 9120
actcctctga ggaccccacc ccaccccgt cctgaaacct ccaccccaga gcccagtgcc   9180
gccccctaga ggccctgccc actgcacatc cagcactggg ctttttccctc caggtttgcc  9240
tggggcagct tcttgttctt tgtccatcat ttccttacct gctgtggctt cagggtccag   9300
gctgcccccc agggtggtcc tgtggggtag ggacgtaggg tcaccccctg gccatgtttg   9360
tgactctgag ccagaggaga aaggggaga gagaaggggg acacccctcc ccctgctgtc    9420
agggactgca gcctgcgccc cctagtatgg ccactgcacc tgatctgtct tcaggtctcc   9480
gtaggtgagg gtgggagaca gacatctcgc gaggtcaggg ttacctcctc ttgtcacccc   9540
caggcaaggt ccctggtgtg agttcaggcc agggctgtgc agggctgcaa agatcaaagg   9600
ggccctgtgg gcacagacct tgtgtcctagg gtgccaggtg tcctcagctg cacctgccca   9660
tgggttgggg ttggaacaca aggaggcagc tggaaagctc acaggctgga ggagctcaca   9720
gtctaaaggg cgcggcctgt gctgtcggtg gcggagttgg gctgccaggc tcacagtctg   9780
ggaagctcat aggccggagg agctcacagt ttgaagggtg cggcctgtgc tgtggtcggt   9840
gttgggctgc caggagaggg gcgctgctgg gttgtgaag ccattgccac catgggggag    9900
ggcggggaag gacaagatgt gggtggggga gctgagcaga aggtgagagc tggcgctgcc   9960
ctggtgctga accaggcacc tgcaagagac tcagaaaggg aggctgggtt tgggagaagg   10020
ttggaggagg cggaggaggg atcgggaggg cccgaggaag cggtgagcca gtcagagacc   10080
cagcccaggg gctgtttcct gaggggctg ccgagggagg tgcttgttga gcttcaaaag    10140
cccaaggcgc aggcccaggg tgctgaacaa gcaggacaga gaggctgtgg gagaggaagc   10200
tgcagagagg ccacgggggct gcaggggttgg aggcttggcc tcaggctggg cagtgtgtgg   10260
tggggctgct gagtggggaa tcgcaggtgg gcacccagga gtgtgcctgc acaggggca    10320
tcggggacag ggacaggaga gcagcgtgaa gttggggagg ccaaggtggg ccttggaagt   10380
ggagctgggg ggtctttagt gcccccccaca ggggtgggtg gtgggtccac agggggaaatc 10440
```

-continued

```
tgggaggcca cgtggttaaa ggctgcagga tgtaactggg cgattataca cactggggaa    10500
catgctagaa tactttgtgt gttgtgtttt attaacacca aaatgtgcca catcatggtt    10560
tagaagaggt ggagggtgca ggcaggaggc tccgaaggcc caggcagggc cgccagcctc    10620
tggcctctcc atggactcca gctggagagc ctgtccgctc agcaacaccc caggcagcac    10680
caagaataac atgcccacaa gaacatcatg gccaagagac gcacaggcgc atcccgcttc    10740
caggcaccct tcccacctgg ccagaagtcc ctgctgtcat cccgacttgc acggtggttt    10800
tggtaaccag tgggctgtgc aggagtgaaa gtgggtcac  tttccttcct ttcccagctg    10860
ctggagtcgg aactgctgcc tttgtttggc ggccttgttt cttaaatcag ttccctctta    10920
ggatttatta cactaaaaaa aaaattagtt tttgaaaaga aataggagaa tacagaaaca    10980
tgaatttcac gaggctatca tctaacagtg ggggctttct acacacgtgg tgccaaaatg    11040
tgtcattctg agtcaattgc aattcctctc taggagtgaa aagagataaa agataagcca    11100
agaaccctgg acagattctt ggtgttggtg acaaagagga aaggacctga gaatgggggct   11160
ggtggggaga gggggggtgtc tgctggatac caggaggaca aggaccactc ccacctgcag    11220
gggtgcccag gacctagttg ggctcggcct cagctgcacc ttgtcccctg ccctcacctg    11280
gccccatacc tgtcaaggat aagcactcca caaccagccc ttctagcgcc tggcttgggc    11340
tgggcctgtg caggggggtgc tcatgaggcc ggggccacag gttgtctgga ccatgtttta    11400
ctgtgctgca aaggccagtg ccccctcccc actctcaccc agtgctggcc agagcctcgc    11460
tggaggagat ggcagacctg gccaaggcgc cccttcgggc ttccctgtgt cccgtcccca    11520
gaggcctgcc ctgtccagct tccttgccac tccaagggggc atcttctggt nnnnnnnnnn    11580
nnnnnnnnnn nnnnnnnnnn nnnnnnnnnn nnnnnnnnnn nnnnnnnnnn nnnnnnnnnn    11640
nnnnnnnnnn nnnnnnnnnn nnnnnnnnnn nnnnnnnnnn nnnnnnnnnn nnnnnnnnnn    11700
nnnnnnnnnn nnnnnnnnnn nnnnnnnnnn nnnnnnnnnn nnnnnnnnnn nnnnnnnnnn    11760
nnnnnnnnnn nnnnnnnnnn nnnnnnnnnn nnnnnnnnnn nnnnnnnnnn nnnnnnnnnn    11820
nnnnnnn                                                               11827
```

<210> SEQ ID NO 4
<211> LENGTH: 543
<212> TYPE: PRT
<213> ORGANISM: Rattus norvegicus

<400> SEQUENCE: 4

```
Met Cys Ala Ala Glu Val Asp Arg His Val Ser Gln Arg Tyr Leu Ile
  1               5                  10                  15

Lys Arg Arg Leu Gly Lys Gly Ala Tyr Gly Ile Val Trp Lys Ala Met
             20                  25                  30

Asp Arg Arg Thr Gly Glu Val Val Ala Ile Lys Lys Ile Phe Asp Ala
         35                  40                  45

Phe Arg Asp Gln Thr Asp Ala Gln Arg Thr Phe Arg Glu Ile Met Leu
     50                  55                  60

Leu Arg Glu Phe Gly Gly His Pro Asn Ile Ile Arg Leu Leu Asp Val
 65                  70                  75                  80

Ile Pro Ala Lys Asn Asp Arg Asp Ile Tyr Leu Val Phe Glu Ser Met
                 85                  90                  95

Asp Thr Asp Leu Asn Ala Val Ile Gln Lys Gly Arg Leu Leu Glu Asp
            100                 105                 110

Ile His Lys Arg Cys Ile Phe Tyr Gln Leu Leu Arg Ala Thr Lys Phe
        115                 120                 125
```

-continued

```
Ile His Ser Gly Arg Val Ile His Arg Asp Gln Lys Pro Ala Asn Val
130                 135                 140
Leu Leu Asp Ala Ala Cys Arg Val Lys Leu Cys Asp Phe Gly Leu Ala
145                 150                 155                 160
Arg Ser Leu Ser Asp Phe Pro Glu Gly Leu Gly Gln Ala Leu Thr Glu
                165                 170                 175
Tyr Val Ala Thr Arg Trp Tyr Arg Ala Pro Glu Val Leu Leu Ser Ser
                180                 185                 190
Arg Trp Tyr Thr Pro Gly Val Asp Met Trp Ser Leu Gly Cys Ile Leu
            195                 200                 205
Gly Glu Met Leu Arg Gly Gln Pro Leu Phe Pro Gly Thr Ser Thr Phe
210                 215                 220
His Gln Leu Glu Leu Ile Leu Glu Thr Ile Pro Leu Pro Ser Met Glu
225                 230                 235                 240
Glu Leu Gln Gly Leu Gly Ser Asp Tyr Ser Ala Leu Ile Leu Gln Asn
                245                 250                 255
Leu Gly Ser Arg Pro Arg Gln Thr Leu Asp Ala Leu Leu Pro Pro Asp
                260                 265                 270
Thr Pro Pro Glu Ala Leu Asp Leu Leu Lys Arg Leu Leu Ala Phe Ala
            275                 280                 285
Pro Asp Lys Arg Leu Ser Ala Glu Gln Ala Leu Gln His Pro Tyr Val
290                 295                 300
Gln Arg Phe His Cys Pro Asp Arg Glu Trp Thr Arg Gly Ser Asp Val
305                 310                 315                 320
Arg Leu Pro Val His Glu Gly Asp Gln Leu Ser Ala Pro Glu Tyr Arg
                325                 330                 335
Asn Arg Leu Tyr Gln Met Ile Leu Glu Arg Arg Asn Ser Arg Ser
                340                 345                 350
Pro Arg Glu Glu Asp Leu Gly Val Val Ala Ser Arg Ala Glu Leu Arg
            355                 360                 365
Ala Ser Gln Arg Gln Ser Leu Lys Pro Gly Val Leu Pro Gln Val Leu
370                 375                 380
Ala Glu Thr Pro Ala Arg Lys Arg Gly Pro Lys Pro Gln Asn Gly His
385                 390                 395                 400
Gly His Asp Pro Glu His Val Glu Val Arg Arg Gln Ser Ser Asp Pro
                405                 410                 415
Leu Tyr Gln Leu Pro Pro Gly Ser Gly Glu Arg Pro Pro Gly Ala
                420                 425                 430
Thr Gly Glu Pro Pro Ser Ala Pro Ser Gly Val Lys Thr His Val Arg
            435                 440                 445
Ala Val Ala Pro Ser Leu Thr Ser Gln Ala Ala Ala Gln Ala Ala Asn
450                 455                 460
Gln Pro Leu Ile Arg Ser Asp Pro Ala Arg Gly Gly Pro Arg Ala
465                 470                 475                 480
Val Gly Ala Arg Arg Val Pro Ser Arg Leu Pro Arg Glu Ala Pro Glu
                485                 490                 495
Pro Arg Pro Gly Arg Arg Met Phe Gly Ile Ser Val Ser Gln Gly Ala
            500                 505                 510
Gln Gly Ala Ala Arg Ala Ala Leu Gly Gly Tyr Ser Gln Ala Tyr Gly
            515                 520                 525
Thr Val Cys Arg Ser Ala Leu Gly Arg Leu Pro Leu Leu Pro Gly
530                 535                 540
```

```
<210> SEQ ID NO 5
<211> LENGTH: 347
<212> TYPE: PRT
<213> ORGANISM: Caenorhabditis elegans

<400> SEQUENCE: 5

Val Asp Thr His Ile His Glu Lys Phe Asp Leu Gln Lys Arg Leu Gly
 1               5                  10                  15

Lys Gly Ala Tyr Gly Ile Val Trp Lys Ala Tyr Asp Lys Arg Ser Arg
             20                  25                  30

Glu Thr Val Ala Leu Lys Lys Ile Phe Asp Ala Phe Arg Asn Pro Thr
         35                  40                  45

Asp Ser Gln Arg Thr Phe Arg Glu Val Met Phe Leu Gln Glu Phe Gly
     50                  55                  60

Lys His Pro Asn Val Ile Lys Leu Tyr Asn Ile Phe Arg Ala Asp Asn
 65                  70                  75                  80

Asp Arg Val Ile Arg Arg Asp Ile Tyr Leu Ala Phe Glu Phe Met Glu
                 85                  90                  95

Ala Asp Leu His Asn Val Ile Lys Lys Gly Ser Ile Leu Lys Asp Val
            100                 105                 110

His Lys Gln Tyr Ile Met Cys Gln Leu Phe Arg Ala Ile Arg Phe Leu
        115                 120                 125

His Ser Gly Asn Val Leu His Arg Asp Leu Lys Pro Ser Asn Val Leu
    130                 135                 140

Leu Asp Ala Asp Cys Arg Val Lys Leu Ala Asp Phe Gly Leu Ala Arg
145                 150                 155                 160

Ser Leu Ser Ser Leu Glu Asp Tyr Pro Glu Gly Gln Lys Met Pro Asp
                165                 170                 175

Leu Thr Glu Tyr Val Ala Thr Arg Trp Tyr Arg Ser Pro Glu Ile Leu
            180                 185                 190

Leu Ala Ala Lys Arg Tyr Thr Lys Gly Val Asp Met Trp Ser Leu Gly
        195                 200                 205

Cys Ile Leu Ala Glu Met Leu Ile Gly Arg Ala Leu Phe Pro Gly Ser
    210                 215                 220

Ser Thr Ile Asn Gln Ile Glu Arg Ile Met Asn Thr Ile Ala Lys Pro
225                 230                 235                 240

Ser Arg Ala Asp Ile Ala Ser Ile Gly Ser His Tyr Ala Ala Ser Val
                245                 250                 255

Leu Glu Lys Met Pro Gln Arg Pro Arg Lys Pro Leu Asp Leu Ile Ile
            260                 265                 270

Thr Gln Ser Gln Thr Ala Ala Ile Asp Met Val Gln Arg Leu Leu Ile
        275                 280                 285

Phe Ala Pro Gln Lys Arg Leu Thr Val Glu Gln Cys Leu Val His Pro
    290                 295                 300

Tyr Val Gln Phe His Asn Pro Ser Glu Glu Pro Val Leu Asn Tyr
305                 310                 315                 320

Glu Val Tyr Pro Pro Leu Pro Asp His Ile Gln Leu Ser Ile Asp Asp
                325                 330                 335

Tyr Arg Asp Arg Leu Tyr Glu Met Ile Asp Glu
            340                 345

<210> SEQ ID NO 6
<211> LENGTH: 340
<212> TYPE: PRT
<213> ORGANISM: Dictyostelium discoideum
```

-continued

```
<400> SEQUENCE: 6

Ile Asp Lys His Val Leu Arg Lys Tyr Glu Val Phe His Lys Ile Gly
 1               5                  10                  15

Lys Gly Ala Tyr Gly Ile Val Trp Glu Ala Ile Asp Lys Lys Pro His
            20                  25                  30

His Thr Val Ala Leu Lys Lys Ile Phe Asp Ala Phe Gln Asn Ala Thr
        35                  40                  45

Asp Ala Gln Arg Thr Phe Arg Glu Ile Met Phe Leu Gln Glu Leu His
    50                  55                  60

Gly His Glu Asn Ile Ile Lys Leu Leu Asn Val Ile Lys Ala Asp Asn
65                  70                  75                  80

Asp Arg Asp Ile Tyr Leu Val Phe Glu His Met Glu Thr Asp Leu His
                85                  90                  95

Ala Val Ile Arg Ala Lys Ile Leu Glu Glu Ile His Lys Gln Tyr Thr
            100                 105                 110

Ile Tyr Gln Leu Leu Lys Ala Leu Lys Tyr Met His Ser Ala Asn Val
        115                 120                 125

Leu His Arg Asp Ile Lys Pro Ser Asn Leu Leu Leu Asn Ser Glu Cys
130                 135                 140

Leu Val Lys Val Ala Asp Phe Gly Leu Ala Arg Ser Ile Thr Ser Leu
145                 150                 155                 160

Glu Ser Ile Ala Glu Ala Asn Pro Val Leu Thr Glu Tyr Val Ala Thr
                165                 170                 175

Arg Trp Tyr Arg Ala Pro Glu Ile Leu Leu Gly Ser Thr Lys Tyr Thr
            180                 185                 190

Lys Gly Val Asp Met Trp Ser Ile Gly Cys Ile Leu Gly Glu Leu Leu
        195                 200                 205

Gly Glu Lys Ala Met Phe Pro Gly Asn Ser Thr Met Asn Gln Leu Asp
    210                 215                 220

Leu Ile Ile Glu Val Thr Gly Arg Pro Ser Ala Glu Asp Ile Glu Ala
225                 230                 235                 240

Ile Lys Ser Pro Phe Ala Gly Thr Met Leu Glu Ser Leu Pro Pro Ser
                245                 250                 255

Asn Pro Arg Ser Leu Ser Asp Met Tyr Pro Ser Ala Ser Val Asp Ala
            260                 265                 270

Leu Asp Leu Leu Lys Lys Leu Ser Gln Phe Asn Pro Asp Lys Arg Ile
        275                 280                 285

Thr Ala Glu Glu Ala Leu Ala His Pro Phe Val Thr Gln Phe His Asn
    290                 295                 300

Pro Ala Glu Glu Pro His Phe Asp Arg Ile Ile Lys Ile Ser Ile Asp
305                 310                 315                 320

Asp Gly Gln Lys Phe Pro Ile Ala Glu Tyr Arg Asn Arg Leu Tyr Asn
                325                 330                 335

Asp Ile Ile Lys
            340

<210> SEQ ID NO 7
<211> LENGTH: 341
<212> TYPE: PRT
<213> ORGANISM: Leishmania mexicana

<400> SEQUENCE: 7

Met Ser Ala Glu Ile Glu Ser His Ile Leu Lys Lys Tyr Glu Ile Gln
 1               5                  10                  15
```

```
Thr Gln Leu Gly Gln Gly Ala Tyr Gly Ile Val Trp Arg Ala Leu Glu
             20                  25                  30

Arg Lys His Asn Arg Val Val Ala Leu Lys Lys Ile Tyr Asp Ala Phe
             35                  40                  45

Gln Asn Ser Thr Asp Ala Gln Arg Thr Phe Arg Glu Ile Met Phe Leu
 50                  55                  60

His Arg Leu His His Pro Asn Ile Ile Arg Leu Leu His Val His Arg
 65                  70                  75                  80

Ala Phe Asn Asp Arg Asp Ile Tyr Leu Val Phe Glu Tyr Met Glu Thr
             85                  90                  95

Asp Leu His Val Val Ile Arg Ala Asn Ile Leu Glu Gly Ile His Lys
            100                 105                 110

Gln Phe Ile Ile Tyr Gln Leu Leu Lys Thr Met Lys Phe Leu His Ser
            115                 120                 125

Ala Glu Ile Leu His Arg Asp Met Lys Pro Ser Asn Leu Leu Val Asn
130                 135                 140

Ser Asp Cys Thr Met Lys Val Ala Asp Phe Gly Leu Ala Arg Ser Ile
145                 150                 155                 160

Leu Ser Leu Glu Gly Glu Gln Ala Ser Arg Pro Val Leu Thr Asp Tyr
            165                 170                 175

Ile Ala Thr Arg Trp Tyr Arg Pro Glu Ile Leu Leu Gly Ser Thr
            180                 185                 190

Arg Tyr Thr Lys Gly Val Asp Met Trp Ser Val Gly Cys Ile Leu Gly
            195                 200                 205

Glu Leu Met Leu Gly Lys Pro Met Phe Pro Gly Arg Ser Thr Thr Asn
210                 215                 220

Gln Leu Glu Leu Ile Cys Ser Val Thr Gly Met Pro Ser Ala Ala Asp
225                 230                 235                 240

Val Ala Ala Thr Asn Ser Gln Phe Ala Asn Ala Met Leu Arg Asp Ile
            245                 250                 255

His Cys Ala His Arg Arg Thr Phe Ala Glu Leu Leu Pro Ser Ala Ser
            260                 265                 270

Ala Asp Ala Leu Asn Leu Ile Glu Arg Leu Met Cys Phe Asn Pro Asn
            275                 280                 285

Arg Arg Leu Ser Ala Ala Glu Ala Leu Glu His Pro Tyr Val Ala Ala
            290                 295                 300

Phe His Arg Pro Asp Asp Glu Pro Val Ala Pro Glu Pro Ile Thr Val
305                 310                 315                 320

Ser Leu Pro Asp Ser Gln Arg Leu Pro Leu Ala Lys Tyr Arg Asp Ala
            325                 330                 335

Ile Tyr Glu Gln Ile
            340

<210> SEQ ID NO 8
<211> LENGTH: 342
<212> TYPE: PRT
<213> ORGANISM: Drosophila

<400> SEQUENCE: 8

Leu Asp Gln Thr Val Glu Ser Ile Phe Asp Val Arg Lys Arg Met Gly
 1               5                  10                  15

Lys Gly Ala Tyr Gly Ile Val Trp Lys Ala Thr Asp Arg Arg Thr Lys
             20                  25                  30

Asn Thr Val Ala Leu Lys Lys Val Phe Asp Ala Phe Arg Asp Glu Thr
             35                  40                  45
```

-continued

```
Asp Ala Gln Arg Thr Tyr Arg Glu Val Ile Phe Leu Arg Ala Phe Arg
    50                  55                  60

Cys His Pro Asn Ile Val Arg Leu Val Asp Ile Phe Lys Ala Ser Asn
 65                  70                  75                  80

Asn Leu Asp Phe Tyr Leu Val Phe Glu Phe Met Glu Ser Asp Leu His
                 85                  90                  95

Asn Val Ile Lys Arg Gly Asn Val Leu Lys Asp Val His Lys Arg Phe
                100                 105                 110

Val Met Tyr Gln Leu Ile Asn Ala Ile Lys Phe Ile His Ser Gly Asn
                115                 120                 125

Val Ile His Arg Asp Leu Lys Pro Ser Asn Ile Leu Ile Asp Ser Lys
    130                 135                 140

Cys Arg Leu Lys Val Ala Asp Phe Gly Leu Ala Arg Thr Leu Ser Ser
145                 150                 155                 160

Arg Arg Ile Tyr Asp Asp Leu Glu Gln Asp Gly Met Leu Thr Asp Tyr
                165                 170                 175

Val Ala Thr Arg Trp Tyr Arg Ala Pro Glu Ile Leu Val Ala Ser Arg
                180                 185                 190

Asn Tyr Thr Lys Gly Ile Asp Met Trp Gly Leu Gly Cys Ile Leu Gly
                195                 200                 205

Glu Met Ile Arg Gln Lys Pro Leu Phe Gln Gly Thr Ser Thr Val Asn
    210                 215                 220

Gln Ile Glu Lys Ile Val Thr Ser Leu Pro Asn Val Thr Lys Leu Asp
225                 230                 235                 240

Ile Ala Ser Ile Gly Pro Ser Phe Gly Ser Val Leu Leu Ser Arg Asn
                245                 250                 255

Ile Gln Arg Asp Arg Arg Tyr Ser Leu Asp Glu Met Met Lys Asn Cys
                260                 265                 270

Cys Asp Asp Gly Ile Ser Leu Val Lys Ala Leu Leu Val Leu Asn Pro
    275                 280                 285

His Asn Arg Leu Thr Ala Lys Glu Ala Ile Arg His Pro Tyr Val Ser
    290                 295                 300

Arg Phe Gln Tyr Ala Ser Ala Glu Met Asp Leu His Met Asp Val Val
305                 310                 315                 320

Pro Pro Leu Lys Asp His Val Arg Tyr Asp Val Asp Gln Tyr Arg Asn
                325                 330                 335

Ser Leu Tyr Glu Leu Ile
            340

<210> SEQ ID NO 9
<211> LENGTH: 338
<212> TYPE: PRT
<213> ORGANISM: Plasmodium falciparum

<400> SEQUENCE: 9

Ile Asp Glu Asn Val Leu Lys Lys Tyr Asp Ile Leu Lys Lys Val Gly
  1               5                  10                  15

Lys Gly Ala Tyr Gly Val Val Phe Lys Gly Arg Cys Lys Lys Asn Lys
                 20                  25                  30

Asn Ile Val Ala Val Lys Lys Ile Phe Gly Ala Phe Gln Asn Cys Thr
             35                  40                  45

Asp Ala Gln Arg Thr Phe Arg Glu Ile Ile Phe Leu Tyr Glu Leu Asn
    50                  55                  60

Gly His Asp Asn Ile Ile Lys Leu Met Asp Val Ile Lys Ala Lys Asn
 65                  70                  75                  80
```

```
Asp Asn Asp Ile Tyr Leu Ile Phe Asp Phe Met Glu Thr Asp Leu His
                85                  90                  95
Glu Val Ile Lys Ala Asp Leu Leu Glu Ile His Lys Lys Tyr Ile
            100                 105                 110
Ile Tyr Gln Leu Leu Arg Ala Leu Lys Tyr Ile His Ser Gly Gly Leu
            115                 120                 125
Leu His Arg Asp Ile Lys Pro Ser Asn Ile Leu Val Asn Ser Glu Cys
130                 135                 140
His Ile Lys Val Ala Asp Phe Gly Leu Ala Arg Ser Ile Ser Thr His
145                 150                 155                 160
Val Asn Glu Asn Lys Val Pro Ile Leu Thr Asp Tyr Val Ala Thr Arg
                165                 170                 175
Trp Tyr Arg Ala Pro Glu Ile Leu Leu Gly Ser Thr His Tyr Thr Glu
            180                 185                 190
Asp Val Asp Met Trp Ser Leu Gly Cys Ile Met Gly Glu Leu Leu Cys
        195                 200                 205
Gly Lys Pro Leu Phe Thr Gly Asn Ser Thr Met Asn Gln Leu Glu Lys
        210                 215                 220
Ile Ile Gln Val Ile Gly Lys Pro Asn Lys Lys Asp Ile Glu Asp Ile
225                 230                 235                 240
Arg Ser Pro Phe Ala Glu Lys Ile Ile Ser Ser Phe Val Asp Leu Lys
                245                 250                 255
Lys Lys Asn Leu Lys Asp Ile Cys Tyr Lys Ala Ser Asn Glu Ser Leu
            260                 265                 270
Asp Leu Leu Glu Lys Leu Leu Gln Phe Asn Pro Ser Lys Arg Ile Ser
        275                 280                 285
Ala Glu Asn Ala Leu Lys His Lys Tyr Val Glu Glu Phe His Ser Ile
        290                 295                 300
Ile Asp Glu Pro Thr Cys Arg His Ile Ile Thr Ile Pro Ile Asn Asp
305                 310                 315                 320
Asn Thr Lys Tyr Arg Val Asn Phe Tyr Arg Asn Val Val Tyr Phe Val
                325                 330                 335
Ile Met

<210> SEQ ID NO 10
<211> LENGTH: 338
<212> TYPE: PRT
<213> ORGANISM: Plasmodium falciparum

<400> SEQUENCE: 10

Ile Asp Glu Asn Val Leu Lys Lys Tyr Asp Ile Leu Lys Lys Val Gly
1               5                   10                  15
Lys Gly Ala Tyr Gly Val Val Phe Lys Gly Arg Cys Lys Lys Asn Lys
            20                  25                  30
Asn Ile Val Ala Val Lys Lys Ile Phe Gly Ala Phe Gln Asn Cys Thr
        35                  40                  45
Asp Ala Gln Arg Thr Phe Arg Glu Ile Ile Phe Leu Tyr Glu Leu Asn
    50                  55                  60
Gly His Asp Asn Ile Ile Lys Leu Met Asp Val Ile Lys Ala Lys Asn
65                  70                  75                  80
Asp Asn Asp Ile Tyr Leu Ile Phe Asp Phe Met Glu Thr Asp Leu His
                85                  90                  95
Glu Val Ile Lys Ala Asp Leu Leu Glu Ile His Lys Lys Tyr Ile
            100                 105                 110
```

```
Ile Tyr Gln Leu Leu Arg Ala Leu Lys Tyr Ile His Ser Gly Gly Leu
            115                 120                 125

Leu His Arg Asp Ile Lys Pro Ser Asn Ile Leu Val Asn Ser Glu Cys
        130                 135                 140

His Ile Lys Val Ala Asp Phe Gly Leu Ala Arg Ser Ile Ser Thr His
145                 150                 155                 160

Val Asn Glu Asn Lys Val Pro Ile Leu Thr Asp Tyr Val Ala Thr Arg
                165                 170                 175

Trp Tyr Arg Ala Pro Glu Ile Leu Gly Ser Thr His Tyr Thr Glu
            180                 185                 190

Asp Val Asp Met Trp Ser Leu Gly Cys Ile Met Gly Glu Leu Leu Cys
        195                 200                 205

Gly Lys Pro Leu Phe Thr Gly Asn Ser Thr Met Asn Gln Leu Glu Lys
210                 215                 220

Ile Ile Gln Val Ile Gly Lys Pro Asn Lys Lys Asp Ile Glu Asp Ile
225                 230                 235                 240

Arg Ser Pro Phe Ala Glu Lys Ile Ile Ser Ser Phe Val Asp Leu Lys
                245                 250                 255

Lys Lys Asn Leu Lys Asp Ile Cys Tyr Lys Ala Ser Asn Glu Ser Leu
            260                 265                 270

Asp Leu Leu Glu Lys Leu Leu Gln Phe Asn Pro Ser Lys Arg Ile Ser
        275                 280                 285

Ala Glu Asn Ala Leu Lys His Lys Tyr Val Glu Phe His Ser Ile
290                 295                 300

Ile Asp Glu Pro Thr Cys Arg His Ile Ile Thr Ile Pro Ile Asn Asp
305                 310                 315                 320

Asn Thr Lys Tyr Arg Val Asn Phe Tyr Arg Asn Val Val Tyr Phe Val
                325                 330                 335

Ile Met

<210> SEQ ID NO 11
<211> LENGTH: 338
<212> TYPE: PRT
<213> ORGANISM: Plasmodium falciparum

<400> SEQUENCE: 11

Ile Asp Glu Asn Val Leu Lys Lys Tyr Asp Ile Leu Lys Lys Val Gly
 1               5                  10                  15

Lys Gly Ala Tyr Gly Val Val Phe Lys Gly Arg Cys Lys Lys Asn Lys
            20                  25                  30

Asn Ile Val Ala Val Lys Lys Ile Phe Gly Ala Phe Gln Asn Cys Thr
        35                  40                  45

Asp Ala Gln Arg Thr Phe Arg Glu Ile Ile Phe Leu Tyr Glu Leu Asn
    50                  55                  60

Gly His Asp Asn Ile Ile Lys Leu Met Asp Val Ile Lys Ala Lys Asn
65                  70                  75                  80

Asp Asn Asp Ile Tyr Leu Ile Phe Asp Phe Met Glu Thr Asp Leu His
                85                  90                  95

Glu Val Ile Lys Ala Asp Leu Leu Glu Glu Ile His Lys Lys Tyr Ile
            100                 105                 110

Ile Tyr Gln Leu Leu Arg Ala Leu Lys Tyr Ile His Ser Gly Gly Leu
        115                 120                 125

Leu His Arg Asp Ile Lys Pro Ser Asn Ile Leu Val Asn Ser Glu Cys
    130                 135                 140
```

-continued

```
His Ile Lys Val Ala Asp Phe Gly Leu Ala Arg Ser Ile Ser Thr His
145                 150                 155                 160

Val Asn Glu Asn Lys Val Pro Ile Leu Thr Asp Tyr Val Ala Thr Arg
                165                 170                 175

Trp Tyr Arg Ala Pro Glu Ile Leu Leu Gly Ser Thr His Tyr Thr Glu
            180                 185                 190

Asp Val Asp Met Trp Ser Leu Gly Cys Ile Met Gly Glu Leu Leu Cys
        195                 200                 205

Gly Lys Pro Leu Phe Thr Gly Asn Ser Thr Met Asn Gln Leu Glu Lys
    210                 215                 220

Ile Ile Gln Val Ile Gly Lys Pro Asn Lys Lys Asp Ile Glu Asp Ile
225                 230                 235                 240

Arg Ser Pro Phe Ala Glu Lys Ile Ile Ser Ser Phe Val Asp Leu Lys
                245                 250                 255

Lys Lys Asn Leu Lys Asp Ile Cys Tyr Lys Ala Ser Asn Glu Ser Leu
            260                 265                 270

Asp Leu Leu Glu Lys Leu Leu Gln Phe Asn Pro Ser Lys Arg Ile Ser
        275                 280                 285

Ala Glu Asn Ala Leu Lys His Lys Tyr Val Glu Glu Phe His Ser Ile
    290                 295                 300

Ile Asp Glu Pro Thr Cys Arg His Ile Ile Thr Ile Pro Ile Asn Asp
305                 310                 315                 320

Asn Thr Lys Tyr Arg Val Asn Phe Tyr Arg Asn Val Val Tyr Phe Val
                325                 330                 335

Ile Met

<210> SEQ ID NO 12
<211> LENGTH: 303
<212> TYPE: PRT
<213> ORGANISM: Leishmania mexicana

<400> SEQUENCE: 12

Ile Asp Gly Glu Val Glu Gln Arg Tyr Arg Ile Leu Arg His Ile Gly
1               5                   10                  15

Ser Gly Ala Tyr Gly Val Val Trp Cys Ala Leu Asp Arg Arg Thr Gly
            20                  25                  30

Lys Cys Val Ala Leu Lys Lys Val Tyr Asp Ala Phe Gly Asn Val Gln
        35                  40                  45

Asp Ala Gln Arg Thr Tyr Arg Glu Val Met Leu Leu Gln Arg Leu Arg
    50                  55                  60

His Asn Pro Phe Ile Val Gly Ile Leu Asp Val Ile Arg Ala Ala Asn
65                  70                  75                  80

Asp Ile Asp Leu Tyr Leu Val Phe Glu Leu Ile Glu Thr Asp Leu Thr
                85                  90                  95

Ala Ile Ile Arg Lys Asn Leu Leu Gln Arg Asp His Lys Arg Phe Leu
            100                 105                 110

Thr Tyr Gln Leu Leu Arg Thr Val Ala Gln Leu His Ala Gln Asn Ile
        115                 120                 125

Ile His Arg Asp Leu Lys Pro Ala Asn Val Phe Val Ser Ser Asp Cys
    130                 135                 140

Ser Ile Lys Leu Gly Asp Phe Gly Leu Ala Arg Thr Phe Arg Ser Gly
145                 150                 155                 160

Tyr Asp Asn Glu Gln Glu Phe Leu Asp Leu Thr Asp Tyr Ile Ala Thr
                165                 170                 175
```

```
Arg Trp Tyr Arg Ser Pro Glu Ile Leu Val Lys Ser Arg Ala Tyr Ser
            180                 185                 190

Thr Ala Met Asp Met Trp Ala Ile Gly Cys Val Ile Gly Glu Met Leu
        195                 200                 205

Leu Gly Arg Pro Leu Phe Glu Gly Arg Asn Thr Leu Asp Gln Leu Arg
    210                 215                 220

Leu Ile Ile Glu Ala Ile Gly Val Pro Ser Asp Ala Asp Val Arg Ser
225                 230                 235                 240

Leu His Ser Pro Glu Leu Glu Lys Leu Ile Asn Ser Leu Pro Thr Pro
                245                 250                 255

Leu Ile Phe Ser Pro Leu Val Gly Asn Lys Asn Leu Lys Asp Ser Glu
            260                 265                 270

Ala Thr Asp Leu Met Met Lys Leu Ile Val Phe Asn Pro Lys Arg Arg
        275                 280                 285

Leu Ser Ala Val Glu Ala Leu Gln His Pro Tyr Val Ala Pro Phe
    290                 295                 300

<210> SEQ ID NO 13
<211> LENGTH: 304
<212> TYPE: PRT
<213> ORGANISM: Dictyostelium discoideum

<400> SEQUENCE: 13

Val Pro Arg Arg Tyr Ser Ile Val Lys Cys Ile Gly His Gly Ala Tyr
1               5                   10                  15

Gly Val Val Cys Ser Ala Lys Asp Asn Leu Thr Gly Glu Lys Val Ala
            20                  25                  30

Ile Lys Lys Ile Ser Lys Ala Phe Asp Asn Leu Lys Asp Thr Lys Arg
        35                  40                  45

Thr Leu Arg Glu Ile His Leu Leu Arg His Phe Lys His Glu Asn Leu
    50                  55                  60

Ile Ser Ile Lys Asp Ile Leu Lys Pro Asn Ser Lys Glu Gln Phe Glu
65                  70                  75                  80

Asp Val Tyr Ile Val Ser Glu Leu Met Asp Thr Asp Leu His Gln Ile
                85                  90                  95

Ile Thr Ser Pro Gln Pro Leu Ser Asp Asp His Cys Gln Tyr Phe Val
            100                 105                 110

Tyr Gln Met Leu Arg Gly Leu Lys His Ile His Ser Ala Asn Val Leu
        115                 120                 125

His Arg Asp Leu Lys Pro Ser Asn Leu Leu Ile Asn Glu Asp Cys Leu
    130                 135                 140

Leu Lys Ile Cys Asp Leu Gly Leu Ala Arg Val Glu Asp Ala Thr His
145                 150                 155                 160

Gln Gly Phe Met Thr Glu Tyr Val Ala Thr Arg Trp Tyr Arg Ala Pro
                165                 170                 175

Glu Val Ile Leu Ser Trp Asn Lys Tyr Thr Lys Ala Ile Asp Ile Trp
            180                 185                 190

Ser Val Gly Cys Ile Phe Ala Glu Leu Leu Gly Arg Lys Pro Leu Phe
        195                 200                 205

Gln Gly Lys Asp Tyr Ile His Gln Ile Thr Leu Ile Ile Glu Thr Ile
    210                 215                 220

Gly Ser Pro Ser Glu Glu Asp Ile Cys Asn Ile Ala Asn Glu Gln Ala
225                 230                 235                 240

Arg Gln Phe Ile Arg Ser Leu Asn Met Gly Asn Gln Pro Lys Val Asn
                245                 250                 255
```

```
Phe Ala Asn Met Phe Pro Lys Ala Asn Pro Asp Ala Ile Asp Leu Leu
            260                 265                 270

Glu Arg Met Leu Tyr Phe Asp Pro Ser Lys Arg Leu Thr Val Glu Glu
            275                 280                 285

Ala Leu Ala His Pro Tyr Phe Gln Ser Leu His Asp Pro Ser Asp Glu
            290                 295                 300

<210> SEQ ID NO 14
<211> LENGTH: 543
<212> TYPE: PRT
<213> ORGANISM: Rattus norvegicus

<400> SEQUENCE: 14

Met Cys Ala Ala Glu Val Asp Arg His Val Ser Gln Arg Tyr Leu Ile
1               5                   10                  15

Lys Arg Arg Leu Gly Lys Gly Ala Tyr Gly Ile Val Trp Lys Ala Met
            20                  25                  30

Asp Arg Arg Thr Gly Glu Val Val Ala Ile Lys Lys Ile Phe Asp Ala
        35                  40                  45

Phe Arg Asp Gln Thr Asp Ala Gln Arg Thr Phe Arg Glu Ile Met Leu
    50                  55                  60

Leu Arg Glu Phe Gly Gly His Pro Asn Ile Ile Arg Leu Leu Asp Val
65                  70                  75                  80

Ile Pro Ala Lys Asn Asp Arg Asp Ile Tyr Leu Val Phe Glu Ser Met
                85                  90                  95

Asp Thr Asp Leu Asn Ala Val Ile Gln Lys Gly Arg Leu Leu Glu Asp
            100                 105                 110

Ile His Lys Arg Cys Ile Phe Tyr Gln Leu Leu Arg Ala Thr Lys Phe
        115                 120                 125

Ile His Ser Gly Arg Val Ile His Arg Asp Gln Lys Pro Ala Asn Val
    130                 135                 140

Leu Leu Asp Ala Ala Cys Arg Val Lys Leu Cys Asp Phe Gly Leu Ala
145                 150                 155                 160

Arg Ser Leu Ser Asp Phe Pro Glu Gly Leu Gly Gln Ala Leu Thr Glu
                165                 170                 175

Tyr Val Ala Thr Arg Trp Tyr Arg Ala Pro Glu Val Leu Leu Ser Ser
            180                 185                 190

Arg Trp Tyr Thr Pro Gly Val Asp Met Trp Ser Leu Gly Cys Ile Leu
        195                 200                 205

Gly Glu Met Leu Arg Gly Gln Pro Leu Phe Pro Gly Thr Ser Thr Phe
    210                 215                 220

His Gln Leu Glu Leu Ile Leu Glu Thr Ile Pro Leu Pro Ser Met Glu
225                 230                 235                 240

Glu Leu Gln Gly Leu Gly Ser Asp Tyr Ser Ala Leu Ile Leu Gln Asn
                245                 250                 255

Leu Gly Ser Arg Pro Arg Gln Thr Leu Asp Ala Leu Leu Pro Pro Asp
            260                 265                 270

Thr Pro Pro Glu Ala Leu Asp Leu Leu Lys Arg Leu Leu Ala Phe Ala
        275                 280                 285

Pro Asp Lys Arg Leu Ser Ala Glu Gln Ala Leu Gln His Pro Tyr Val
    290                 295                 300

Gln Arg Phe His Cys Pro Asp Arg Glu Trp Thr Arg Gly Ser Asp Val
305                 310                 315                 320

Arg Leu Pro Val His Glu Gly Asp Gln Leu Ser Ala Pro Glu Tyr Arg
                325                 330                 335
```

-continued

```
Asn Arg Leu Tyr Gln Met Ile Leu Glu Arg Arg Asn Ser Arg Ser
            340                 345                 350

Pro Arg Glu Glu Asp Leu Gly Val Val Ala Ser Arg Ala Glu Leu Arg
        355                 360                 365

Ala Ser Gln Arg Gln Ser Leu Lys Pro Gly Val Leu Pro Gln Val Leu
        370                 375                 380

Ala Glu Thr Pro Ala Arg Lys Arg Gly Pro Lys Pro Gln Asn Gly His
385                 390                 395                 400

Gly His Asp Pro Glu His Val Glu Val Arg Arg Gln Ser Ser Asp Pro
                405                 410                 415

Leu Tyr Gln Leu Pro Pro Pro Gly Ser Gly Arg Pro Pro Gly Ala
            420                 425                 430

Thr Gly Glu Pro Pro Ser Ala Pro Ser Gly Val Lys Thr His Val Arg
            435                 440                 445

Ala Val Ala Pro Ser Leu Thr Ser Gln Ala Ala Gln Ala Ala Asn
    450                 455                 460

Gln Pro Leu Ile Arg Ser Asp Pro Ala Arg Gly Gly Pro Arg Ala
465                 470                 475                 480

Val Gly Ala Arg Arg Val Pro Ser Arg Leu Pro Arg Glu Ala Pro Glu
                485                 490                 495

Pro Arg Pro Gly Arg Arg Met Phe Gly Ile Ser Val Ser Gln Gly Ala
            500                 505                 510

Gln Gly Ala Ala Arg Ala Ala Leu Gly Gly Tyr Ser Gln Ala Tyr Gly
        515                 520                 525

Thr Val Cys Arg Ser Ala Leu Gly Arg Leu Pro Leu Leu Pro Gly
            530                 535                 540
```

<210> SEQ ID NO 15
<211> LENGTH: 347
<212> TYPE: PRT
<213> ORGANISM: Caenorhabditis elegans

<400> SEQUENCE: 15

```
Val Asp Thr His Ile His Glu Lys Phe Asp Leu Gln Lys Arg Leu Gly
1               5                   10                  15

Lys Gly Ala Tyr Gly Ile Val Trp Lys Ala Tyr Asp Lys Arg Ser Arg
            20                  25                  30

Glu Thr Val Ala Leu Lys Lys Ile Phe Asp Ala Phe Arg Asn Pro Thr
        35                  40                  45

Asp Ser Gln Arg Thr Phe Arg Glu Val Met Phe Leu Gln Glu Phe Gly
    50                  55                  60

Lys His Pro Asn Val Ile Lys Leu Tyr Asn Ile Phe Arg Ala Asp Asn
65                  70                  75                  80

Asp Arg Val Ile Arg Arg Asp Ile Tyr Leu Ala Phe Glu Phe Met Glu
                85                  90                  95

Ala Asp Leu His Asn Val Ile Lys Lys Gly Ser Ile Leu Lys Asp Val
            100                 105                 110

His Lys Gln Tyr Ile Met Cys Gln Leu Phe Arg Ala Ile Arg Phe Leu
        115                 120                 125

His Ser Gly Asn Val Leu His Arg Asp Leu Lys Pro Ser Asn Val Leu
    130                 135                 140

Leu Asp Ala Asp Cys Arg Val Lys Leu Ala Asp Phe Gly Leu Ala Arg
145                 150                 155                 160

Ser Leu Ser Ser Leu Glu Asp Tyr Pro Glu Gly Gln Lys Met Pro Asp
                165                 170                 175
```

-continued

```
Leu Thr Glu Tyr Val Ala Thr Arg Trp Tyr Arg Ser Pro Glu Ile Leu
            180                 185                 190

Leu Ala Ala Lys Arg Tyr Thr Lys Gly Val Asp Met Trp Ser Leu Gly
        195                 200                 205

Cys Ile Leu Ala Glu Met Leu Ile Gly Arg Ala Leu Phe Pro Gly Ser
    210                 215                 220

Ser Thr Ile Asn Gln Ile Glu Arg Ile Met Asn Thr Ile Ala Lys Pro
225                 230                 235                 240

Ser Arg Ala Asp Ile Ala Ser Ile Gly Ser His Tyr Ala Ala Ser Val
                245                 250                 255

Leu Glu Lys Met Pro Gln Arg Pro Lys Pro Leu Asp Leu Ile Ile
            260                 265                 270

Thr Gln Ser Gln Thr Ala Ala Ile Asp Met Val Gln Arg Leu Leu Ile
        275                 280                 285

Phe Ala Pro Gln Lys Arg Leu Thr Val Glu Gln Cys Leu Val His Pro
    290                 295                 300

Tyr Val Val Gln Phe His Asn Pro Ser Glu Glu Pro Val Leu Asn Tyr
305                 310                 315                 320

Glu Val Tyr Pro Pro Leu Pro Asp His Ile Gln Leu Ser Ile Asp Asp
                325                 330                 335

Tyr Arg Asp Arg Leu Tyr Glu Met Ile Asp Glu
            340                 345

<210> SEQ ID NO 16
<211> LENGTH: 340
<212> TYPE: PRT
<213> ORGANISM: Dictyostelium discoideum

<400> SEQUENCE: 16

Ile Asp Lys His Val Leu Arg Lys Tyr Glu Val Phe His Lys Ile Gly
1               5                   10                  15

Lys Gly Ala Tyr Gly Ile Val Trp Glu Ala Ile Asp Lys Lys Pro His
            20                  25                  30

His Thr Val Ala Leu Lys Lys Ile Phe Asp Ala Phe Gln Asn Ala Thr
        35                  40                  45

Asp Ala Gln Arg Thr Phe Arg Glu Ile Met Phe Leu Gln Glu Leu His
    50                  55                  60

Gly His Glu Asn Ile Ile Lys Leu Leu Asn Val Ile Lys Ala Asp Asn
65                  70                  75                  80

Asp Arg Asp Ile Tyr Leu Val Phe Glu His Met Glu Thr Asp Leu His
                85                  90                  95

Ala Val Ile Arg Ala Lys Ile Leu Glu Glu Ile His Lys Gln Tyr Thr
            100                 105                 110

Ile Tyr Gln Leu Leu Lys Ala Leu Lys Tyr Met His Ser Ala Asn Val
        115                 120                 125

Leu His Arg Asp Ile Lys Pro Ser Asn Leu Leu Asn Ser Glu Cys
    130                 135                 140

Leu Val Lys Val Ala Asp Phe Gly Leu Ala Arg Ser Ile Thr Ser Leu
145                 150                 155                 160

Glu Ser Ile Ala Glu Ala Asn Pro Val Leu Thr Glu Tyr Val Ala Thr
                165                 170                 175

Arg Trp Tyr Arg Ala Pro Glu Ile Leu Leu Gly Ser Thr Lys Tyr Thr
            180                 185                 190

Lys Gly Val Asp Met Trp Ser Ile Gly Cys Ile Leu Gly Glu Leu Leu
        195                 200                 205
```

```
Gly Glu Lys Ala Met Phe Pro Gly Asn Ser Thr Met Asn Gln Leu Asp
    210                 215                 220

Leu Ile Ile Glu Val Thr Gly Arg Pro Ser Ala Glu Asp Ile Glu Ala
225                 230                 235                 240

Ile Lys Ser Pro Phe Ala Gly Thr Met Leu Glu Ser Leu Pro Pro Ser
                245                 250                 255

Asn Pro Arg Ser Leu Ser Asp Met Tyr Pro Ser Ala Ser Val Asp Ala
            260                 265                 270

Leu Asp Leu Leu Lys Lys Leu Ser Gln Phe Asn Pro Asp Lys Arg Ile
        275                 280                 285

Thr Ala Glu Glu Ala Leu Ala His Pro Phe Val Thr Gln Phe His Asn
    290                 295                 300

Pro Ala Glu Glu Pro His Phe Asp Arg Ile Ile Lys Ile Ser Ile Asp
305                 310                 315                 320

Asp Gly Gln Lys Phe Pro Ile Ala Glu Tyr Arg Asn Arg Leu Tyr Asn
                325                 330                 335

Asp Ile Ile Lys
            340

<210> SEQ ID NO 17
<211> LENGTH: 341
<212> TYPE: PRT
<213> ORGANISM: Leishmania mexicana

<400> SEQUENCE: 17

Met Ser Ala Glu Ile Glu Ser His Ile Leu Lys Lys Tyr Glu Ile Gln
1               5                   10                  15

Thr Gln Leu Gly Gln Gly Ala Tyr Gly Ile Val Trp Arg Ala Leu Glu
            20                  25                  30

Arg Lys His Asn Arg Val Val Ala Leu Lys Lys Ile Tyr Asp Ala Phe
        35                  40                  45

Gln Asn Ser Thr Asp Ala Gln Arg Thr Phe Arg Glu Ile Met Phe Leu
    50                  55                  60

His Arg Leu His His Pro Asn Ile Ile Arg Leu Leu His Val His Arg
65                  70                  75                  80

Ala Phe Asn Asp Arg Asp Ile Tyr Leu Val Phe Glu Tyr Met Glu Thr
                85                  90                  95

Asp Leu His Val Val Ile Arg Ala Asn Ile Leu Glu Gly Ile His Lys
            100                 105                 110

Gln Phe Ile Ile Tyr Gln Leu Leu Lys Thr Met Lys Phe Leu His Ser
        115                 120                 125

Ala Glu Ile Leu His Arg Asp Met Lys Pro Ser Asn Leu Leu Val Asn
    130                 135                 140

Ser Asp Cys Thr Met Lys Val Ala Asp Phe Gly Leu Ala Arg Ser Ile
145                 150                 155                 160

Leu Ser Leu Glu Gly Glu Gln Ala Ser Arg Pro Val Leu Thr Asp Tyr
                165                 170                 175

Ile Ala Thr Arg Trp Tyr Arg Pro Glu Ile Leu Leu Gly Ser Thr
            180                 185                 190

Arg Tyr Thr Lys Gly Val Asp Met Trp Ser Val Gly Cys Ile Leu Gly
        195                 200                 205

Glu Leu Met Leu Gly Lys Pro Met Phe Pro Gly Arg Ser Thr Thr Asn
    210                 215                 220

Gln Leu Glu Leu Ile Cys Ser Val Thr Gly Met Pro Ser Ala Ala Asp
225                 230                 235                 240
```

```
Val Ala Ala Thr Asn Ser Gln Phe Ala Asn Ala Met Leu Arg Asp Ile
                245                 250                 255

His Cys Ala His Arg Arg Thr Phe Ala Glu Leu Leu Pro Ser Ala Ser
            260                 265                 270

Ala Asp Ala Leu Asn Leu Ile Glu Arg Leu Met Cys Phe Asn Pro Asn
        275                 280                 285

Arg Arg Leu Ser Ala Ala Glu Ala Leu Glu His Pro Tyr Val Ala Ala
    290                 295                 300

Phe His Arg Pro Asp Asp Glu Pro Val Ala Pro Glu Pro Ile Thr Val
305                 310                 315                 320

Ser Leu Pro Asp Ser Gln Arg Leu Pro Leu Ala Lys Tyr Arg Asp Ala
                325                 330                 335

Ile Tyr Glu Gln Ile
                340

<210> SEQ ID NO 18
<211> LENGTH: 342
<212> TYPE: PRT
<213> ORGANISM: Drosophila melanogaster

<400> SEQUENCE: 18

Leu Asp Gln Thr Val Glu Ser Ile Phe Asp Val Arg Lys Arg Met Gly
1               5                   10                  15

Lys Gly Ala Tyr Gly Ile Val Trp Lys Ala Thr Asp Arg Arg Thr Lys
            20                  25                  30

Asn Thr Val Ala Leu Lys Lys Val Phe Asp Ala Phe Arg Asp Glu Thr
        35                  40                  45

Asp Ala Gln Arg Thr Tyr Arg Glu Val Ile Phe Leu Arg Ala Phe Arg
    50                  55                  60

Cys His Pro Asn Ile Val Arg Leu Val Asp Ile Phe Lys Ala Ser Asn
65                  70                  75                  80

Asn Leu Asp Phe Tyr Leu Val Phe Glu Phe Met Glu Ser Asp Leu His
                85                  90                  95

Asn Val Ile Lys Arg Gly Asn Val Leu Lys Asp Val His Lys Arg Phe
            100                 105                 110

Val Met Tyr Gln Leu Ile Asn Ala Ile Lys Phe Ile His Ser Gly Asn
        115                 120                 125

Val Ile His Arg Asp Leu Lys Pro Ser Asn Ile Leu Ile Asp Ser Lys
    130                 135                 140

Cys Arg Leu Lys Val Ala Asp Phe Gly Leu Ala Arg Thr Leu Ser Ser
145                 150                 155                 160

Arg Arg Ile Tyr Asp Asp Leu Glu Gln Asp Gly Met Leu Thr Asp Tyr
                165                 170                 175

Val Ala Thr Arg Trp Tyr Arg Ala Pro Glu Ile Leu Val Ala Ser Arg
            180                 185                 190

Asn Tyr Thr Lys Gly Ile Asp Met Trp Gly Leu Gly Cys Ile Leu Gly
        195                 200                 205

Glu Met Ile Arg Gln Lys Pro Leu Phe Gln Gly Thr Ser Thr Val Asn
    210                 215                 220

Gln Ile Glu Lys Ile Val Thr Ser Leu Pro Asn Val Thr Lys Leu Asp
225                 230                 235                 240

Ile Ala Ser Ile Gly Pro Ser Phe Gly Ser Val Leu Leu Ser Arg Asn
                245                 250                 255

Ile Gln Arg Asp Arg Arg Tyr Ser Leu Asp Glu Met Met Lys Asn Cys
            260                 265                 270
```

```
Cys Asp Asp Gly Ile Ser Leu Val Lys Ala Leu Leu Val Leu Asn Pro
            275                 280                 285

His Asn Arg Leu Thr Ala Lys Glu Ala Ile Arg His Pro Tyr Val Ser
            290                 295                 300

Arg Phe Gln Tyr Ala Ser Ala Glu Met Asp Leu His Met Asp Val Val
305                 310                 315                 320

Pro Pro Leu Lys Asp His Val Arg Tyr Asp Val Asp Gln Tyr Arg Asn
            325                 330                 335

Ser Leu Tyr Glu Leu Ile
            340

<210> SEQ ID NO 19
<211> LENGTH: 338
<212> TYPE: PRT
<213> ORGANISM: Plasmodium falciparum

<400> SEQUENCE: 19

Ile Asp Glu Asn Val Leu Lys Lys Tyr Asp Ile Leu Lys Lys Val Gly
  1               5                  10                  15

Lys Gly Ala Tyr Gly Val Val Phe Lys Gly Arg Cys Lys Lys Asn Lys
             20                  25                  30

Asn Ile Val Ala Val Lys Lys Ile Phe Gly Ala Phe Gln Asn Cys Thr
         35                  40                  45

Asp Ala Gln Arg Thr Phe Arg Glu Ile Ile Phe Leu Tyr Glu Leu Asn
     50                  55                  60

Gly His Asp Asn Ile Ile Lys Leu Met Asp Val Ile Ala Lys Asn
 65                  70                  75                  80

Asp Asn Asp Ile Tyr Leu Ile Phe Asp Phe Met Glu Thr Asp Leu His
                 85                  90                  95

Glu Val Ile Lys Ala Asp Leu Leu Glu Glu Ile His Lys Lys Tyr Ile
            100                 105                 110

Ile Tyr Gln Leu Leu Arg Ala Leu Lys Tyr Ile His Ser Gly Gly Leu
            115                 120                 125

Leu His Arg Asp Ile Lys Pro Ser Asn Ile Leu Val Asn Ser Glu Cys
130                 135                 140

His Ile Lys Val Ala Asp Phe Gly Leu Ala Arg Ser Ile Ser Thr His
145                 150                 155                 160

Val Asn Glu Asn Lys Val Pro Ile Leu Thr Asp Tyr Val Ala Thr Arg
                165                 170                 175

Trp Tyr Arg Ala Pro Glu Ile Leu Leu Gly Ser Thr His Tyr Thr Glu
            180                 185                 190

Asp Val Asp Met Trp Ser Leu Gly Cys Ile Met Gly Glu Leu Leu Cys
            195                 200                 205

Gly Lys Pro Leu Phe Thr Gly Asn Ser Thr Met Asn Gln Leu Glu Lys
            210                 215                 220

Ile Ile Gln Val Ile Gly Lys Pro Asn Lys Lys Asp Ile Glu Asp Ile
225                 230                 235                 240

Arg Ser Pro Phe Ala Glu Lys Ile Ile Ser Ser Phe Val Asp Leu Lys
                245                 250                 255

Lys Lys Asn Leu Lys Asp Ile Cys Tyr Lys Ala Ser Asn Glu Ser Leu
            260                 265                 270

Asp Leu Leu Glu Lys Leu Leu Gln Phe Asn Pro Ser Lys Arg Ile Ser
            275                 280                 285

Ala Glu Asn Ala Leu Lys His Lys Tyr Val Glu Glu Phe His Ser Ile
            290                 295                 300
```

```
Ile Asp Glu Pro Thr Cys Arg His Ile Ile Thr Ile Pro Ile Asn Asp
305                 310                 315                 320

Asn Thr Lys Tyr Arg Val Asn Phe Tyr Arg Asn Val Val Tyr Phe Val
                325                 330                 335

Ile Met

<210> SEQ ID NO 20
<211> LENGTH: 338
<212> TYPE: PRT
<213> ORGANISM: Plasmodium falciparum

<400> SEQUENCE: 20

Ile Asp Glu Asn Val Leu Lys Lys Tyr Asp Ile Leu Lys Lys Val Gly
1               5                   10                  15

Lys Gly Ala Tyr Gly Val Val Phe Lys Gly Arg Cys Lys Lys Asn Lys
                20                  25                  30

Asn Ile Val Ala Val Lys Lys Ile Phe Gly Ala Phe Gln Asn Cys Thr
            35                  40                  45

Asp Ala Gln Arg Thr Phe Arg Glu Ile Ile Phe Leu Tyr Glu Leu Asn
        50                  55                  60

Gly His Asp Asn Ile Ile Lys Leu Met Asp Val Ile Lys Ala Lys Asn
65                  70                  75                  80

Asp Asn Asp Ile Tyr Leu Ile Phe Asp Phe Met Glu Thr Asp Leu His
                85                  90                  95

Glu Val Ile Lys Ala Asp Leu Leu Glu Glu Ile His Lys Lys Tyr Ile
            100                 105                 110

Ile Tyr Gln Leu Leu Arg Ala Leu Lys Tyr Ile His Ser Gly Gly Leu
        115                 120                 125

Leu His Arg Asp Ile Lys Pro Ser Asn Ile Leu Val Asn Ser Glu Cys
130                 135                 140

His Ile Lys Val Ala Asp Phe Gly Leu Ala Arg Ser Ile Ser Thr His
145                 150                 155                 160

Val Asn Glu Asn Lys Val Pro Ile Leu Thr Asp Tyr Val Ala Thr Arg
                165                 170                 175

Trp Tyr Arg Ala Pro Glu Ile Leu Leu Gly Ser Thr His Tyr Thr Glu
            180                 185                 190

Asp Val Asp Met Trp Ser Leu Gly Cys Ile Met Gly Glu Leu Leu Cys
        195                 200                 205

Gly Lys Pro Leu Phe Thr Gly Asn Ser Thr Met Asn Gln Leu Glu Lys
210                 215                 220

Ile Ile Gln Val Ile Gly Lys Pro Asn Lys Lys Asp Ile Glu Asp Ile
225                 230                 235                 240

Arg Ser Pro Phe Ala Glu Lys Ile Ile Ser Ser Phe Val Asp Leu Lys
                245                 250                 255

Lys Lys Asn Leu Lys Asp Ile Cys Tyr Lys Ala Ser Asn Glu Ser Leu
            260                 265                 270

Asp Leu Leu Glu Lys Leu Leu Gln Phe Asn Pro Ser Lys Arg Ile Ser
        275                 280                 285

Ala Glu Asn Ala Leu Lys His Lys Tyr Val Glu Glu Phe His Ser Ile
290                 295                 300

Ile Asp Glu Pro Thr Cys Arg His Ile Ile Thr Ile Pro Ile Asn Asp
305                 310                 315                 320
```

```
Asn Thr Lys Tyr Arg Val Asn Phe Tyr Arg Asn Val Val Tyr Phe Val
                325                 330                 335

Ile Met
```

<210> SEQ ID NO 21
<211> LENGTH: 338
<212> TYPE: PRT
<213> ORGANISM: Plasmodium falciparum

<400> SEQUENCE: 21

```
Ile Asp Glu Asn Val Leu Lys Lys Tyr Asp Ile Leu Lys Lys Val Gly
  1               5                  10                  15

Lys Gly Ala Tyr Gly Val Val Phe Lys Gly Arg Cys Lys Lys Asn Lys
                 20                  25                  30

Asn Ile Val Ala Val Lys Lys Ile Phe Gly Ala Phe Gln Asn Cys Thr
             35                  40                  45

Asp Ala Gln Arg Thr Phe Arg Glu Ile Ile Phe Leu Tyr Glu Leu Asn
         50                  55                  60

Gly His Asp Asn Ile Ile Lys Leu Met Asp Val Ile Lys Ala Lys Asn
 65                  70                  75                  80

Asp Asn Asp Ile Tyr Leu Ile Phe Asp Phe Met Glu Thr Asp Leu His
                 85                  90                  95

Glu Val Ile Lys Ala Asp Leu Leu Glu Glu Ile His Lys Lys Tyr Ile
            100                 105                 110

Ile Tyr Gln Leu Leu Arg Ala Leu Lys Tyr Ile His Ser Gly Gly Leu
            115                 120                 125

Leu His Arg Asp Ile Lys Pro Ser Asn Ile Leu Val Asn Ser Glu Cys
130                 135                 140

His Ile Lys Val Ala Asp Phe Gly Leu Ala Arg Ser Ile Ser Thr His
145                 150                 155                 160

Val Asn Glu Asn Lys Val Pro Ile Leu Thr Asp Tyr Val Ala Thr Arg
                165                 170                 175

Trp Tyr Arg Ala Pro Glu Ile Leu Leu Gly Ser Thr His Tyr Thr Glu
            180                 185                 190

Asp Val Asp Met Trp Ser Leu Gly Cys Ile Met Gly Glu Leu Leu Cys
            195                 200                 205

Gly Lys Pro Leu Phe Thr Gly Asn Ser Thr Met Asn Gln Leu Glu Lys
        210                 215                 220

Ile Ile Gln Val Ile Gly Lys Pro Asn Lys Lys Asp Ile Glu Asp Ile
225                 230                 235                 240

Arg Ser Pro Phe Ala Glu Lys Ile Ile Ser Ser Phe Val Asp Leu Lys
                245                 250                 255

Lys Lys Asn Leu Lys Asp Ile Cys Tyr Lys Ala Ser Asn Glu Ser Leu
            260                 265                 270

Asp Leu Leu Glu Lys Leu Leu Gln Phe Asn Pro Ser Lys Arg Ile Ser
        275                 280                 285

Ala Glu Asn Ala Leu Lys His Lys Tyr Val Glu Glu Phe His Ser Ile
    290                 295                 300

Ile Asp Glu Pro Thr Cys Arg His Ile Ile Thr Ile Pro Ile Asn Asp
305                 310                 315                 320

Asn Thr Lys Tyr Arg Val Asn Phe Tyr Arg Asn Val Val Tyr Phe Val
                325                 330                 335

Ile Met
```

<210> SEQ ID NO 22
<211> LENGTH: 303
<212> TYPE: PRT
<213> ORGANISM: Leishmania mexicana

<400> SEQUENCE: 22

```
Ile Asp Gly Glu Val Glu Gln Arg Tyr Arg Ile Leu Arg His Ile Gly
 1               5                  10                  15

Ser Gly Ala Tyr Gly Val Val Trp Cys Ala Leu Asp Arg Arg Thr Gly
            20                  25                  30

Lys Cys Val Ala Leu Lys Lys Val Tyr Asp Ala Phe Gly Asn Val Gln
        35                  40                  45

Asp Ala Gln Arg Thr Tyr Arg Glu Val Met Leu Leu Gln Arg Leu Arg
    50                  55                  60

His Asn Pro Phe Ile Val Gly Ile Leu Asp Val Ile Arg Ala Ala Asn
65                  70                  75                  80

Asp Ile Asp Leu Tyr Leu Val Phe Glu Leu Ile Glu Thr Asp Leu Thr
                85                  90                  95

Ala Ile Ile Arg Lys Asn Leu Leu Gln Arg Asp His Lys Arg Phe Leu
            100                 105                 110

Thr Tyr Gln Leu Leu Arg Thr Val Ala Gln Leu His Ala Gln Asn Ile
        115                 120                 125

Ile His Arg Asp Leu Lys Pro Ala Asn Val Phe Val Ser Ser Asp Cys
    130                 135                 140

Ser Ile Lys Leu Gly Asp Phe Gly Leu Ala Arg Thr Phe Arg Ser Gly
145                 150                 155                 160

Tyr Asp Asn Glu Gln Glu Phe Leu Asp Leu Thr Asp Tyr Ile Ala Thr
                165                 170                 175

Arg Trp Tyr Arg Ser Pro Glu Ile Leu Val Lys Ser Arg Ala Tyr Ser
            180                 185                 190

Thr Ala Met Asp Met Trp Ala Ile Gly Cys Val Ile Gly Glu Met Leu
        195                 200                 205

Leu Gly Arg Pro Leu Phe Glu Gly Arg Asn Thr Leu Asp Gln Leu Arg
    210                 215                 220

Leu Ile Ile Glu Ala Ile Gly Val Pro Ser Asp Ala Asp Val Arg Ser
225                 230                 235                 240

Leu His Ser Pro Glu Leu Glu Lys Leu Ile Asn Ser Leu Pro Thr Pro
                245                 250                 255

Leu Ile Phe Ser Pro Leu Val Gly Asn Lys Asn Leu Lys Asp Ser Glu
            260                 265                 270

Ala Thr Asp Leu Met Met Lys Leu Ile Val Phe Asn Pro Lys Arg Arg
        275                 280                 285

Leu Ser Ala Val Glu Ala Leu Gln His Pro Tyr Val Ala Pro Phe
    290                 295                 300
```

<210> SEQ ID NO 23
<211> LENGTH: 304
<212> TYPE: PRT
<213> ORGANISM: Dictyostelium discoideum

<400> SEQUENCE: 23

```
Val Pro Arg Arg Tyr Ser Ile Val Lys Cys Ile Gly His Gly Ala Tyr
 1               5                  10                  15

Gly Val Val Cys Ser Ala Lys Asp Asn Leu Thr Gly Glu Lys Val Ala
            20                  25                  30
```

-continued

```
Ile Lys Lys Ile Ser Lys Ala Phe Asp Asn Leu Lys Asp Thr Lys Arg
        35                  40                  45
Thr Leu Arg Glu Ile His Leu Leu Arg His Phe Lys His Glu Asn Leu
    50                  55                  60
Ile Ser Ile Lys Asp Ile Leu Lys Pro Asn Ser Lys Glu Gln Phe Glu
65                  70                  75                  80
Asp Val Tyr Ile Val Ser Glu Leu Met Asp Thr Asp Leu His Gln Ile
                85                  90                  95
Ile Thr Ser Pro Gln Pro Leu Ser Asp Asp His Cys Gln Tyr Phe Val
                100                 105                 110
Tyr Gln Met Leu Arg Gly Leu Lys His Ile His Ser Ala Asn Val Leu
            115                 120                 125
His Arg Asp Leu Lys Pro Ser Asn Leu Leu Ile Asn Glu Asp Cys Leu
    130                 135                 140
Leu Lys Ile Cys Asp Leu Gly Leu Ala Arg Val Glu Asp Ala Thr His
145                 150                 155                 160
Gln Gly Phe Met Thr Glu Tyr Val Ala Thr Arg Trp Tyr Arg Ala Pro
                165                 170                 175
Glu Val Ile Leu Ser Trp Asn Lys Tyr Thr Lys Ala Ile Asp Ile Trp
            180                 185                 190
Ser Val Gly Cys Ile Phe Ala Glu Leu Leu Gly Arg Lys Pro Leu Phe
        195                 200                 205
Gln Gly Lys Asp Tyr Ile His Gln Ile Thr Leu Ile Ile Glu Thr Ile
    210                 215                 220
Gly Ser Pro Ser Glu Glu Asp Ile Cys Asn Ile Ala Asn Glu Gln Ala
225                 230                 235                 240
Arg Gln Phe Ile Arg Ser Leu Asn Met Gly Asn Gln Pro Lys Val Asn
                245                 250                 255
Phe Ala Asn Met Phe Pro Lys Ala Asn Pro Asp Ala Ile Asp Leu Leu
            260                 265                 270
Glu Arg Met Leu Tyr Phe Asp Pro Ser Lys Arg Leu Thr Val Glu Glu
        275                 280                 285
Ala Leu Ala His Pro Tyr Phe Gln Ser Leu His Asp Pro Ser Asp Glu
290                 295                 300
```

ISOLATED HUMAN KINASE PROTEINS, NUCLEIC ACID MOLECULES ENCODING HUMAN KINASE PROTEINS, AND USES THEREOF

FIELD OF THE INVENTION

The present invention is in the field of kinase proteins that are related to the mitogen-activated protein/extracellular signal-regulated kinase(MAP/ERK) subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I-IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

Mitogen-Activated Protein (MAP) Kinases/
Extracellular Signal-Regulated Kinases (ERKs)

The novel human protein provided by the present invention is related to the extracellular signal-regulated kinases (ERKs), which are members of the mitogen-activated protein (MAP) kinase family. ERKs are a group of intracellular enzymes that activate intracellular targets when stimulated by extracellular compounds, usually mitogens. The MAP kinases are members of the STK family. MAP kinases regulate numerous cellular signaling pathways and mediate signal transduction from the cell surface to the nucleus via phosphorylation cascades. MAP kinases also regulate cell growth, differentiation and senescence. Several subgroups have been identified, and each manifests different substrate specificities and responds to distinct extracellular stimuli (Egan, S. E. and Weinberg, R. A. (1993) *Nature* 365:781–783). MAP kinases and ERKs are activated by G protein coupled receptors. For instance, gonadotropin releasing hormone receptor activates ERK upon binding a hormone molecule. Examples of extracellular stimuli that activate mammalian MAP kinase pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1). Altered MAP kinase expression is implicated in a variety of disease conditions including cancer, inflammation, immune disorders, and disorders affecting growth and development.

MAP kinases may be the central integration point for numerous biochemical signals because they are activated by a wide variety of extracellular signals, are highly phosphorylated at threonine and tyrosine residues, and are highly conserved between species (Crews et al., *Science* 258: 478–480, 1992).

MEK1 and MEK2 are also ERKs/MAP kinases. Constitutive activation of MEK1 causes cellular transformation and therefore MEK1 is an ideal drug target for treating proliferative diseases. Furthermore, inhibition of MEK1 results in up to 80% reduction in colon carcinoma tumor growth, with no toxic side effects (Sebolt-Leopold et al., *Nature Med.* 5: 810–816, 1999). Thus, inhibitors of MEK and other ERKs/MAP kinases are useful as safe, effective treatments for cancers such as colon cancer.

The protein provided by the present invention shows a high degree of similarity to ERK7. ERK7 is constitutively active in serum-starved cells, and this activity is dependent on the presence of a C-terminal tail, which regulates the nuclear localization and growth inhibiting functions of ERK7. ERK7 therefore represents a novel type of MAP kinase characterized by the importance of interactions via its C-terminal tail, rather than extracellular signal-mediated activation cascades, in regulating its activity, localization, and function (Abe et al., *Mol Cell Biol* 1999 Feb.;19(2):1301–12). ERK7 interacts with Chloride Intracellular Channel 3 (CLIC3) which regulates cell volume, pH, membrane potential, and transepithelial transport. CLIC 3 is a part of the nuclear membrane. The C terminal domain of ERK7, rather than the kinase domain, binds CLIC3 and activates this ion channel. CLIC3 has been isolated by two-hybrid screen using the C-teminal tail of ERK7 as bait. It may be possible to isolate other ion channels by two hybrid screens using parts of ERK kinases as molecular probes. Artificial peptides or other compounds that mimic C-termini of ERKs can be used to stimulate or inhibit intracellular ion channels that regulate cell growth.

Compounds that inhibit MAP and ERK activity and slow cell growth are studied extensively. Some chemicals, like intracellular calcium chelators influence MAP kinases but do not affect ERK. Muramyl tripeptides and Lypopolysaccharides induce ERK1 and 2. Troglitazone (TRO) inhibits mitogenic signaling by insulin in vascular smooth muscle cells by interfering with ERK-dependent phosporylation. Thus, specific drugs can be developed that affect a narrow group of enzymes in the cell. The kinase specific drugs may be useful in a number of ways. For example, such kinase specific drugs enhance the effects of other drugs that affect GPCRs. Additionally, kinase specific drugs may be the only means of blocking the MAPK cascade in tissues in which the GPCR is a broadly expressed type and the ERK is a tissue specific enzyme.

For a further review of ERKs/MAP kinases, see Crews et al., *Science* 258: 478–480, 1992; Orth et al., *Science* 285: 1920–1923, 1999; Rampoldi et al., *Cytogenet. Cell Genet.* 78: 301–303, 1997; Ryan et al., *Nature* 404: 892–897, 2000; Sebolt-Leopold et al., *Nature Med.* 5: 810–816, 1999; Seger et al., *FASEB J.* 9: 726–735, 1995; Seger et al., *J. Biol.*

Chem. 267: 25628–25631, 1992; and Zheng et al., *J. Biol. Chem.* 268: 11435–11439, 1993.

Kinase proteins, particularly members of the MAP/ERK subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the MAP/ERK subfamily.

SUMMARY OF THE INVENTION

The present invention is based in part on the identification of amino acid sequences of human kinase peptides and proteins that are related to the MAP/ERK subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in the larynx epithelium, Wilms' tumors of the kidney, pancreas adenocarcinomas, fetal brain, and hippocampus.

DESCRIPTION OF THE FIGURE SHEETS

FIG. 1 provides the nucleotide sequence of a cDNA molecule that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the larynx epithelium, Wilms' tumors of the kidney, pancreas adenocarcinomas, fetal brain, and hippocampus.

FIG. 2 provides the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at five different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the MAP/ERK subfamily. Utilizing these sequences, additional genomic sequences were assembled and transcript and/or cDNA sequences were isolated and characterized. Based on this analysis, the present invention provides amino acid sequences of human kinase peptides and proteins that are related to the MAP/ERK subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the MAP/ERK subfamily and the expression pattern observed. Experimental data as provided in FIG. 1 indicates expression in the larynx epithelium, Wilms' tumors of the kidney, pancreas adenocarcinomas, fetal brain, and hippocampus. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for the known MAP/ERK proteins.

Specific Embodiments

Peptide Molecules

The present invention provides nucleic acid sequences that encode protein molecules that have been identified as being members of the kinase family of proteins and are related to the MAP/ERK subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins.

When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in the larynx epithelium, Wilms' tumors of the kidney, pancreas adenocarcinomas, fetal brain, and hippocampus. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. The gene encoding the novel kinase protein of the present invention is located on a genome component that has been mapped to human chromosome 8 (as indicated in FIG. 3), which is supported by multiple lines of evidence, such as STS and BAC map data.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. The gene encoding the novel kinase protein of the present invention is located on a genome component that has been mapped to human chromosome 8 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more filly described below.

FIG. 3 provides information on SNPs that have been found in the gene encoding the kinase proteins of the present invention. SNPs were identified at five different nucleotide positions. SNPs 5' of the ORF and in introns, particular in the first intron, may affect control/regulatory elements.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/ regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in humans in larynx epithelium, Wilms' tumors of the kidney, pancreas adenocarcinomas, fetal brain, and hippocampus. Specifically, a virtual northern blot shows expression in larynx epithelium, Wilms' tumors of the kidney, and pancreas adenocarcinomas. In addition, PCR-based tissue screening panels indicate expression in fetal brain and hippocampus. A large percentage of pharmaceutical agents are being developed that modulate the activity of kinase proteins, particularly members of the MAP/ERK subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the larynx epithelium, Wilms' tumors of the kidney, pancreas adenocarcinomas, fetal brain, and hippocampus. Such uses can readily be determined using the information provided herein, that which is known in the art, and routine experimentation.

The proteins of the present invention (including variants and fragments that may have been disclosed prior to the present invention) are useful for biological assays related to kinases that are related to members of the MAP/ERK subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in humans in larynx epithelium, Wilms' tumors of the kidney, pancreas adenocarcinomas, fetal brain, and hippocampus. Specifically, a virtual northern blot shows expression in larynx epithelium, Wilms' tumors of the kidney, and pancreas adenocarcinomas. In addition, PCR-based tissue screening panels indicate expression in fetal brain and hippocampus.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in the larynx epithelium, Wilms' tumors of the kidney, pancreas adenocarcinomas, fetal brain, and hippocampus. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in humans in larynx epithelium, Wilms' tumors of the kidney, pancreas adenocarcinomas, fetal brain, and hippocampus. Specifically, a virtual northern blot shows expression in larynx epithelium, Wilms' tumors of the kidney, and pancreas adenocarcinomas. In addition, PCR-based tissue screening panels indicate expression in fetal brain and hippocampus.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in the larynx epithelium, Wilms' tumors of the kidney, pancreas adenocarcinomas, fetal brain, and hippocampus. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the larynx epithelium, Wilms' tumors of the kidney, pancreas adenocarcinomas, fetal brain, and hippocampus. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the larynx epithelium, Wilms' tumors of the kidney, pancreas adenocarcinomas, fetal brain, and hippocampus. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in humans in larynx epithelium, Wilms' tumors of the kidney, pancreas adenocarcinomas, fetal brain, and hippocampus. Specifically, a virtual northern blot shows expression in larynx epithelium, Wilms' tumors of the kidney, and pancreas adenocarcinomas. In addition, PCR-based tissue screening panels indicate expression in fetal brain and hippocampus. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the larynx epithelium, Wilms' tumors of the kidney, pancreas adenocarcinomas, fetal brain, and hippocampus. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the larynx epithelium, Wilms' tumors of the kidney, pancreas adenocarcinomas, fetal brain, and hippocampus. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the larynx epithelium, Wilms' tumors of the kidney, pancreas adenocarcinomas, fetal brain, and hippocampus. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel kinase protein of the present invention is located on a genome component that has been mapped to human chromosome 8 (as indicated in FIG. 3), which is supported by multiple lines of evidence, such as STS and BAC map data.

FIG. 3 provides information on SNPs that have been found in the gene encoding the kinase proteins of the present invention. SNPs were identified at five different nucleotide positions. SNPs 5' of the ORF and in introns, particular in the first intron, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at five different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel kinase protein of the present invention is located on a genome component that has been mapped to human chromosome 8 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in humans in larynx epithelium, Wilms' tumors of the kidney, pancreas adenocarcinomas, fetal brain, and hippocampus. Specifically, a virtual northern blot shows expression in larynx epithelium, Wilms' tumors of the kidney, and pancreas adenocarcinomas. In addition, PCR-based tissue screening panels indicate expression in fetal brain and hippocampus. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in humans in larynx epithelium, Wilms' tumors of the kidney, pancreas adenocarcinomas, fetal brain, and hippocampus. Specifically, a virtual northern blot shows expression in larynx epithelium, Wilms' tumors of the kidney, and pancreas adenocarcinomas. In addition, PCR-based tissue screening panels indicate expression in fetal brain and hippocampus.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in the larynx epithelium, Wilms' tumors of the kidney, pancreas adenocarcinomas, fetal brain, and hippocampus. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in humans in larynx epithelium, Wilms' tumors of the kidney, pancreas adenocarcinomas, fetal brain, and hippocampus. Specifically, a virtual northern blot shows expression in larynx epithelium, Wilms' tumors of the kidney, and pancreas adenocarcinomas. In addition, PCR-based tissue screening panels indicate expression in fetal brain and hippocampus. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in the larynx epithelium, Wilms' tumors of the kidney, pancreas adenocarcinomas, fetal brain, and hippocampus.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase proteins of the present invention. SNPs were identified at five different nucleotide positions. SNPs 5' of the ORF and in introns, particular in the first intron, may affect control/regulatory elements. The gene encoding the novel kinase protein of the present invention is located on a genome component that has been mapped to human chromosome 8 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077–1080 (1988); and Nakazawa et al., PNAS 91:360–364 (1994)), the latter of which can be particularly useful for detecting point mutations in the gene (see Abravaya et al., Nucleic Acids Res. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase proteins of the present invention. SNPs were identified at five different nucleotide positions. SNPs 5' of the ORF and in introns, particular in the first intron, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in humans in larynx epithelium, Wilms' tumors of the kidney, pancreas adenocarcinomas, fetal brain, and hippocampus. Specifically, a virtual northern blot shows expression in larynx epithelium, Wilms' tumors of the kidney, and pancreas adenocarcinomas. In addition, PCR-based tissue screening panels indicate expression in fetal brain and hippocampus. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the fall length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase proteins of the present invention. SNPs were identified at five different nucleotide positions. SNPs 5' of the ORF and in introns, particular in the first intron, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as *Drosophila,* animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context.

Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide, wherein the amino acid sequence of said polypeptide consists of SEQ ID NO:2.

2. An isolated polypeptide, wherein the amino acid sequence of said polypeptide comprises SEQ ID NO:2.

3. The polypeptide of claim 1, further comprising a heterologous amino acid sequence.

4. The polypeptide of claim 2, further comprising a heterologous amino acid sequence.

5. A composition comprising the polypeptide of claim 1 and a carrier.

6. A composition comprising the polypeptide of claim 2 and a carrier.

7. A composition comprising the polypeptide of claim 3 and a carrier.

8. A composition comprising the polypeptide of claim 4 and a carrier.

* * * * *